(12) United States Patent
Capraro et al.

(10) Patent No.: US 7,326,699 B2
(45) Date of Patent: Feb. 5, 2008

(54) 4-AMINO-5-PHENYL-7-CYCLOBUTYL-PYRROLO(2,3-D)PYRIMIDINE DERIVATIVES

(75) Inventors: Hans-Georg Capraro, Rheinfelden (CH); Pascal Furet, Thann (FR); Carlos Garcia-Echeverria, Basel (CH); Paul William Manley, Arlesheim (CH)

(73) Assignee: Novartis AG, Basel (CH)

( * ) Notice: Subject to any disclaimer, the term of this patent is extended or adjusted under 35 U.S.C. 154(b) by 308 days.

(21) Appl. No.: 10/477,594

(22) PCT Filed: May 13, 2002

(86) PCT No.: PCT/EP02/05239

§ 371 (c)(1),
(2), (4) Date: Apr. 7, 2004

(87) PCT Pub. No.: WO02/092599

PCT Pub. Date: Nov. 21, 2002

(65) Prior Publication Data

US 2004/0180911 A1    Sep. 16, 2004

(30) Foreign Application Priority Data

May 14, 2001  (GB) ................. 0111764.7
Feb. 28, 2002  (GB) ................. 0204752.0

(51) Int. Cl.
C07D 417/06 (2006.01)
C07D 417/12 (2006.01)
C07D 487/04 (2006.01)
C07D 403/06 (2006.01)
C07D 403/12 (2006.01)
C07D 413/06 (2006.01)
C07D 413/12 (2006.01)
A61K 31/55 (2006.01)
A61K 31/541 (2006.01)
A61K 31/5355 (2006.01)
A61K 31/497 (2006.01)
A61K 31/519 (2006.01)
A61P 35/04 (2006.01)

(52) U.S. Cl. ................. 514/217.06; 514/228.5; 514/234.2; 514/265.1; 514/252.16; 544/61; 544/117; 544/280; 540/600

(58) Field of Classification Search ......... 544/61, 544/117, 280; 540/600; 514/228.5, 217.06, 514/234.2, 265.1, 252.16

See application file for complete search history.

(56) References Cited

U.S. PATENT DOCUMENTS

2003/0153752 A1  8/2003  Hirst et al.

2005/0215564 A1*  9/2005  Stiles et al. ............ 514/252.18

FOREIGN PATENT DOCUMENTS

| WO | WO 97 28161 | 8/1997 |
| WO | WO 97/28161 | * 8/1997 |
| WO | WO 97 49706 | 12/1997 |
| WO | WO 98/23613 | 6/1998 |
| WO | WO 99/62518 | 12/1999 |
| WO | WO 00 09145 | 2/2000 |
| WO | WO 00 17202 | 3/2000 |
| WO | WO 00 17203 | 3/2000 |
| WO | WO 01 72751 A1 | 10/2001 |
| WO | WO 02 092599 A1 | 11/2002 |
| WO | WO 03 068265 A1 | 8/2003 |

OTHER PUBLICATIONS

Werner H. et al., "New concepts in regulation and function of the insulin-like growth factors: implications for understanding normal growth and neoplasia," CMLS, Cell. Mol. Life Sci., vol. 57, pp. 932-942 (2000).
Brodt P. et al., "Inhibition of the type I insulin-like growth factor receptor expression and signaling: novel strategies for antimetastatic therapy," Biochemical Pharmacology, vol. 60, pp. 1101-1107 (2000).
Baserga, R., "The IGF-I receptor in cancer research," Experimental Cell Research, vol. 253, p. 1-6 (1999).
Baserga R. et al., "The role of the IGF-I receptor in the growth and transformation of mammalian cells," pp. 63-71 (1994).
CAS Registry Printout.
Search Report GB, dated Aug. 9, 2002.

* cited by examiner

Primary Examiner—Brenda L. Coleman
Assistant Examiner—Susanna Moore
(74) Attorney, Agent, or Firm—Oona A. Manzari; Lydia T. McNally

(57) ABSTRACT

The invention relates to new 4-amino-5-phenyl-7-cyclobutyl-pyrrolo[2,3-d]pyrimidine derivatives, processes for the preparation thereof, the application thereof in a process for the treatment of the human or animal body, the use thereof-alone or in combination with one or more other pharmaceutically active compounds-for the treatment of a disease, especially a proliferative disease, such as a tumour disease, a method for the treatment of such diseases in mammals, especially in humans, and the use of such a compound-alone or in combination with one or more other pharmaceutically active compounds-for the preparation of a pharmaceutical composition (medicament) for the treatment especially of a proliferative disease, such as a tumour.

9 Claims, No Drawings

4-AMINO-5-PHENYL-7-CYCLOBUTYL-PYRROLO(2,3-D)PYRIMIDINE DERIVATIVES

The invention relates to new 4-amino-5-phenyl-7-cyclobutyl-pyrrolo[2,3-d]pyrimidine derivatives, processes for the preparation thereof, the application thereof in a process for the treatment of the human or animal body, the use thereof—alone or in combination with one or more other pharmaceutically active compounds—for the treatment of a disease, especially a proliferative disease, such as a tumour disease, a method for the treatment of such diseases in mammals, especially in humans, and the use of such a compound—alone or in combination with one or more other pharmaceutically active compounds—for the preparation of a pharmaceutical composition (medicament) for the treatment especially of a proliferative disease, such as a tumour.

WO 98/41525 published on 24 Sep. 1998 discloses substituted 4-amino-7H-pyrrolo[2,3-d]pyrimidines having therapeutic activity as protein tyrosinie kinase inhibitors.

Surprisingly, it has now been found that the compounds of formula I, described below, are potent inhibitors of the tyrosine kinase activity of the Insulin-like growth factor I receptor (IGF-IR) and inhibit IGF-IR-dependent cell proliferation. The presence of the substituents, preferably benzyloxy substituents, at position 3 of the phenyl group of the 4 amino-5-phenyl-7-cyclobutyl-pyrrolo[2,3-d]pyrimidine scaffold together with the presence of the substituent $R_2$ as defined herein below is crucial for the efficacy and/or the specificity of the compounds of the present invention as IGF-IR tyrosine kinase inhibitors and their potential and/or selectivity to inhibit 1R-dependent cell proliferation.

The compounds of formula I permit, for example, an unexpected new therapeutic approach, especially for diseases in the treatment of which, and also for the prevention of which, an inhibition of the IGF-IR tyrosine kinase and/or of the IGF-IR-dependent cell proliferation shows beneficial effects. Such diseases include proliferative diseases, such as tumours, like for example breast, renal, prostate, colorectal, thyroid, ovarian, pancreas, neuronal, lung, uterine and gastro-intestinal tumours as well as osteosarcomas and melanomas.

The invention relates to compounds of formula I

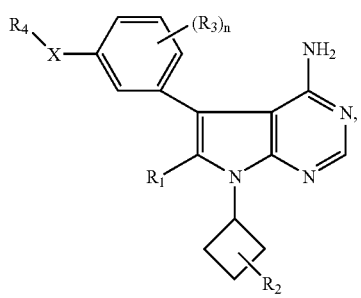

wherein
n is from 0 to 4,
$R_1$ is hydrogen, unsubstituted or substituted lower alkyl or halogen,
$R_2$ is lower alkyl substituted by hydroxy, unsubstituted, mono- or disubstituted amino or by a heterocyclic radical; a radical $R_5$—(C=Y)-Z-, wherein $R_5$ is unsubstituted or substituted lower alkyl, unsubstituted, mono- or disubstituted amino, a heterocyclic radical, or free or etherified hydroxy, Y is oxygen, sulfur or imino, and Z is either not present, lower alkyl or amino-lower alkyl; or a radical $R_6$-sulfonylamino-lower alkyl, wherein $R_6$ is unsubstituted or substituted lower alkyl, unsubstituted, mono- or disubstituted amino or phenyl optionally substituted by lower alkyl, lower alkoxy or nitro, with the proviso that $R_2$ is not carboxy, lower alkoxycarbonyl or lower alkyl substituted by hydroxy if n is 0, $R_1$ is hydrogen, $R_4$ is benzyl and X is —O—,
$R_3$ is lower alkyl, hydroxy-, amino- or halogen-substituted lower alkyl, hydroxy, cyano, lower alkoxy, lower alkanoyl, lower alkanoyloxy, amino, mono- or di-lower alkylamino, lower alkanoylamino, carboxy, lower alkoxycarbonyl or halogen, wherein the $R_3$ substituents can be selected independently of one another if n>1,
$R_4$ is a radical $R_7$—$CR_8(R_9)$—, wherein $R_7$ is cyclobutyl, cyclopentyl, cyclohexyl, phenyl, furyl, pyrrolyl, thienyl or pyridyl, said $R_7$ substitutents being optionally substituted by one or more radicals selected from lower alkyl and halogen, and $R_8$ and $R_9$ are independently of each other hydrogen, lower alkyl or halogen, and
X is selected from —O—, —NH— and —S—, or a salt thereof.

The general terms used hereinbefore and hereinafter preferably have within the context of this disclosure the following meanings, unless otherwise indicated:

Where compounds of formula I are mentioned, this is meant to include also the tautomers and N-oxides of the compounds of formula I.

Where the plural form is used for compounds, salts, and the like, this is taken to mean also a single compound, salt, or the like.

Asymmetric carbon atoms of a compound of formula I that are optionally present may exist in the (R), (S) or (R,S) configuration, preferably in the (R) or (S) configuration. Substituents at a double bond or a ring may be present in cis-(=Z-) or trans (=E-) form. The compounds may thus be present as mixtures of isomers or as pure isomers, preferably as enantiomer-pure diastereomers.

The prefix "lower" denotes a radical having up to and including a maximum of 7, especially up to and including a maximum of 4 carbon atoms, the radicals in question being either unbranched or branched with single or multiple branching.

Lower alkyl is, for example, methyl, ethyl, n-propyl, isopropyl, n-butyl, isobutyl, sec-butyl, tert-butyl, n-pentyl, isopentyl, neopentyl, n-hexyl or n-heptyl.

Lower alkylene is, for example, methylene (—CH$_2$—), ethylene (—CH$_2$—CH$_2$—), propylene (—CH$_2$—CH$_2$—CH$_2$—) or tetramethylene (—CH$_2$—CH$_2$—CH$_2$CH$_2$—).

$C_1$-$C_6$alkyl or $C_1$-$C_5$alkyl are either unbranched or branched (with single or multiple branching) alkyl radicals having from 1 to 6 or from 1 to 5 carbon atoms, respectively, and include methyl, ethyl, n-propyl, 2-propyl, n-butyl, sec-butyl, t-butyl, and the like.

In $R_2$ being lower alkyl substituted by unsubstituted, mono- or disubstituted amino or by a heterocyclic radical, lower alkyl is preferably methyl.

Lower alkyl $R_5$ is preferably methyl, isopropyl or tert-butyl.

Amino-lower alkyl Z is preferably aminomethyl.

In $R_6$-sulfonylamino-lower alkyl, lower alkyl is preferably methyl.

Lower alkyl $R_6$ is preferably methyl, ethyl or isopropyl.

Substituted lower alkyl is lower alkyl as defined above where one or more, preferably one, substituents may be present, such as amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio, halogen or a heterocyclic radical.

Substituted lower alkyl $R_5$ is preferably lower alkyl substituted by lower alkoxy, lower alkoxy-lower alkoxy or most preferably by a heterocyclic radical.

Halogen is primarily fluorine, chlorine, bromine, or iodine, especially fluorine, chlorine, or bromine.

Mono- or disubstituted amino is amino substituted by one or two radicals selected independently of one another from e.g. unsubstituted or substituted lower alkyl; phenyl or phenyl-lower alkyl wherein the phenyl radical is optionally substituted by e.g. unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio or halogen; adamantanyl; and a heterocyclic radical.

In $R_2$ being lower alkyl substituted by mono- or disubstituted amino, mono- or disubstituted amino preferably represents N-lower alkylamino or N,N-di-lower alkylamino, respectively.

Mono- or disubstituted amino $R_5$ is preferably N-lower alkylamino or N,N-di-lower alkylamino, respectively, wherein the lower alkyl moiety is optionally substituted by phenyl, lower alkyl-phenyl, lower alkoxy-phenyl, morpholinyl or N,N-di-lower alkylamino.

Mono- or disubstituted amino $R_6$ is preferably N,N-di-lower alkylamino.

A heterocyclic radical contains especially up to 20 carbon atoms and is preferably a saturated or unsaturated monocyclic radical having from 4 or 8 ring members and from 1 to 3 heteroatoms which are preferably selected from nitrogen, oxygen and sulfur, or a bi- or tricyclic radical wherein, for example, one or two benzene radicals are annellated (fused) to the mentioned monocyclic radical. Preferred above all, the heterocyclic radical contains at least one nitrogen ring atom whereby the binding of the heterocyclic radical to the radical of the molecule of formula I occurs via a nitrogen ring atom. The heterocyclic radical is optionally substituted by one or more, preferably by one or two, radicals such as e.g. unsubstituted or substituted lower alkyl, amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio, halogen, phenyl or pyridyl. Most preferably a heterocyclic radical is azetidinyl, pyrrolidinyl, piperidyl, azepanyl, piperazinyl, tetrahydropyranyl, morpholinyl or thiomorpholinyl, wherein said radicals are optionally substituted by one or more, preferably one or two, radicals selected independently of one another from the group consisting of lower alkyl, hydroxy-lower alkyl, free or etherified hydroxy, lower alkoxycarbonyl, carbamoyl, phenyl and pyridyl and the binding of the heterocyclic radical to the radical of the molecule of formula I occurs via a nitrogen ring atom.

In $R_2$ being lower alkyl substituted by a heterocyclic radical, the heterocyclic radical preferably represents azetidinyl, pyrrolidinyl, di-lower alkyl-pyrrolidinyl, aminocarbonyl-pyrrolidinyl, piperidyl, hydroxy-piperidyl, aminocarbonyl-piperidyl, azepanyl, lower alkyl-piperazinyl, lower alkoxycarbonyl-piperazinyl, phenyl-piperazinyl, pyridyl-piperazinyl, morpholinyl, di-lower alkyl-morpholinyl or thiomorpholinyl.

In $R_5$ being lower alkyl substituted by a heterocyclic radical, the heterocyclic radical preferably represents piperidyl, lower alkyl-piperazinyl or morpholinyl.

A heterocyclic radical $R_5$ is preferably pyrrolidinyl, piperidyl, lower alkyl-piperazinyl or morpholinyl.

Etherified hydroxy is, for example, alkoxy, especially lower alkoxy. The lower alkyl moiety of lower alkoxy is optionally substituted by one or more, preferably one, radicals such as e.g. amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio, halogen or a heterocyclic radical.

Etherified hydroxy $R_5$ is preferably lower alkoxy wherein the lower alkyl moiety is optionally substituted by lower alkoxy, N,N-di-lower alkylamino, lower alkyl-piperazinyl or morpholinyl.

n is preferably 0.

$R_1$ preferably represents hydrogen, lower alkyl or halogen, most preferably hydrogen or lower alkyl.

$R_4$ is preferably benzyl.

X is preferably —O—.

Y is preferably oxygen.

Salts are especially the pharmaceutically acceptable salts of compounds of formula I (or an N-oxide thereof).

Such salts are formed, for example, as acid addition salts, preferably with organic or inorganic acids, from compounds of formula I (or an N-oxide thereof) with a basic nitrogen atom, especially the pharmaceutically acceptable salts.

In the presence of negatively charged radicals, such as carboxy or sulfo, salts may also be formed with bases, e.g. metal or ammonium salts, such as alkali metal or alkaline earth metal salts, or ammonium salts with ammonia or suitable organic amines, such as tertiary monoamines.

In the presence of a basic group and an acid group in the same molecule, a compound of formula I (or an N-oxide thereof) may also form internal salts.

For isolation or purification purposes it is also possible to use pharmaceutically unacceptable salts, for example picrates or perchlorates. Only the pharmaceutically acceptable salts or free compounds (if the occasion arises, in the form of pharmaceutical compositions) attain therapeutic use, and these are therefore preferred.

In view of the close relationship between the novel compounds in free form and in the form of their salts, including those salts that can be used as intermediates, for example in the purification or identification of the novel compounds, hereinbefore and hereinafter any reference to the free compounds is to be understood as referring also to the corresponding salts, as appropriate and expedient.

The compounds of formula I have valuable pharmacological properties, as described hereinbefore and hereinafter.

The efficacy of the compounds of the invention as inhibitors of IGF-IGF-IR tyrosine kinase activity can be demonstrated using a cellular "Capture ELISA". In this assay the activity of the compounds of the invention against Insulin-like growth factor I (IGF-I) induced autophosphorylation of the IGF-IGF-IR is determined. The assay is conducted as follows:

For the assay NIH-3T3 mouse fibroblasts transfected with human IGF-IR cDNA (complete human IGF-IR cDNA: GenBank Acc. No. NM_000875), prepared as described in Kato et al., J. Biol. Chem. 268, 2655-61, 1993, are used. The cells which overexpress human IGF-IGF-IR are cultured in Dulbecco's minimal essential (DMEM) medium, containing 10% Fetal Calf Serum (FCS). For the assay 5,000 cells/well are plated on day 1 on 96-well plates (Costar #3595) In normal growth medium and incubated for 2 days at 37° C. in a standard $CO_2$ cell incubator. The density of the cells does not exceed 70-80% at day 3. On day 3 the medium is discarded and the cells are incubated for 24 h in minimal medium (DMEM, containing 0.5% FCS). Compounds of formula I [starting from 10 mM dimethyl sulfoxide (DMSO) stock solutions] are added to produce final concentrations of 0.01, 0.03, 0.1, 0.3, 1, 3 and 10 µM to determine the $IC_{50}$ value. The cells are incubated for 90 min in the presence of a compound of formula I. Thereafter the cells are stimulated with 50 µl IGF-I (final concentration of IGF-I in the well=10 ng/ml; IGF-I is obtained from Sigma; Product Code: I3769) and incubated for 10 min at 37° C.

The medium is discarded and the cells are washed twice with PBS/O (=Phosphate-Buffered Saline without $CaCl_2$) and lysed for 15 min on ice with 50 µl/well RIPA-buffer [50 mM Tris.HCl, pH=7.2, 120 mM NaCl, 1 mM EDTA, 6 mM EGTA, 1% NP-40, 20 mM NaF, 1 mM benzamidine, 15 mM sodium pyrophosphate, 1 mM Phenyl methyl sulphonyl fluoride (PMSF) and 0.5 mM $Na_3VO_4$] and shaken for 10 min using a 96-well plate shaker (=cellular extracts).

Packard HTRF-96 black plates are coated with 50 µl IGF-IR monoclonal Antibody (mAB) (Santa Cruz; Cat. No.: SC-462) in a concentration of 5 µg/ml at 4° C. overnight. The plates are washed twice with 0.05% (v/v) Tween-20 in Phosphate-Buffered Saline (PBS) and once with nanopure $H_2O$. Blocking is done for 2 h at room temperature (RT) with 3% Bovine Serum Albumin (BSA) in TBS-T buffer (20 mM Tris.HCl, pH=7.6, 137 mM NaCl, 0.05% Tween-20). After blocking, the plates are washed once with nanopure $H_2O$.

Cellular extracts (40 µl/well) are pipetted onto the precoated Packard plates, together with 40 µl of the anti-phosphotyrosine mouse mAB PY-20 conjugated with Alkaline Phosphatase (AP) (1:1000 diluted in RIPA buffer; the antibody is obtained from Transduction Labs; Cat. No.: P11120).

After incubating the extracts and the secondary antibody for 2 h at 4° C., the extracts are discarded, the plates are washed twice with 0.05% (v/v) Tween-20 in PBS and once with nanopure water.

90 µl/well AP substrate (CDP-Star; obtained from Tropix; Cat. No.: MS100RY) are then added and the plates are incubated for 45 min at RT in the dark, followed by measuring AP activity in a Packard Top Count Microplate Scintillation Counter. The $IC_{50}$ values for the compounds of formula I are calculated via linear regression analysis using the GraphPad In-stat program (GraphPad Software, USA). $IC_{50}$ values in the range of 5 nM to 1 µM, especially in the range of 5 nM to 300 nM are found.

In vivo activity in the nude mouse xenotransplant model: female BALB/c nude mice (8-12 weeks old, Novartis Animal Farm, Sisseln, Switzerland) are kept under sterile conditions with water and feed ad libitum. Tumours are induced by subcutaneous injection of tumour cells (human epithelial cell line A-431; American Type Culture Collection (ATCC), Rockville, Md., USA, Catalogue Number ATCC CRL 1555; cell line from an 85-year-old woman; epidermoid carcinoma cell line) into carrier mice. The resulting tumours pass through at least three consecutive transplantations before the start of treatment. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 $mm^3$. Tumour growth is measured two to three times a week and 24 hours after the last treatment by determining the length of two perpendicular axes. The tumour volumes are calculated in accordance with published methods (see Evans et al., Brit. J. Cancer 45, 466-8, 1982). The anti-tumour efficacy is determined as the mean increase in tumour volume of the treated animals divided by the mean increase in tumour volume of the untreated animals (controls) and, after multiplication by 100, is expressed as T/C %. Tumour regression (given in %) is reported as the smallest mean tumour volume in relation to the mean tumour volume at the start of treatment. The test compound is administered daily by gavage.

As an alternative to cell line A-431, other cell lines may also be used in the same manner, for example:
the MCF-7 breast adenocarcinoma cell line (ATCC No. HTB 22; see also J. Natl. Cancer Inst. (Bethesda) 51, 1409-16, 1973); and
the DU145 prostate carcinoma cell line DU 145 (ATCC No. HTB 81; see also Cancer Res. 37, 4049-58,1978).

On the basis of these studies, a compound of formula I according to the invention shows therapeutic efficacy especially against proliferative diseases responsive to an inhibition of the IGF-IR tyrosine kinase.

In general, the invention relates also to the use of a compound of formula I for the inhibition of the IGF-IR tyrosine kinase.

In addition to the inhibition of the IGF-IR tyrosine kinase, the compounds of formula I also inhibit the tyrosine kinase activity of the receptor tyrosine kinase Flt-3. The compounds of formula I are therefore also useful for the treatment of proliferative diseases, especially tumour diseases, responsive to an inhibition of the Flt-3 tyrosine kinase receptor. Such tumour diseases include e.g. leukemias and myelodysplastic syndrome. Aberrant expression of the Flt-3 gene has been documented in both adult and childhood leukemias including acute myeloid leukemia (AML), AML with trilineage myelodysplasia (AML/TMDS), acute lymphoblastic leukemia (ALL), and myelodysplastic syndrome (MDS). The compounds of formula I are therefore suitable for the treatment of these diseases, especially for the treatment of AML since activating mutations of the Flt-3 receptor have been found in about 35% of patients with AML, and are associated with a poor prognosis.

The Flt-3 inhibitory activity of a compound of formula I can be shown in a tyrosine kinase inhibition assay using the cytoplasmic kinase domain of Flt-3. The assay is performed as follows: The baculovirus donor vector pFbacG01 (GIBCO) is used to generate a recombinant baculovirus that expresses the amino acid region amino acids 563-993 of the intra-cytoplasmic kinase domain of human Flt-3. The coding sequence for the cytoplasmic domain of Flt-3 is amplified by PCR from human c-DNA libraries (Clontech). The amplified DNA fragments and the pFbacG01 vector are made compatible for ligation by digestion with BamH1 and HindIII. Ligation of these DNA fragments results in the baculovirus donor plasmid Flt-3(1.1). The production of the viruses, the expression of proteins in Sf9 cells and the purification of the GST-fused proteins are performed as follows:

Production of virus: Transfer vector (pFbacG01-Flt-3) containing the Flt-3 kinase domain is transfected into the DH10Bac cell line (GIBCO) and the cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 or Sf21 cells (American Type Culture Collection) are then transfected in 25 cm² flasks with the viral DNA using Cellfectin reagent.

Determination of small scale protein expression in Sf9 cells: Virus containing media is collected from the transfected cell culture and used for Infection to Increase Its titer. Virus containing media obtained after two rounds of infection is used for large-scale protein expression. For large-scale protein expression 100 cm² round tissue culture plates are seeded with $5 \times 10^7$ cells/plate and infected with 1 mL of virus-containing media (approx. 5 MOls). After 3 days the cells are scraped off the plate and centrifuged at 500 rpm for 5 min. Cell pellets from 10-20, 100 cm² plates, are resuspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpms for 20 min.

Purification of GST-tagged proteins: The centrifuged cell lysate is loaded onto a 2 mL glutathione-sepharose column (Pharmacia) and washed three times with 10 mL of 25 mM Tris HCl, pH 7.5, 2 mM EDTA, 1 mM DTT, 200 mM NaCl. The GST-tagged protein is then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Measure of enzyme activity. Tyrosine protein kinase assays with purified GST-Flt-3 are carried out in a final volume of 30 μL containing 200-1800 ng of enzyme protein (depending on the specific activity), 20 mM Tris-HCl, pH 7.6, 3 mM MnCl₂, 3 mM MgCl₂, 1 mM DTT, 10 μM Na₃VO₄, 3 μg/mL poly(Glu,Tyr) 4:1, 1% DMSO, 8.0 μM ATP and 0.1 μCi [γ³³P] ATP. The activity is assayed in the presence or absence of inhibitors, by measuring the incorporation of $^{33}P$ from [γ³³P] ATP into the poly(Glu,Tyr) substrate. The assay (30 μL) is carried out in 96-well plates at ambient temperature for 20 min under conditions described below and terminated by the addition of 20 μL of 125 mM EDTA. Subsequently, 40 μL of the reaction mixture is transferred onto Immobilon-PVDF membrane (Millipore, Bedford, Mass., USA) previously soaked for 5 min with methanol, rinsed with water, then soaked for 5 min with 0.5% H₃PO₄ and mounted on vacuum manifold with disconnected vacuum source. After spotting all samples, vacuum is connected and each well rinsed with 200 μL 0.5% H₃PO₄. Membranes are removed and washed 4× on a shaker with 1.0% H₃PO₄, once with ethanol. Membranes are counted after drying at ambient temperature, mounting in Packard Top-Count 96-well frame, and addition of 10 μL/well of Microscint TM (Packard). IC₅₀ values are calculated by linear regression analysis of the percentage inhibition of each compound in duplicate, at four concentrations (usually 0.01, 0.1, 1 and 10 μM). One unit of protein kinase activity is defined as 1 nmole of ³³P ATP transferred from [γ³³P] ATP to the substrate protein per minute per mg of protein at 37° C.

In addition to the diseases mentioned above, the compounds of formula I can further be used in the treatment of obesity and are also suitable for the treatment of ischemic retinopathies, such as e.g. diabetic retinopathy and retinopathy of prematurity (ROP). The effectiveness of the compounds of formula I in these diseases can be shown by using in vitro- or in vivo-tests known in the art.

Compounds of formula I are also useful for preventing or combating graft vessel diseases, e.g. allo- or xenotransplant vasculopathies, e.g. graft vessel atherosclerosis or chronic graft rejection, e.g. in a transplant of organ, tissue or cells, e.g. heart, lung, combined heart-lung, liver, kidney or pancreatic transplants (e.g. pancreatic islet cells), or for preventing or treating vein graft stenosis, restenosis and/or vascular occlusion following vascular injury, e.g. caused by catherization procedures or vascular scraping procedures such as percutaneous transluminal angioplasty, laser treatment or other invasive procedures which disrupt the integrity of the vascular intima or endothelium.

With the groups of preferred compounds of formula I mentioned hereinafter, definitions of substituents from the general definitions mentioned hereinbefore may reasonably be used, for example, to replace more general definitions with more specific definitions or especially with definitions characterized as being preferred.

Preference is given to a compound of formula I, wherein n is from 0 to 4, $R_1$ is hydrogen, unsubstituted or substituted lower alkyl or halogen, $R_2$ is lower alkyl substituted by hydroxy, unsubstituted, mono- or disubstituted amino or by a heterocyclic radical; a radical $R_5$—(C=Y)-Z-, wherein $R_5$ is unsubstituted or substituted lower alkyl, unsubstituted, mono- or disubstituted amino, a heterocyclic radical, or free or etherified hydroxy, Y is oxygen, sulfur or imino, and Z is either not present, lower alkyl or amino-lower alkyl; or a radical $R_6$-sulfonylamino-lower alkyl, wherein $R_6$ is unsubstituted or substituted lower alkyl, unsubstituted, mono- or disubstituted amino or phenyl optionally substituted by lower alkyl, lower alkoxy or nitro, with the proviso that $R_2$ is not carboxy, lower alkoxycarbonyl or lower alkyl substituted by hydroxy if n is 0, $R_1$ is hydrogen, $R_4$ is benzyl and X is —O—, $R_3$ is lower alkyl or lower alkoxy, wherein the $R_3$ substituents can be selected independently of one another if n>1, $R_4$ is a radical $R_7$—$C_8(R_9)$—, wherein $R_7$ is cyclobutyl, cyclopentyl, cyclohexyl, phenyl, furyl, pyrrolyl, thienyl, pyridyl or phenyl substituted by one or more substitutents selected from lower alkyl and halogen, and $R_8$ and $R_9$ are independently of each other hydrogen, lower alkyl or halogen, and X is selected from —O—, —NH— and —S—, or a salt thereof.

Special preference is given to a compound of formula I, wherein n is 0, $R_1$ is hydrogen, unsubstituted or substituted lower alkyl or halogen, $R_2$ is lower alkyl substituted by unsubstituted, mono- or disubstituted amino or by a heterocyclic radical; a radical $R_5$—(C=Y)-Z-, wherein $R_5$ is unsubstituted or substituted lower alkyl, unsubstituted, mono- or disubstituted amino, a heterocyclic radical, or if Z is present is also free or etherified hydroxy, Y is oxygen, sulfur or imino, and Z is either not present, lower alkyl or amino-lower alkyl; or a radical $R_6$-sulfonylamino-lower alkyl, wherein $R_6$ is unsubstituted or substituted lower alkyl, unsubstituted, mono- or disubstituted amino or phenyl optionally substituted by lower alkyl, lower alkoxy or nitro, $R_4$ is benzyl, and X is selected from —O—, —NH— and —S—, or a salt thereof.

Special preference is further given to a compound of formula I, wherein n is 0, $R_1$ is hydrogen, unsubstituted or substituted lower alkyl or halogen, $R_2$ is lower alkyl substituted by a substituted heterocyclic radical; a radical $R_5$—(C=Y)-Z-, wherein $R_5$ is unsubstituted or substituted lower alkyl, unsubstituted, mono- or disubstituted amino, a heterocyclic radical, or if Z is present is also free or etherified hydroxy, Y is oxygen, sulfur or imino, and Z is either not present, lower alkyl or amino-lower alkyl, with the proviso that Z is not present or lower alkyl if $R_5$ is lower alkyl and Z is lower alkyl or amino-lower alkyl if $R_5$ is mono- or disubstituted amino or a heterocyclic radical; or a radical $R_6$-sulfonylamino-lower alkyl, wherein $R_6$ is unsubstituted or substituted lower alkyl, unsubstituted, mono- or disubstituted amino or phenyl optionally substituted by lower alkyl, lower alkoxy or nitro, $R_4$ is benzyl, and X is selected from —O—, —NH— and —S—, or a salt thereof.

Preference is especially given to a compound of formula I, wherein n is 0, $R_1$ is hydrogen, unsubstituted or substituted lower alkyl or halogen, $R_2$ is lower alkyl substituted by amino, N-lower alkylamino, N,N-di-lower alkylamino or by an unsubstituted heterocyclic radical; or a radical $R_5$—(C=Y)-Z-, wherein $R_5$ is lower alkyl, mono- or disubstituted amino or a heterocyclic radical, Y is oxygen, sulfur or imino, and Z is amino-lower alkyl if $R_5$ is lower alkyl and not present if $R_5$ is a heterocyclic radical or mono- or disubstituted amino, $R_4$ is benzyl, and X is selected from —O—, —NH— and —S—, or a salt thereof.

Especially preferred is further a compound of formula I, wherein n is 0, $R_1$ is hydrogen, unsubstituted or substituted lower alkyl or halogen, $R_2$ is lower alkyl substituted by unsubstituted, mono- or disubstituted amino or by a heterocyclic radical having from 4 to 8 ring members and from 1 to 3 heteroatoms whereby at least one heteroatom is nitrogen and the binding of the heterocyclic radical to lower alkyl occurs via a nitrogen ring atom; a radical $R_5$—(C=Y)-Z-, wherein $R_5$ is lower alkyl, unsubstituted, mono- or disubstituted amino, a heterocyclic radical having from 4 to 8 ring members and from 1 to 3 heteroatoms whereby at least one heteroatom is nitrogen and the binding of the heterocyclic radical occurs via a nitrogen ring atom, lower alkyl substituted by said heterocyclic radical or by one or more radicals selected independently of one another from the group consisting of amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio and halogen, or if Z is present is also free or etherified hydroxy, Y is oxygen, sulfur or imino, and Z is either not present, lower alkyl or amino-lower alkyl; or a radical $R_6$-sulfonylamino-lower alkyl, wherein $R_6$ is unsubstituted or substituted lower alkyl, unsubstituted, mono- or disubstituted amino or phenyl optionally substituted by lower alkyl, lower alkoxy or nitro, $R_4$ is benzyl, and X is selected from —O—, —NH— and —S—, or a salt thereof.

Very especially preferred is a compound of formula I, wherein n is 0, $R_1$ is hydrogen, $R_2$ is amino-lower alkyl, N-lower alkylamino-lower alkyl, N,N-di-lower alkylamino-lower alkyl, morpholinyl-lower alkyl, piperidyl-lower alkyl, pyrrolidinyl-lower alkyl, lower alkyl-piperazinyl-lower alkyl, adamantanyl-amino-lower alkyl, hydroxy-piperidyl-lower alkyl, azepanyl-lower alkyl, di-lower alkyl-pyrrolidinyl-lower alkyl, azetidinyl-lower alkyl, aminocarbonyl-piperidyl-lower alkyl, pyridyl-piperazinyl-lower alkyl, thiomorpholinyl-lower alkyl, di-lower alkyl-morpholinyl-lower alkyl, aminocarbonyl-pyrrodinyl-lower alkyl, lower alkoxycarbonyl-piperazinyl-lower alkyl or phenyl-piperazinyl-lower alkyl; a radical $R_5$—(C=Y)-Z-, wherein $R_5$ is lower alkyl, amino, N-lower alkylamino, N,N-di-lower alkylamino, N-(phenyl-lower alkyl)amino, N-(lower alkyl-phenyl-lower alkyl)-amino, N-(lower alkoxy-phenyl-lower alkyl)-amino, N-(morpholinyl-lower alkyl)-amino, N,N-di-lower alkylamino-lower alkylamino, pyrrolidinyl, piperidyl, morpholinyl, lower alkyl-piperazinyl, piperidyl-lower alkyl, morpholinyl-lower alkyl, lower alkyl-piperazinyl-lower alkyl, lower alkoxy, lower alkoxy-lower alkoxy, lower alkoxy-lower alkyl, lower alkoxy-lower alkoxy-lower alkyl, N,N-di-lower alkylamino-lower alkoxy, morpholinyl-lower alkoxy or lower alkyl-piperazinyl-lower alkoxy, Y is oxygen or imino, and Z is either not present or amino-lower alkyl; or a radical $R_6$-sulfonylamino-lower alkyl, wherein $R_6$ is lower alkyl, lower alkyl-phenyl, lower alkoxy-phenyl, nitrophenyl or N,N-di-lower alkylamino, $R_4$ is benzyl, and X is —O—, or a salt thereof.

Especially preferred is further also a compound of formula I, wherein n is 0, $R_1$ is hydrogen, lower alkyl or halogen, $R_2$ is a radical selected from the group consisting of hydroxy-lower alkyl, carboxy, lower alkoxycarbonyl, amino-lower alkyl, N-lower alkylamino-lower alkyl, (tetrahydropyranyl-amino)-lower alkyl, N,N-di-lower alkylamino-lower alkyl, N-lower alkylaminocarbonyl, N,N-di-lower alkylaminocarbonyl, guanidino-lower alkyl, lower alkyl-sulfonylamino-lower alkyl, lower alkoxy-phenyl-sulfonylamino-lower alkyl, lower alkyl-phenyl-sulfonylamino-lower alkyl, nitrophenyl-sulfonylamino-lower alkyl, N,N-di-lower alkylamino-sulfonylamino-lower alkyl, lower alkoxycarbonylamino-lower alkyl, lower alkoxy-lower alkoxycarbonylamino-lower alkyl, ureido-lower alkyl, N-lower alkylamino-carbonylamino-lower alkyl, N,N-di-lower alkylamino-carbonylamino-lower alkyl, N-(phenyl-lower alkyl)-amino-carbonylamino-lower alkyl, N-(lower alkyl-phenyl-lower alkyl)-amino-carbonylamino-lower alkyl, N-(lower alkoxy-phenyl-lower alkyl)-amino-carbonylamino-lower alkyl, N-(morpholinyl-lower alkyl)-amino-carbonylamino-lower alkyl, N,N-di-lower alkylamino-lower alkylamino-carbonylamino-lower alkyl, lower alkyl-carbonylaminolower alkyl, piperidyl-lower alkyl-carbonylamino-lower alkyl, morpholinyl-lower alkyl-carbonylamino-lower alkyl, lower alkyl-piperazinyl-lower alkyl-carbonylamino-lower alkyl, morpholinyl-lower alkyl, piperidyl-lower alkyl, pyrrolidinyl-lower alkyl, [(hydroxy-lower alkyl)pyrrolidinyl]-lower alkyl, lower alkyl-piperazinyl-lower alkyl, adamantanyl-amino-lower alkyl, hydroxy-piperidyl-lower alkyl, azepanyl-lower alkyl, di-lower alkyl-pyrrolidinyl-lower alkyl, azetidinyl-lower alkyl, aminocarbonyl-piperidyl-lower alkyl, pyridyl-piperazinyl-lower alkyl, thiomorpholinyl-lower alkyl, di-lower alkyl-morpholinyl-lower alkyl, aminocarbonyl-pyrrodinyl-lower alkyl, lower alkoxycarbonyl-piperazinyl-lower alkyl, phenyl-piperazinyl-lower alkyl, lower alkoxy-lower alkylcarbonylamino-lower alkyl, lower alkoxy-lower alkoxy-lower alkylcarbonyl-amino-lower alkyl, pyrrolidinyl-carbonylamino-lower alkyl, piperidyl-carbonylamino-lower alkyl, morpholinyl-carbonylamino-lower alkyl, lower alkyl-piperazinyl-carbonylamino-lower alkyl, N,N-di-lower alkylamino-lower alkoxycarbonylamino-lower alkyl, morpholinyl-lower alkoxycarbonylamino-lower alkyl and lower alkyl-piperazinyl-lower alkoxycarbonylamino-lower alkyl, with the proviso that $R_2$ is not hydroxy-lower alkyl, carboxy or lower alkoxycarbonyl if $R_1$ is hydrogen, $R_4$ is benzyl, and X is —O—, or a salt thereof.

Most preferred is a compound of formula I, wherein n is 0, $R_1$ is hydrogen, $R_2$ is a radical selected from the group consisting of amino-lower alkyl, N-lower alkylamino-lower alkyl, N,N-di-lower alkylamino-lower alkyl, N-lower alkylamino-carbonyl, N,N-di-lower alkylamino-carbonyl, guanidino-lower alkyl, lower alkyl-sulfonylamino-lower alkyl, lower alkoxy-phenyl-sulfonylamino-lower alkyl, lower alkyl-phenyl-sulfonylamino-lower alkyl, nitrophenyl-sulfonylamino-lower alkyl, N,N-di-lower alkylamino-sulfonylamino-lower alkyl, lower alkoxycarbonylamino-lower alkyl, lower alkoxy-lower alkoxycarbonylamino-lower alkyl, ureido-lower alkyl, N-lower alkylamino-carbonylamino-lower alkyl, N,N-di-lower alkylamino-carbonylamino-lower alkyl, N-(phenyl-lower alkyl)-amino-carbonylamino-lower alkyl, N-(lower alkyl-phenyl-lower alkyl)-amino-carbonylamino-lower alkyl, N-(lower alkoxy-phenyl-lower alkyl)-amino-carbonylamino-lower alkyl, N-(morpholinyl-lower alkyl)-amino-carbonylamino-lower alkyl, N,N-di-lower alkylamino-lower alkylamino-carbonylamino-lower alkyl, lower alkylcarbonylamino-lower alkyl, piperidyl-lower alkylcarbonylamino-lower alkyl, morpholinyl-lower alkylcarbonylamino-lower alkyl, lower alkyl-piperazinyl-lower alkylcarbonylamino-lower alkyl, morpholinyl-lower alkyl, piperidyl-lower alkyl, pyrrolidinyl-lower alkyl, lower alkyl-piperazinyl-lower alkyl, adamantanyl-amino-lower alkyl, hydroxy-piperidyl-lower alkyl, azepanyl-lower alkyl, di-lower alkyl-pyrrolidinyl-lower alkyl, azetidinyl-lower alkyl, aminocarbonyl-piperidyl-lower alkyl, pyridyl-piperazinyl-lower alkyl, thiomorpholinyl-lower alkyl, di-lower alkyl-morpholinyl-lower alkyl, aminocarbonyl-pyrrodinyl-lower alkyl, lower alkoxycarbonyl-piperazinyl-lower alkyl, phenyl-piperazinyl-lower alkyl, lower alkoxy-lower alkylcarbonylamino-lower alkyl, lower alkoxy-lower alkoxy-lower alkylcarbonylamino-lower alkyl, pyrrolidinyl-carbonylamino-lower alkyl, piperidyl-carbonylamino-lower alkyl, morpholinyl-carbonylamino-lower alkyl, lower alkyl-piperazinyl-carbonylamino-lower alkyl, N,N-di-lower alkylamino-lower alkoxycarbonylamino-lower alkyl, morpholinyl-lower alkoxycarbonylamino-lower alkyl and lower alkyl-piperazinyl-lower alkoxycarbonylamino-lower alkyl, $R_4$ is benzyl, and X is —O—, or a salt thereof.

Especially preferred is further a compound of formula I, wherein $R_2$ is in the 3 position of the cyclobutane ring.

Very special preference is given to a compound of formula I mentioned in the Examples below, or a salt, especially a pharmaceutically acceptable salt, thereof.

Also especially preferred are all compounds of formula I, which in the above-described "Capture ELISA" assay have an $IC_{50}$ value of less than 300 nM, most preferably those having an $IC_{50}$ value of less than 100 nM.

The compounds of formula I or salts thereof are prepared in accordance with processes known per se (see also WO 97/28161), though not previously described for the manufacture of the compounds of the formula I, especially whereby a) in order to prepare a compound of formula I, in which $R_2$ is lower alkyl substituted by amino, a compound of formula II

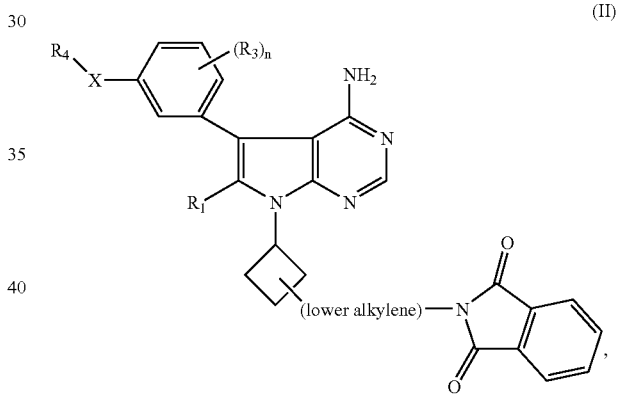

wherein n, $R_1$, $R_3$, $R_4$ and X have the meanings as defined for a compound of formula I, is reacted with hydrazine;

b) in order to prepare a compound of formula I, in which $R_2$ is a radical $R_5$—(C=Y)-Z- wherein $R_5$ is unsubstituted, mono- or disubstituted amino, Y is oxygen and Z is not present or lower alkyl, a compound of formula III

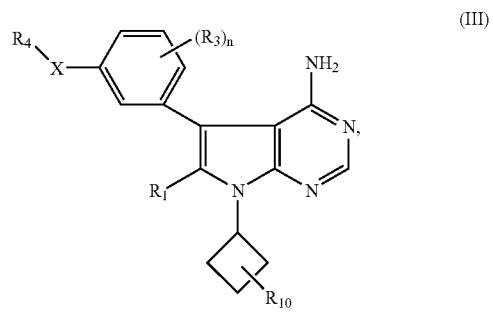

in which $R_{10}$ is a radical HO—(C=O)-Z- wherein Z is not present or lower alkyl, and n, $R_1$, $R_3$, $R_4$ and X have the meanings as defined for a compound of formula I, is reacted with a compound of the formula $R_5$—H wherein $R_5$ is unsubstituted, mono- or disubstituted amino;

c) in order to prepare a compound of formula I, in which $R_2$ is lower alkyl substituted by mono- or disubstituted amino, a compound of formula I, in which $R_2$ is a radical $R_5$—(C=Y)-Z- wherein $R_5$ is mono- or disubstituted amino, Y is oxygen and Z is not present or lower alkyl, is reacted with lithium aluminium hydride;

d) in order to prepare a compound of formula I, in which $R_2$ is lower alkyl substituted by mono- or disubstituted amino or by a heterocyclic radical containing at least one nitrogen ring atom whereby the binding of the heterocyclic radical to lower alkyl occurs via a nitrogen ring atom, a compound of formula IV

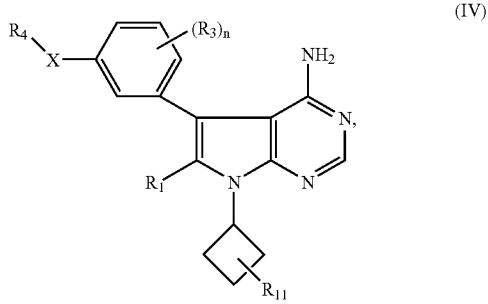

(IV)

in which $R_{11}$ is lower alkyl substituted by 4-methylphenyl-sulfonyloxy and n, $R_1$, $R_3$, $R_4$ and X have the meanings as defined for a compound of formula I, is reacted with a compound of the formula $R_{17}$—H In which $R_{17}$ is mono- or disubstituted amino or a heterocyclic radical containing at least one nitrogen ring atom wherein the heterocyclic radical is attached to the hydrogen atom of $R_{17}$—H via a nitrogen ring atom;

e) in order to prepare a compound of formula I, in which $R_2$ is a radical $R_6$-sulfonylamino-lower alkyl wherein $R_6$ has the meanings as defined above under formula I, a compound of formula I, in which $R_2$ is amino-lower alkyl, is reacted with $R_6$-sulfonyl halide;

f) in order to prepare a compound of formula I, In which $R_2$ is a radical $R_5$—(C=Y)-Z- wherein $R_5$ is free or etherified hydroxy, Y is oxygen and Z is amino-lower alkyl, a compound of formula I, in which $R_2$ is amino-lower alkyl, is reacted with a compound of the formula $R_5$—(C=O)-Halogen wherein $R_5$ is free or etherified hydroxy;

g) in order to prepare a compound of formula I, in which $R_2$ is a radical $R_5$—(C=Y)-Z- wherein $R_5$ is unsubstituted or monosubstituted amino, Y is oxygen or sulfur and Z is amino-lower alkyl, a compound of formula I, in which $R_2$ is amino-lower alkyl, is reacted with a compound of the formula $R_{12}$—N=C=Y wherein Y is oxygen or sulfur, the radical $R_{12}$—NH— corresponding to unsubstituted or monosubstituted amino $R_5$;

h) in order to prepare a compound of formula I, in which $R_2$ is a radical $R_5$—(C=Y)-Z- wherein $R_5$ is unsubstituted, mono- or disubstituted amino or a heterocyclic radical containing at least one nitrogen ring atom whereby the binding of the heterocyclic radical occurs via a nitrogen ring atom, Y is oxygen and Z is amino-lower alkyl, a compound of formula I, in which $R_2$ is a radical $R_5$—(C=Y)-Z- wherein $R_5$ is imidazol-1-yl, Y is oxygen and Z is amino-lower alkyl, is reacted with a compound of the formula $R_5$—H, in which $R_5$ is unsubstituted, mono- or disubstituted amino, or a heterocyclic radical which contains at least one nitrogen ring atom;

i) in order to prepare a compound of formula I, in which $R_2$ is a radical $R_5$—(C=Y)-Z- wherein $R_5$ is unsubstituted or substituted lower alkyl, Y is oxygen and Z is amino-lower alkyl, a compound of formula I, in which $R_2$ is amino-lower alkyl, is reacted with a compound of the formula $R_5$—(C=O)-Halogen wherein $R_5$ is unsubstituted or substituted lower alkyl;

j) in order to prepare a compound of formula I, in which $R_2$ is a radical $R_5$—(C=Y)-Z- wherein $R_5$ is lower alkyl substituted by a heterocyclic radical containing at least one nitrogen ring atom whereby the binding of the heterocyclic radical to lower alkyl occurs via a nitrogen ring atom, Y is oxygen and Z is amino-lower alkyl, a compound of formula V

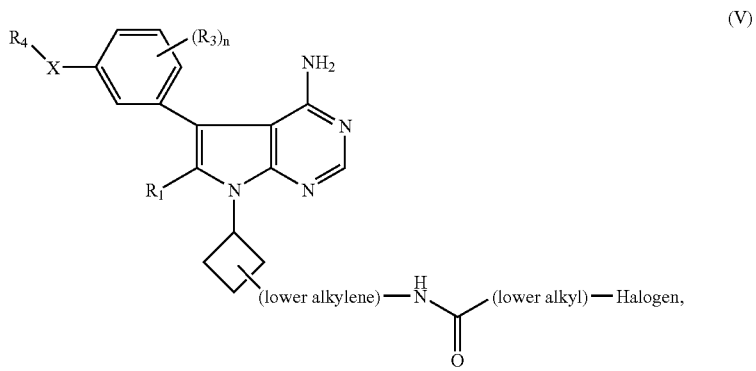

(V)

in which n, $R_1$, $R_3$, $R_4$ and X have the meanings as defined for a compound of formula I, is reacted with a compound of the formula $R_{18}$—H in which $R_{18}$ is a heterocyclic radical containing at least one nitrogen ring atom wherein the heterocyclic radical is attached to the hydrogen atom of $R_{18}$—H via a nitrogen ring atom;

k) in order to prepare a compound of formula I, in which $R_2$ is a radical $R_5$—(C=Y)-Z- wherein $R_5$ is lower alkylamino wherein the lower alkyl moiety is substituted by unsubstituted, mono- or disubstituted amino or by a heterocyclic radical containing at least one nitrogen ring atom whereby the binding of the heterocyclic radical to the lower alkyl moiety occurs via a nitrogen ring atom, Y is oxygen or sulfur and Z is amino-lower alkyl, a compound of formula VI

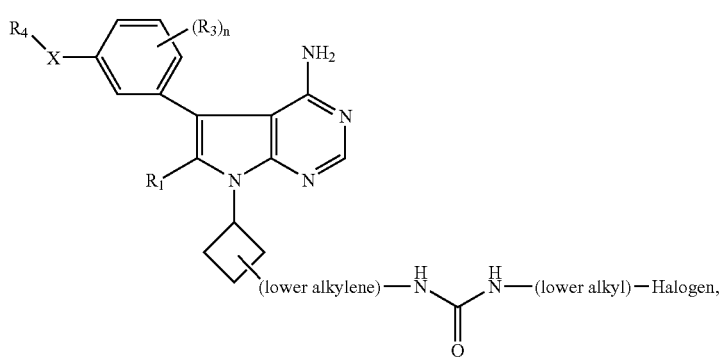

(VI)

in which Y is oxygen or sulfur and n, $R_1$, $R_3$, $R_4$ and X have the meanings as defined for a compound of formula I, is reacted with a compound of the formula $R_{13}$—H, in which $R_{13}$ is unsubstituted, mono- or disubstituted amino or a heterocyclic radical containing at least one nitrogen ring atom wherein the heterocyclic radical is attached to the hydrogen atom of $R_{13}$—H via a nitrogen ring atom;

l) in order to prepare a compound of formula I, in which $R_2$ is a radical $R_5$—(C=Y)-Z- wherein $R_5$ is lower alkoxy substituted by unsubstituted, mono- or disubstituted amino or by a heterocyclic radical containing at least one nitrogen ring atom whereby the binding of the heterocyclic radical to the lower alkyl moiety of lower alkoxy occurs via a nitrogen ring atom, Y is oxygen and Z is amino-lower alkyl, a compound of formula VII

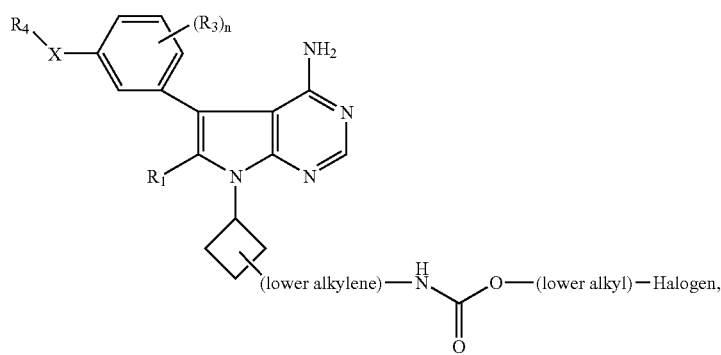

(VII)

in which n, $R_1$, $R_3$, $R_4$ and X have the meanings as defined for a compound of formula I, is reacted with a compound of the formula $R_{14}$—H, in which $R_{14}$ is unsubstituted, mono- or disubstituted amino or a heterocyclic radical containing at least one nitrogen ring atom wherein the heterocyclic radical is attached to the hydrogen atom of $R_{14}$—H via a nitrogen ring atom;

m) in order to prepare a compound of formula I, in which $R_1$ is halogen, a compound of formula I, in which $R_1$ is hydrogen, is reacted with N-halosuccinimide;

n) in order to prepare a compound of formula I, in which $R_1$ is lower alkyl, a compound of formula I, in which $R_1$ is halogen, is reacted with tetra(lower alkyl) tin;

o) in order to prepare a compound of formula I, a compound of formula IX

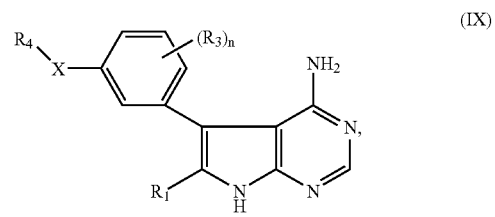

(IX)

in which n, $R_1$, $R_3$, $R_4$ and X have the meanings as defined for a compound of formula I, is reacted with a compound of formula X

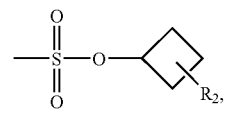

(X)

in which $R_2$ has the meanings as defined for a compound of formula I;

p) in order to prepare a compound of formula I, in which $R_2$ is lower alkyl substituted by hydroxy wherein hydroxy is attached to a primary carbon atom, a compound of formula I, in which $R_2$ is a radical $R_5$—(C=Y)-Z- wherein $R_5$ is etherifed hydroxy, Y is oxygen and Z is not present or $C_1$-$C_6$ alkyl, is reacted with lithium aluminiumhydride;

q) in order to prepare a compound of formula I, in which $R_2$ is lower alkyl substituted by hydroxy wherein hydroxy is attached to a secondary or tertiary carbon atom, a compound of formula XI

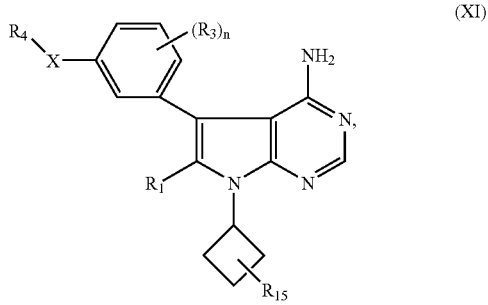

(XI)

in which $R_{15}$ is a radical $R_{16}$—(C=O)-Q- wherein $R_{16}$ is hydrogen or $C_1$-$C_5$alkyl and Q is not present or $C_1$-$C_5$alkyl, is reacted with a Grignard reagent of the formula $C_1$-$C_6$alkyl-Mg-halide;

whereby functional groups which are present in the starting compounds of processes a) to q) and are not intended to take part in the reaction, are present in protected form if necessary, and protecting groups that are present are cleaved, whereby said starting compounds may also exist in the form of salts provided that a salt-forming group is present and a reaction in salt form is possible;

and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

DESCRIPTION OF THE PROCESS VARIANTS

Regarding Process a):

The reaction between a compound of formula II and hydrazine, in the form of e.g. hydrazine monohydrate, preferably takes place in a suitable inert solvent, especially alcohols, e.g. lower alcohols, such as ethanol and in an inert, for example an argon, atmosphere, preferably at room temperature (RT). Hydrazine is used in excess, preferably about 15 equivalents, compared to the compound of formula II.

Regarding Process b):

The reaction between a compound of formula III and a compound of the formula $R_5$—H, wherein $R_5$ is unsubstituted, mono- or disubstituted amino, preferably takes place in the presence of O-(1,2-dihydro-2-oxo-1-pyridyl)-1,1,3,3-tetramethyluronium tetrafluoroborate and diisopropylethylamine, in a suitable inert solvent, such as for example N,N-dimethylformamide, preferably at RT.

Regarding Process c):

The reaction between a compound of formula I, in which $R_2$ is a radical $R_5$—(C=Y)-Z- wherein $R_5$ is mono- or disubstituted amino, Y is oxygen and Z is not present or lower alkyl, and lithium aluminium hydride preferably takes place in a suitable inert solvent, such as for example anhydrous tetrahydrofuran (THF), preferably at temperatures of between 0° C. and RT, most preferably by slowly warming the reaction mixture from 0° C. to RT for about 14 hours.

Regarding Process d):

The reaction between a compound of formula IV and a compound of the formula $R_{17}$—H preferably takes place at RT. If at the reaction temperature the compound of formula $R_{17}$—H is in the form of a liquid and the compound of formula IV is soluble therein, no additional solvent is needed.

Regarding Process e):

The reaction between a compound of formula I, in which $R_2$ is amino-lower alkyl, and $R_6$-sulfonyl halide, in which $R_6$ is as defined above under formula I, preferably takes place in the presence of triethylamine, in a suitable inert solvent, such as for example dichloromethane, and in an inert, for example an argon, atmosphere, preferably at about 0° C. In $R_6$-sulfonyl halide, halide is preferably chloride.

Regarding Process f):

The reaction between a compound of formula I, in which $R_2$ is amino-lower alkyl, and a compound of the formula $R_5$—(C=O)-Halogen, wherein $R_5$ is free or etherifed hydroxy and Halogen is preferably chlorine, preferably takes place in the presence of triethylamine, in a suitable inert solvent, such as for example dichloromethane, preferably at RT.

Regarding Process g):

The reaction between a compound of formula I, in which $R_2$ is amino-lower alkyl, and a compound of the formula $R_{12}$—N=C=Y preferably takes place in a suitable inert solvent, such as for example acetonitrile, preferably at RT.

Regarding Process h):

The reaction between a compound of formula I, in which $R_2$ is a radical $R_5$—(C=Y)-Z- wherein $R_5$ is imidazol-1-yl, Y is oxygen and Z is amino-lower alkyl, and a compound of the formula $R_5$—H, in which $R_5$ is unsubstituted, mono- or disubstituted amino, or a heterocyclic radical which contains at least one nitrogen ring atom, preferably takes place in the presence of triethylamine, in a suitable inert solvent, such as for example acetonitrile, and in an inert, for example an argon, atmosphere, preferably at RT.

Regarding Process i):

The reaction between a compound of formula I, in which $R_2$ is amino-lower alkyl, and a compound of the formula $R_5$—(C=O)Halogen, wherein $R_5$ is unsubstituted or substituted lower alkyl and Halogen is preferably chlorine, preferably takes place in a suitable inert solvent, such as for example N,N-dimethylformamide, preferably at RT.

Regarding Process j):

The reaction between a compound of formula V and a compound of the formula $R_{18}$—H preferably takes place in a suitable inert solvent, especially alcohols, e.g. lower alcohols, such as ethanol, preferably at the reflux temperature of the solvent employed. In a compound of formula V, Halogen is preferably chlorine.

Regarding Process k):

The reaction between a compound of formula VI and a compound of the formula $R_{13}$—H preferably takes place in a suitable inert solvent, especially alcohols, e.g. lower alcohols, such as ethanol, preferably at the reflux temperature of the solvent employed.

In a compound of formula VI, Halogen is preferably chlorine or bromine.

Regarding Process I):

The reaction between a compound of formula VII and a compound of the formula $R_{14}$—H preferably takes place in a suitable inert solvent, such as for example acetonitrile, preferably at the reflux temperature of the solvent employed. In a compound of formula VII, Halogen is preferably bromine.

Regarding Process m):

The reaction between a compound of formula I, in which $R_1$ is hydrogen, and N-halosuccinimide, preferably takes place in a suitable inert solvent, such as for example N,N-dimethylformamide, and in an inert, for example an argon, atmosphere, preferably at RT in the dark. N-halosuccinimide is preferably N-bromosuccinimide.

Regarding Process n):

The reaction between a compound of formula I, in which $R_1$ is halogen, and tetra(lower alkyl) tin, preferably takes place in the presence of tetrakistriphenylphosphin palladium, in a suitable inert solvent, such as for example N,N-dimethylformamide, and in an inert, for example an argon, atmosphere, preferably at elevated temperature such as around 100° C.

Regarding Process o):

The reaction between a compound of formula IX and a compound of formula X preferably takes place in the presence of a suitable base, such as potassium carbonate, and in the presence of 18-crown-6 ether, in a suitable inert solvent, such as for example N,N-dimethylformamide, preferably at elevated temperature such as around 80° C.

Regarding Process p):

The reaction between a compound of formula I, in which $R_2$ is a radical $R_5$—(C=Y)-Z- wherein $R_5$ is etherified hydroxy, Y is Oxygen and Z is not present or $C_1$-$C_6$alkyl, and lithium aluminiumhydride, preferably takes place in a suitable inert solvent, such as for example THF, preferably at around 0° C.

Regarding Process q):

The reaction between a compound of formula XI and a Grignard reagent of the formula $C_1$-$C_6$alkyl-Mg-halide is carried out under conditions known in the art, for example at RT and using diethylether as the solvent.

Additional Process Steps

In the additional process steps, carried out as desired, functional groups of the starting compounds which should not take part in the reaction may be present in unprotected form or may be protected for example by one or more protecting groups. The protecting groups are then wholly or partly removed according to one of the known methods.

Protecting groups, and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be removed readily, i.e. without the occurrence of undesired secondary reactions, for example by solvolysis, reduction, photolysis or alternatively under physiological conditions.

The end products of formula I may however also contain substituents that can also be used as protecting groups in starting materials for the preparation of other end products of formula I. Thus, within the scope of this text, only a readily removable group that is not a constituent of the particular desired end product of formula I is designated a "protecting group", unless the context indicates otherwise.

A compound of formula I can be converted to a corresponding N-oxide. The reaction is carried out with a suitable oxidizing agent, preferably a peroxide, for example m-chloroperbenzoic acid, in a suitable solvent, e.g. halogenated hydrocarbon, typically chloroform or dichloromethane, or in a lower alkanecarboxylic acid, typically acetic acid, preferably at a temperature between 0° C. and the boiling temperature of the reaction mixture, especially at about RT.

General Process Conditions

All process steps described here can be carried out under known reaction conditions, preferably under those specifically mentioned, in the absence of or usually in the presence of solvents or diluents, preferably those that are inert to the reagents used and able to dissolve them, in the absence or presence of catalysts, condensing agents or neutralising agents, for example ion exchangers, typically cation exchangers, for example in the H$^+$ form, depending on the type of reaction and/or reactants at reduced, normal, or elevated temperature, for example in the range from −100° C. to about 190° C., preferably from about −80° C. to about 150° C., for example at −80 to −60° C., at RT, at −20 to 40° C. or at the boiling point of the solvent used, under atmospheric pressure or in a closed vessel, if need be under pressure, and/or in an inert, for example an argon or nitrogen, atmosphere.

The invention relates also to those embodiments of the process in which one starts from a compound obtainable at any stage as an intermediate and carries out the missing steps, or breaks off the process at any stage, or forms a starting material under the reaction conditions, or uses said starting material in the form of a reactive derivative or salt, or produces a compound obtainable by means of the process according to the invention under those process conditions, and further processes the said compound in situ. In the preferred embodiment, one starts from those starting materials which lead to the compounds described hereinabove as preferred.

In the preferred embodiment, a compound of formula I (or an N-oxide thereof) is prepared according to the processes and process steps defined in the Examples.

The compounds of formula I (or N-oxides thereof), including their salts, are also obtainable in the form of hydrates, or their crystals can include for example the solvent used for crystallisation (present as solvates).

Starting Materials

New starting materials and/or intermediates, as well as processes for the preparation thereof, are likewise the subject of this invention. In the preferred embodiment, such starting materials are used and reaction conditions so selected as to enable the preferred compounds to be obtained.

The starting materials used in the above described processes a) to q) are known, capable of being prepared according to known processes (see also WO 97/28161), or commercially obtainable; in particular, they can be prepared using processes as described in the Examples.

In the preparation of starting materials, existing functional groups which do not participate in the reaction should, if necessary, be protected. Preferred protecting groups, their introduction and their removal are described above or in the examples. In place of the respective starting materials and transients, salts thereof may also be used for the reaction, provided that salt-forming groups are present and the reaction with a salt is also possible. Where the term starting materials is used hereinbefore and hereinafter, the salts thereof are always included, insofar as reasonable and possible.

A compound of formula II can be prepared for example by reacting a compound of formula VIII

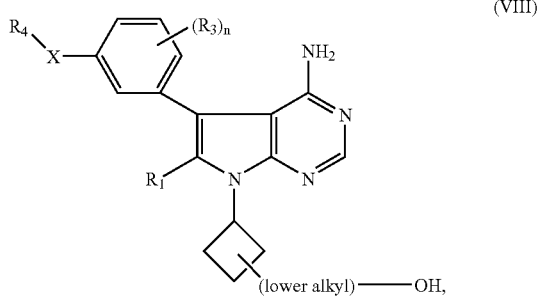

wherein n, $R_1$, $R_3$, $R_4$ and X have the meanings as defined for a compound of formula I, with phthalimide, in the presence of triphenylphosphine and diethyl azodicarboxylate, in an inert solvent, for example dry tetrahydrofuran, and in an inert, for example an argon, atmosphere, preferably at RT.

A compound of formula VIII can be obtained according to process p) or q).

A compound of formula I, in which $R_2$ is a radical $R_5$—(C=Y)-Z- wherein $R_5$ is mono- or disubstituted amino, Y is oxygen and Z is not present or lower alkyl, can be obtained according to process b).

A compound of formula IV can be prepared for example by reacting a compound of formula VIII with p-toluenesulfonyl halide, preferably p-toluenesulfonyl chloride, in an inert solvent, for example pyridine, preferably at −20° C.

A compound of formula I, in which $R_2$ is amino-lower alkyl, can be obtained according to process a).

A compound of formula I, in which $R_2$ is a radical $R_5$—(C=Y)-Z- wherein $R_5$ is imidazol-1-yl, Y is oxygen and Z is amino-lower alkyl, can be obtained for example by reacting a compound of formula I, in which $R_2$ is amino-lower alkyl, with 1,1-carbonyldiimidazole, in the presence of triethylamine, in an inert solvent, for example acetonitrile, and in an inert, for example an argon, atmosphere, preferably at RT.

A compound of formula V can be prepared for example by reacting a compound of formula I, in which $R_2$ is amino-lower alkyl, with halogen-lower alkylcarbonyl halide, preferably chloro-lower alkylcarbonyl chloride, in the presence of triethylamine, in an inert solvent, for example acetonitrile, preferably at RT.

A compound of formula VI can be obtained for example by reacting a compound of formula I, in which $R_2$ is amino-lower alkyl, with a compound of the formula halogen-lower alkyl-N=C=Y, wherein Y is oxygen or sulfur and halogen is preferably chlorine and bromine, in an inert solvent, for example acetonitrile, preferably at RT.

A compound of formula VII can be prepared for example by reacting a compound of formula I, In which $R_2$ is amino-lower alkyl, with halogen-lower alkyl halogen formate, preferably bromo-lower alkyl chloroformate, in the presence of triethylamine, in an inert solvent, for example dichloromethane, preferably at RT.

The remaining starting materials are known, capable of being prepared according to known processes, or commercially available; or in particular, they can be prepared using processes as described in the Examples.

Pharmaceutical Compositions, Methods, Uses and Combinations

The present invention relates also to pharmaceutical compositions that comprise a compound of formula I, or a pharmaceutically acceptable salt thereof, as active ingredient and that can be used especially in the treatment of the diseases mentioned at the beginning.

The present invention also relates to pro-drugs of a compound of formula I that convert in vivo to the compound of formula I as such. Any reference to a compound of formula I is therefore to be understood as referring also to the corresponding pro-drugs of the compound of formula I, as appropriate and expedient.

Compositions for enteral administration, such as nasal, buccal, rectal or, especially, oral administration, and for parenteral administration, such as intravenous, intramuscular or subcutaneous administration, to warm-blooded animals, especially humans, are especially preferred. The compositions contain the active ingredient alone or, preferably, together with a pharmaceutically acceptable carrier. The dosage of the active ingredient depends upon the disease to be treated and upon the species, its age, weight, and individual condition, the individual pharmacokinetic data, and the mode of administration.

The invention relates also to compounds of formula I, or a pharmaceutically acceptable salt thereof, as such or in the form of a pharmaceutical composition, for use in a method for the prophylactic or especially therapeutic treatment of the human or animal body, to a process for the preparation thereof (especially in the form of compositions for the treatment of tumours) and to a method of treating the above-mentioned diseases, primarily tumour diseases, especially those mentioned above.

The invention relates also to processes and to the use of compounds of formula I, or a pharmaceutically acceptable salt thereof, for the preparation of pharmaceutical compositions which comprise compounds of formula I, or a pharmaceutically acceptable salt thereof, as active component (active ingredient).

If desired, the said pharmaceutical compositions may also contain further active components, such as other chemotherapy drugs, and/or may be used in combination with known therapeutic processes, for example the administration of hormonal medicines or radiation.

Preference is for a pharmaceutical composition which is suitable for administration to a warm-blooded animal, especially humans or commercially useful mammals suffering from a disease which responds to an inhibition of the IGF-IR tyrosine kinase or of the IGF-IR-dependent cell proliferation, especially a neoplastic disease, comprising an effective quantity of a compound of formula I for the inhibition of the IGF-IR tyrosine kinase or of the IGF-IR-dependent cell proliferation, or a pharmaceutically acceptable salt thereof, together with at least one pharmaceutically acceptable carrier.

A pharmaceutical composition for the prophylactic or especially therapeutic management of neoplastic and other proliferative diseases of a warm-blooded animal, especially a human or a commercially useful mammal requiring such treatment, especially suffering from such a disease, comprising as active ingredient in a quantity that is prophylactically or especially therapeutically active against said diseases a new compound of formula I, or a pharmaceutically acceptable salt thereof, is likewise preferred.

The pharmaceutical compositions comprise from approximately 1% to approximately 95% active Ingredient, single-dose administration forms comprising in the preferred embodiment from approximately 20% to approximately 90% active ingredient and forms that are not of single-dose type comprising in the preferred embodiment from approximately 5% to approximately 20% active ingredient. Unit dose forms are, for example, coated and uncoated tablets, ampoules, vials, suppositories or capsules. Examples are capsules containing from about 0.05 g to about 1.0 g of active substance.

The pharmaceutical compositions of the present invention are prepared in a manner known per se, for example by means of conventional mixing, granulating, coating, dissolving or lyophilising processes.

The invention relates likewise to a process or a method for the treatment of one of the pathological conditions mentioned hereinabove, especially a disease which responds to an inhibition of the IGF-IR tyrosine kinase or of the IGF-IR-dependent cell proliferation, especially a corresponding neoplastic disease. The compounds of formula I, or a pharmaceutically acceptable salt thereof, can be administered as such or in the form of pharmaceutical compositions, prophylactically or therapeutically, preferably in an amount effective against the said diseases, to a warm-blooded animal, for example a human, requiring such treatment, the compounds especially being used in the form of pharmaceutical compositions. In the case of an individual having a bodyweight of about 70 kg the daily dose administered is from approximately 0.1 g to approximately 5 g, preferably from approximately 0.5 g to approximately 2 g, of a compound of the present invention.

The present invention relates especially also to the use of a compound of formula I, or a pharmaceutically acceptable salt thereof, especially a compound of formula I which is said to be preferred, or a pharmaceutically acceptable salt thereof, as such or in the form of a pharmaceutical composition with at least one pharmaceutically acceptable carrier, for the therapeutic and also prophylactic management of one or more of the diseases mentioned hereinabove, preferably a disease which responds to an inhibition of the IGF-IR tyrosine kinase or of the IGF-IR-dependent cell proliferation, especially a neoplastic disease, in particular if the said disease responds to an inhibition of the IGF-IR tyrosine kinase or of the IGF-IR-dependent cell proliferation.

The present invention relates especially also to the use of a compound of formula I, or a pharmaceutically acceptable salt thereof, especially a compound of formula I which is said to be preferred, or a pharmaceutically acceptable salt thereof, for the preparation of a pharmaceutical composition for the therapeutic and also prophylactic management of one or more of the diseases mentioned hereinabove, especially a neoplastic disease, in particular if the disease responds to an inhibition of the IGF-IR tyrosine kinase or of the IGF-IR-dependent cell proliferation.

A compound of formula I may also be used to advantage in combination with other antiproliferative agents. Such antiproliferative agents include, but are not limited to aromatase inhibitors, antiestrogens, topoisomerase I inhibitors, topoisomerase II inhibitors, microtubule active agents, alkylating agents, histone deacetylase inhibitors, farnesyl transferase inhibitors, COX-2 inhibitors, MMP inhibitors, mTOR inhibitors, antineoplastic antimetabolites, platin compounds, compounds decreasing the protein kinase activity and further anti-angiogenic compounds, gonadorelin agonists, antiandrogens, bengamides, bisphosphonates and trastuzumab.

The term "aromatase inhibitors" as used herein relates to compounds which inhibit the estrogen production, i.e. the conversion of the substrates androstenedione and testosterone to estrone and estradiol, respectively. The term includes, but is not limited to steroids, especially exemestane and formestane and, in particular, non-steroids, especially aminoglutethimide, vorozole, fadrozole, anastrozole and, very especially, letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™. Aminoglutethimide can be administered, e.g., in the form as it is marketed, e.g. under the trademark ORIMETEN™.

A combination of the invention comprising an antineoplastic agent which is an aromatase inhibitor is particularly useful for the treatment of hormone receptor positive breast tumors.

The term "antiestrogens" as used herein relates to compounds which antagonize the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™.

The term "topoisomerase I inhibitors" as used herein includes, but is not limited to topotecan, irinotecan, 9-nitrocamptothecin and the macromolecular camptothecin conjugate PNU-166148 (compound A1 in WO99/17804). Irinotecan can be administered, e.g., in the form as it is marketed, e.g. under the trademark CAMPTOSAR™. Topotecan can be administered, e.g., in the form as it is marketed, e.g. under the trademark HYCAMTIN™.

The term "topoisomerase II inhibitors" as used herein includes, but is not limited to the antracyclines doxorubicin (including liposomal formulation, e.g. CAELYX™), epirubicin, idarubicin and nemorubicin, the anthraquinones mitoxantrone and losoxantrone, and the podophillotoxines etoposide and teniposide. Etoposide can be administered, e.g., in the form as it is marketed, e.g. under the trademark ETOPOPHOS™. Teniposide can be administered, e.g., in the form as it is marketed, e.g. under the trademark VM 26-BRISTOL™. Doxorubicin can be administered, e.g., in the form as it is marketed, e.g. under the trademark ADRIBLASTIN™. Epirubicin can be administered, e.g., in the form as it is marketed, e.g. under the trademark FARMORUBICIN™. Idarubicin can be administered, e.g., in the form as it is marketed, e.g. under the trademark ZAVEDOS™. Mitoxantrone can be administered, e.g., in the form as it is marketed, e.g. under the trademark NOVANTRON™.

The term "microtubule active agents" relates to microtubule stabilizing and microtubule destabilizing agents including, but not limited to the taxanes paclitaxel and docetaxel, the vinca alkaloids, e.g., vinblastine, especially vinblastine sulfate, vincristine especially vincristine sulfate, and vinorelbine, discodermolide and epothilones, such as epothilone B and D. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agents" as used herein includes, but is not limited to cyclophosphamide, ifosfamide and melphalan. Cydophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "histone deacetylase inhibitors" relates to compounds which inhibit the histone deacetylase and which possess antiproliferative activity.

The term "farnesyl transferase inhibitors" relates to compounds which inhibit the farnesyl transferase and which possess antiproliferative activity.

The term "COX-2 inhibitors" relates to compounds which inhibit the cyclooxygenase type 2 enzyme (COX-2) and which possess antiproliferative activity such as celecoxib (Celebrex®) and rofecoxib (Vioxx®).

The term "MMP inhibitors" relates to compounds which inhibit the matrix metalloproteinase (MMP) and which possess antiproliferative activity.

The term "mTOR inhibitors" relates to compounds which inhibit the mammalian target of rapamycin (mTOR) and which possess antiproliferative activity such as sirolimus (Rapamune®), everolimus (Certican™), CCl-779 and ABT578.

The term "antineoplastic antimetabolites" includes, but is not limited to 5-fluorouracil, 5-fluorouracil, tegafur, capecitabine, cladribine, cytarabine, fludarabine phosphate, fluorouridine, gemcitabine, 6-mercaptopurine, hydroxyurea, methotrexate, edatrexate and salts of such compounds, and furthermore ZD 1694 (RALTITREXED™), LY231514 (ALIMTA™), LY264618 (LOMOTREXOL™) and OGT719.

The term "platin compounds" as used herein includes, but is not limited to carboplatin, cisplatin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds decreasing the protein kinase activity and further anti-angiogenic compounds" as used herein includes, but is not limited to compounds which decrease the activity of e.g. the Vascular Endothelial Growth Factor (VEGF), the Epidermal Growth Factor (EGF) and c-Src and anti-angiogenic compounds having another mechanism of action than decreasing the protein kinase activity.

Compounds which decrease the activity of VEGF are especially compounds which inhibit the VEGF receptor, especially the tyrosine kinase activity of the VEGF receptor, and compounds binding to VEGF, and are in particular those compounds, proteins and monoclonal antibodies generically and specifically disclosed in WO 98/35958 (describing compounds of formula I), WO 00/09495, WO 00/27820, WO 00/59509, WO 98/11223, WO 00/27819, WO 01/55114, WO 01/58899 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, vol. 27, no. 1, pp 14-21, 1999; in WO 00/37502 and WO 94/10202; Angiostatin™, described by M. S. O'Reilly et al, Cell 79, 1994, 315-328; and Endostatin™, described by M. S. O'Reilly et al, Cell 88, 1997, 277-285;

compounds which decrease the activity of EGF are especially compounds which inhibit the EGF receptor, especially the tyrosine kinase activity of the EGF receptor, and compounds binding to EGF, and are in particular those compounds generically and specifically disclosed in WO 97/02266 (describing compounds of formula IV), EP 0 564 409, WO 99/03854, EP 0520722, EP 0 566 226, EP 0 787 722, EP 0 837 063, WO 98/10767, WO 97/30034, WO 97/49688, WO 97/38983 and, especially, WO 96/33980;

compounds which decrease the activity of c-Src include, but are not limited to, compounds inhibiting the c-Src protein tyrosine kinase activity as defined below and to SH2 interaction inhibitors such as those disclosed in WO97/07131 and WO97/08193;

compounds inhibiting the c-Src protein tyrosine kinase activity include, but are not limited to, compounds belonging to the structure classes of pyrrolopyrimidines, especially pyrrolo[2,3-d]pyrimidines, purines, pyrazopyrimidines, especially pyrazo[3,4-d]pyrimidines, pyrazopyrimidines, especially pyrazo[3,4-d]pyrimidines and pyridopyrimidines, especially pyrido[2,3-d]pyrimidines. Preferably, the term relates to those compounds disclosed in WO 96/10028, WO 97/28161, WO97/32879 and WO97/49706;

anti-angiogenic compounds having another mechanism of action than decreasing the protein kinase activity include, but are not limited to e.g. thalidomide (THALOMID), SU5416, and celecoxib (Celebrex).

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, eg. as disclosed in U.S. Pat. No. 5,843,901.

The term "anti-androgens" as used herein includes, but is not limited to bicalutamide (CASODEX™), which can be formulated, e.g. as disclosed in U.S. Pat. No. 4,636,505.

The term "bengamides" relates to bengamides and derivatives thereof having aniproliferative properties and includes, but is not limited to the compounds generically and specifically disclosed in WO00/29382, preferably, to the compound disclosed in Example 1 of WO00/29382.

The term "bisphosphonates" as used herein includes, but is not limited to etridonic acid, clodronic acid, tiludronic acid, pamidronic acid, alendronic acid, ibandronic acid, risedronic acid and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g., in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g., in the form as it is marketed, e.g. under the trademark ZOMETA™.

"Trastuzumab" can be administered, e.g., in the form as it is marketed, e.g. under the trademark HERCEPTIN™.

For the treatment of AML, compounds of formula I can be used in combination with standard leukemia therapies, especially in combination with therapies used for the treatment of AML. In particular, compounds of formula I can be administered in combination with e.g. farnesyl-transferase inhibitors and/or other drugs used for the treatment of AML, such as Daunorubicin, Adriamycin, Ara-C, VP-16, Teniposide, Mitoxantrone, Idarubicin and Carboplatinum.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of formula I, can be prepared and administered as described in the art such as in the documents cited above.

EXAMPLES

The following Examples serve to illustrate the invention without limiting its scope.

Temperatures are measured in degrees Celsius. Unless otherwise indicated, the reactions take place at RT.

Analytical HPLC Conditions:

Grad 1: Linear gradient over 14 min of MeCN/0.1% TFA and $H_2O$/0.1% TFA from 1:4 to 1:0 and 5 min at 1:0, detection at 215 nm, flow rate 1.0 ml/min. Column: Nucleosil C18-column (250×4.6 mm, 5 µm, 100 Å).

Grad 2: Linear gradient over 7 min of MeCN/0.09% TFA and $H_2O$/0.1% TFA from 1:49 to 1:0 and 3 min at 1:0, detection at 215 nm, flow rate 2.0 ml/min. Column: Nucleosil C18-column (250×4.6 mm, 5 µm, 100 Å).

Shorty: Linear gradient over 5 min of MeCN/0.1% TFA and $H_2O$/0.1% TFA from 1:4 to 1:0 and 1 min at 1:0, detection at 215 nm, flow rate 1.0 ml/min. Column: Nucleosil C18-column (70×4 mm, 3 µm, 100 Å).

Grad25: isocratic over 25 min of MeCN/0.1% TFA and $H_2O$/0.1% TFA 1:1, detection at 215 nm, flow rate 1.0 m/min. Column: Nucleosil C18-column (250×4.6 mm, 5 µm, 100 Å).

The short forms and abbreviations used have the following definitions:
aqu. aqueous
ES-MS electron spray-mass spectroscopy
h hour(s)
Me methyl
min minute(s)
mp melting point
RT room temperature
TFA trifluoroacetic acid
THF tetrahydrofuran (distilled over Na/benzophenone)
$t_R$ retention times
V volume Example 1

To a solution of 3.84 g (7.25 mmol) of cis-2-{3-[4-amino-5-(3-benzyloxy-phenyl)-pyrrolo[2,3-d]pyrimidin-7-yl]-cyclobutylmethyl}-isoindole-1,3-dione in 100 ml of dry ethanol are added dropwise at RT and under argon 3.75 g (3.64 ml; 74.96 mmol) of hydrazine monohydrate. After 2 h most of the starting material is not yet dissolved, and additional 1.6 ml of hydrazine monohydrate are added thereto (total amount: 14.8 equivalents). The reaction is complete after 20 h. The colorless precipitate is filtered off, and washed with ethanol. The filtrate is evaporated to dryness and the crude compound is purified by chromatography on silicagel (dichloromethane:methanol:aqueous concentrated ammonia=90:10:1) to provide cis-7-(3-aminomethyl-cyclobutyl)-5-(3-benzyloxy-phenyl)-7H-pyrrolo[2,3-d]pyrimidin-4-ylamine. Analytical HPLC: $t_R$=7.47 min (Grad 1); ES-MS: m/e$_o$=400; $^1$H-NMR (CDCl$_3$): 8.31/s (1H); 7.3-7.5/m (6H); 7.12/s (1H); 7.05-7.08/2 peaks (2H); 6.99/m (1H); 5.17/m (1H); 5.14/s (2H); 5.04/broad s (2H); 2.87/d (2H); 2.75-2.65/m (2H); 2.2-2.1/m (2H); 1.55/broad s (2H).

Step 1.1: To a solution of 3.5 g (8.74 mmol) of cis-{3-[4-amino-5-(3-benzyloxy-phenyl)-pyrrolo[2,3-d]pyrimidin-7-yl]-cyclobutyl)methanol, which is prepared as described in Example 47(b) of WO 97/28161, in 70 ml of dry THF are added under argon 2.75 g (10.5 mmol) of triphenylphosphine and 1.54 g (10.5 mmol) of phthalimide; 1.9 g (1.71 ml; 10.5 mmol) of diethyl azodicarboxylate (96%) are added dropwise thereto. After stirring for 16 h at RT, the solution is concentrated to dryness and the crude compound is purified by flash-chromatography (ethylacetate) to provide cis-2-{3-[4-amino-5-(3-benzyloxy-phenyl)-pyrrolo[2,3-d]pyrimidin-7-yl]-cyclobutylmethyl}isoindole-1,3-dione. Analytical HPLC: $t_R$=11.96 min (Grad 1); ES-MS: m/e$_o$=529.9.

Example 2

To a solution of 4.15 g (7.83 mmol) of trans-2-{3-[4-amino-5-(3-benzyloxy-phenyl)-pyrrolo[2,3-d]pyrimidin-7-yl]-cyclobutylmethyl}-isoindole-1,3-dione in 100 ml of dry ethanol are added dropwise at RT and under argon 5.87 g (5.7 ml; 117.5 mmol) of hydrazine monohydrate. After 20 min all the starting material is dissolved, and the reaction is complete after 20 h stirring at RT. The colorless precipitate is filtered off, and washed with ethanol. The filtrate is evaporated to dryness and the crude compound is purified by chromatography on silica gel (dichloromethane:methanol: NH$_4$OH$_{aqu.}$=90:10:1) to provide trans-7-(3-aminomethyl-cyclobutyl)-5-(3-benzyloxy-phenyl)-7H-pyrrolo[2,3-d]pyrimidin-4-ylamine. Analytical HPLC: $t_R$=7.50 min (Grad 1); ES-MS: m/e$_o$=400; $^1$H-NMR (CDCl$_3$): 8.30/s (1H); 7.3-7.5/m (6H); 7.20/s (1H); 7.05-7.15/2 peaks (2H); 6.99/m (1H); 5.41/m (1H); 5.14/s (2H); 5.04/broad s (2H); 2.98/d (2H); 2.54-2.69/m (2H); 2.35-2.54/m (3H); 1.73/broad s (2H).

Step 2.1: To a solution of 5 g (12.48 mmol) of trans-{3-[4-amino-5-(3-benzyloxy-phenyl)pyrrolo[2,3-d]pyrimidin-7-yl]-cyclobutyl}-methanol, which is prepared as described in Example 47(b) of WO 97/28161, in 100 ml of dry THF are added under argon 4.91 g (18.72 mmol) of triphenylphosphine and 2.75 g (18.7 mmol) of phthalimide; 3.36 g (3.02 ml; 18.7 mmol) of diethyl azodicarboxylate (96%) are added dropwise thereto. The reaction mixture is stirred at RT for 27 h. The reaction mixture is concentrated to dryness and the crude compound is purified by flash-chromatography (ethylacetate) to obtain trans-2-{3-[4-amino-5-(3-benzyloxy-phenyl)-pyrrolo[2,3-d]pyrimidin-7-yl]-cyclobutylmethyl}-isoindole-1,3-dione. Analytical HPLC: $t_R$=12.12 min (Grad 1); ES-MS: m/e$_o$=529.9.

Example 3

To a solution of 45 mg (0.11 mmol) of cis-3-[4-amino-5-(3benzyloxy-phenyl)pyrrolo[2,3-d]pyrimidin-7-yl]-cyclobutanecarboxylic acid in 2 ml of N,N-dimethylformamide is added 36 mg (0.12 mmol) of O-(1,2-dihydro-2-oxo-1-pyridyl)-1,1,3,3-tetramethyluronium tetrafluoroborate and 39 µl (0.23 mmol) of diisopropylethylamine. 40 µl of a 5.6 M solution of dimethylamine are added thereto. After stirring the solution for 15 min at RT, working-up is effected by partitioning between water and ethyl acetate. The organic layer is dried over magnesium sulfate and concentrated in vacuo to provide cis-3-[4-amino-5-(3-benzyloxy-phenyl)pyrrolo[2,3-d]pyrimidin-7-yl]-cyclobutanecarboxylic acid dimethylamide. Analytical HPLC: $t_R$=6.81 min (Grad 2); ES-MS: m/e$_o$=442.0.

Step 3.1: The cis/trans-3-[4-amino-5-(3-benzyloxy-phenyl)-pyrrolo[2,3-d]pyrimidin-7-yl]-cyclobutanecarboxylic acid methyl ester mixture is prepared as described in Example 47(a) of WO 97/28161. The cis-3-[4-amino-5-(3-benzyloxy-phenyl)pyrrolo[2,3-d]pyrimidin-7-yl]-cyclobutanecarboxylic acid methyl ester is isolated from the cis/trans mixture by chromatography on silicagel (t-butyl-methyl-ether:ethylacetate=1:1). Analytical HPLC: $t_R$=10.59 min (Grad 1); ES-MS m/e$_o$=429.

Step 3.2: 0.1 g (0.23 mmol) of cis-3-[4-amino-5-(3-benzyloxy-phenyl)-pyrrolo[2,3-d]pyrimidin-7-yl]-cyclobutanecarboxylic acid methyl ester are dissolved in 1.8 ml of THF/1 M LiOH (1:1, v/v). After stirring at RT for 15 min, the pH of the solution is adjusted to pH=6 with 2N HCl and cis-3-[4-amino-5-(3-benzyloxy-phenyl)pyrrolo[2,3-d]pyrimidin-7-yl]-cyclobutanecarboxylic acid is obtained by filtering the suspension. Analytical HPLC: $t_R$=6.61 min (Grad 2); ES-MS: m/e$_o$=415.0.

Example 4 trans-3-[4-Amino-5-(3-benzyloxy-phenyl)-pyrrolo[2,3-d]pyrimidin-7-yl]-cyclobutanecarboxylic acid dimethylamide is obtained as described in Example 3 starting with trans-3-[4-amino-5-(3-benzyloxy-phenyl)-pyrrolo[2,3-d]pyrimidin-7-yl]-cyclobutanecarboxylic acid methyl ester [analytical HPLC: $t_R$=10.71 min (Grad 1); ES-MS m/e$_o$=429], which is separated from the cis/trans mixture (Example 47(a) of WO 97/28161) by chromatography on silicagel (t-butyl-methyl-ether:ethylacetate=1:1). Analytical HPLC: $t_R$=6.90 min (Grad 2); ES-MS: m/e$_o$=442.0.

Example 5 cis-3-[4-Amino-5-(3-benzyloxy-phenyl)-pyrrolo[2,3-d]pyrimidin-7-yl]-cyclobutanecarboxylic acid methylamide is obtained as described in Example 3 using a 8.03 M solution of methylamine in ethanol. Analytical HPLC: $t_R$=6.55 min (Grad 2); ES-MS: m/e$_o$=428.1.

Example 6 trans-3-[4-Amino-5-(3-benzyloxy-phenyl)-pyrrolo[2,3-d]pyrimidin-7-yl]-cyclobutanecarboxylic acid methylamide is obtained as described in Example 3 starting with trans-3-[4-amino-5-(3-benzyloxy-phenyl)pyrrolo[2,3-d]pyrimidin-7-yl]-cyclobutanecarboxylic acid and using a 8.03 M solution of methylamine in ethanol. Analytical HPLC: $t_R$=6.60 min (Grad 2); ES-MS: m/e$_o$=428.1.

Example 7

A solution of 42 mg (0.095 mmol) of cis-3-[4-amino-5-(3-benzyloxy-phenyl)pyrrolo[2,3-d]pyrimidin-7-yl]-cyclobutanecarboxylic acid dimethylamide in 2 ml of anhydrous THF is added dropwise at 0° C. to a 10 mg of lithium aluminium hydride suspended in 2 ml of anhydrous THF. The reaction mixture is slowly warmed to RT overnight. For working-up, the reaction mixture is cooled to 0° C. and then water and a 15% NaOH solution are added in succession thereto. The solution is partitioned between water and ethyl acetate. Drying the organic layer over magnesium sulfate, concentrating in vacuo and purifying by medium-pressure liquid chromatography yield cis-5-(3-benzyloxy-phenyl)-7-(3-dimethylaminomethyl-cyclobutyl)-7H-pyrrolo[2,3-d]pyrimidin-4-ylamine. Analytical HPLC: $t_R$=5.98 min (Grad 2); ES-MS: m/e$_o$=428.1.

Example 8 trans-5-(3-Benzyloxy-phenyl)-7-(3-dimethylaminomethyl-cyclobutyl)-7H-pyrrolo[2,3-d]pyrimidin-4-ylamine is prepared as described in Example 7 starting with trans-3-[4-amino-5-(3-benzyloxy-phenyl)-pyrrolo[2,3-d]pyrimidin-7-yl]-cyclobutanecarboxylic acid dimethylamide. Analytical HPLC: $t_R$=6.00 min (Grad 2); ES-MS: m/e$_o$=428.1.

Example 9 cis-5-(3-Benzyloxy-phenyl)-7-(3-methylaminomethyl-cyclobutyl)-7H-pyrrolo[2,3-d]pyrimidin-4-ylamine is prepared as described in Example 7 starting with cis-3-[4-amino-5-(3-benzyloxy-phenyl)-pyrrolo[2,3-d]pyrimidin-7-yl]-cyclobutanecarboxylic acid methylamide. Analytical HPLC: $t_R$=5.96 min (Grad 2); ES-MS: m/e$_o$=414.1.

Example 10 trans-5-(3-Benzyloxy-phenyl)-7-(3-methylaminomethyl-cyclobutyl)-7H-pyrrolo[2,3-d]pyrimidin-4-ylamine is prepared as described in Example 7 starting with trans-3-[4-amino-5-(3-benzyloxy-phenyl)-pyrrolo[2,3-d]pyrimidin-7-yl]-cyclobutanecarboxylic acid methylamide. Analytical HPLC: $t_R$=5.95 min (Grad 2); ES-MS: m/e$_o$=414.1.

Example 11

To a solution of 110 mg (0.275 mmol) of trans-7-(3-aminomethyl-cyclobutyl)-5-(3-benzyloxy-phenyl)-7H-pyrrolo[2,3-d]pyrimidin-4-ylamine in 5 ml of acetonitrile is added 72 mg (0.230 mmol) of N,N'-bis-tert-butoxycarbonyl-1-guanylpyrazole (Advanced ChemTech Europe, Machelen, Belgium). After 16 h at RT, the mixture is diluted with 50 ml of ethylacetate and washed with water. The aqueous phases are discarded and the organic layer is dried over magnesium sulfate and evaporated to dryness. The residue is dissolved in 5 ml of formic acid and the solution is stirred for 1 h at RT. The crude mixture is purified by medium-pressure liquid chromatography to provide trans-N-3-[4-amino-5-(3-benzyloxy-phenyl)pyrrolo[2,3-d]pyrimidin-7-yl]-cyclobutylmethyl}-guanidine. Analytical HPLC: $t_R$=6.12 min (Grad 2); ES-MS: m/e$_o$=442.0.

Example 12 cis-N-{3-[4-Amino-5-(3-benzyloxy-phenyl)-pyrrolo[2,3-d]pyrimidin-7-yl]-cyclobutylmethyl}-guanidine is prepared as described in Example 11 using cis-7-(3-aminomethyl-cyclobutyl)-5-(3-benzyloxy-phenyl)-7H-pyrrolo[2,3-d]pyrimidin-4-ylamine. Analytical HPLC: $t_R$=6.07 min (Grad 2); ES-MS: m/e$_o$=442.0.

Example 13

To a solution of 50 mg (0.125 mmol) of trans-7-(3-aminomethyl-cyclobutyl)-5-(3-benzyloxy-phenyl)-7H-pyrrolo[2,3-d]pyrimidin-4-ylamine in 2 ml of dry dichloromethane are added at 0° C. and under argon 10 μl (0.131 mmol) of methanesulfochloride and 44 μl (0.313 mmol) of triethylamine. After 20 h, working-up is effected by partitioning between water and dichloromethane. The crude product is purified by chromatography on silicagel (ethyl acetate:methanol=9:1) to yield trans-N-{3-[4-amino-5-(3-benzyloxy-phenyl)-pyrrolo[2,3-d]pyrimidin-7-yl]-cyclobutylmethyl}-methanesulfonamide. Analytical HPLC: $t_R$=9.66 min (Grad 1); ES-MS: m/e$_o$=478.0.

Example 14 cis-N-{3-[4-Amino-5-(3-benzyloxy-phenyl)-pyrrolo[2,3-d]pyrimidin-7-yl]-cyclobutylmethyl}-methanesulfonamide is prepared as described in Example 13 using cis-7-(3-aminomethyl-cyclobutyl)-5-(3-benzyloxy-phenyl)-7H-pyrrolo[2,3-d]pyrimidin-4-ylamine. Analytical HPLC: $t_R$=6.84 min (Grad 2); ES-MS: m/e$_o$=478.0.

Example 15 trans-N-{3-[4-Amino-5-(3-benzyloxy-phenyl)-pyrrolo[2,3-d]pyrimidin-7-yl]-cyclobutylmethyl}-4-methoxy-benzenesulfonamide is prepared as described in Example 13 using p-methoxyphenylsulfochloride. Analytical HPLC: $t_R$=11.1 min (Grad 1); ES-MS: m/e$_o$=569.9.

Example 16 trans-N-{3-[4-Amino-5-(3-benzyloxy-phenyl)-pyrrolo[2,3-d]pyrimidin-7-yl]-cyclobutylmethyl}-4-methyl-benzenesulfonamide is prepared as described In Example 13 using p-toluenesulfochloride. Analytical HPLC: $t_R$=11.44 min (Grad 1); ES-MS: m/e$_o$=554.

Example 17 trans-N-{3-[4-Amino-5-(3-benzyloxy-phenyl)-pyrrolo[2,3-d]pyrimidin-7-yl]-cyclobutylmethyl}-4-nitro-benzenesulfonamide is obtained as described in Example 13 using p-nitrophenylsulfochloride. Analytical HPLC: $t_R$=11.25 min (Grad 1); ES-MS: m/e$_o$=584.9.

Example 18

Propane-2-sulfonic acid trans-{3-[4-amino-5-(3-benzyloxy-phenyl)-pyrrolo[2,3-d]pyrimidin-7-yl]-cyclobutylmethyl}-amide is obtained as described in Example 13 using 2-propanesulfochloride. Analytical HPLC: $t_R$=11.14 min (Grad 1); ES-MS: m/e$_o$=505.9.

Example 19

Ethanesulfonic acid trans-{3-[4-amino-5-(3-benzyloxy-phenyl)-pyrrolo[2,3-d]pyrimidin-7-yl]-cyclobutyl}-amide is obtained as described in Example 13 using ethanesulfochloride. Analytical HPLC: $t_R$=10.77 min (Grad 1); ES-MS: m/e$_o$=492.0.

Example 20

N-dimethyl-sulfamide trans-{3-[4-amino-5-(3-benzyloxy-phenyl)-pyrrolo[2,3-d]pyrimidin-7-yl]-cyclobutylmethyl}-amide is prepared as described in Example 13 using dimethylsulfamoyl chloride (Fluka, Buchs, Switzerland). Analytical HPLC: $t_R$=7.18 min (Grad 2); ES-MS: m/e$_o$=506.9.

Example 21

N-dimethyl-sulfamide cis-{3-[4-amino-5-(3-benzyloxy-phenyl)-pyrrolo[2,3-d]pyrimidin-7-yl]-cyclobutylmethyl}-amide is prepared as described in Example 13 using cis-7-(3-aminomethyl-cyclobutyl)-5-(3-benzyloxy-phenyl)-7H-pyrrolo[2,3-d]pyrimidin-4-ylamine and dimethylsulfamoyl chloride (Fluka, Buchs, Switzerland). Analytical HPLC: $t_R$=7.15 min (Grad 2); ES-MS: m/e$_o$=506.9.

Example 22

To a solution of 50 mg (0.125 mmol) of trans-7-(3-aminomethyl-cyclobutyl)-5-(3-benzyloxy-phenyl)-7H-pyrrolo[2,3-d]pyrimidin-4-ylamine in 2 ml of dry dichloromethane are added at RT 12 μl (0.150 mmol) of methyl chloroformate (Fluka, Buchs, Switzerland) and 21 μl (0.150 mmol) of triethylamine. After stirring for 2 h at RT, working-up is effected by partitioning between water and ethyl acetate. The organic layer is dried over magnesium sulfate and concentrated in vacuo to provide trans-{3-[4-amino-5-(3-benzyloxy-phenyl)-pyrrolo[2,3-d]pyrimidin-7-yl]-cyclobutylmethyl}-carbamic acid methyl ester. Analytical HPLC: $t_R$=7.08 min (Grad 2); ES-MS: m/e$_o$=458.0.

Example 23 cis-{3-[4-Amino-5-(3-benzyloxy-phenyl)-pyrrolo[2,3-d]pyrimidin-7-yl]-cyclobutylmethyl}-carbamic acid methyl ester is prepared as described in Example 22 using cis-7-(3-aminomethyl-cyclobutyl)-5-(3-benzyloxy-phenyl)-7H-pyrrolo[2,3-d]pyrimidin-4-ylamine. Analytical HPLC: $t_R$=7.03 min (Grad 2); ES-MS: m/e$_o$=458.0.

Example 24 trans-{3-[4-Amino-5-(3-benzyloxy-phenyl)-pyrrolo[2,3-d]pyrimidin-7-yl]-cyclobutylmethyl}-carbamic acid 2-methoxy-ethyl ester is prepared as described in Example 22 using 2-methoxyethyl chloroformate (TCI America, Portland, Oreg., U.S.A.). Analytical HPLC: $t_R$=7.04 min (Grad 2); ES-MS: m/e$_o$=502.0.

Example 25 cis-{3-[4-Amino-5-(3-benzyloxy-phenyl)-pyrrolo[2,3-d]pyrimidin-7-yl]-cyclobutylmethyl}-carbamic acid 2-methoxy-ethyl ester is prepared as described in Example 22 using cis-7-(3-aminomethyl-cyclobutyl)-5-(3-benzyloxy-phenyl)-7H-pyrrolo[2,3-d]pyrimidin-4-ylamine and 2-methoxyethyl chloroformate (TCI America, Portland, Oreg., U.S.A.). Analytical HPLC: $t_R$=7.02 min (Grad 2); ES-MS: m/$e_o$=502.0.

Example 26

To a solution of 50 mg (0.125 mmol) of trans-7-(3-aminomethyl-cyclobutyl)-5-(3-benzyloxy-phenyl)-7H-pyrrolo[2,3-d]pyrimidin-4-ylamine in 4 ml of dry acetonitrile is added at RT 16 µl (0.2 mmol) of ethyl isocyanate (Fluka, Buchs, Switzerland). After stirring for 16 h at RT, working-up is effected by partitioning between water and ethyl acetate. The organic layer is dried over magnesium sulfate and evaporated to dryness to provide trans-1-{3-[4-amino-5-(3-benzyloxy-phenyl)-pyrrolo[2,3-d]pyrimidin-7-yl]-cyclobutylmethyl}-3-ethyl-urea. Analytical HPLC: $t_R$=6.77 min (Grad 2); ES-MS: m/$e_o$=471.1.

Example 27 cis-{3-[4-Amino-5-(3-benzyloxy-phenyl)pyrrolo[2,3-d]pyrimidin-7-yl]-cyclobutylmethyl}-3-ethyl-urea is prepared as described in Example 26 using cis-7-(3-aminomethyl-cyclobutyl)-5-(3-benzyloxy-phenyl)-7H-pyrrolo[2,3-d]pyrimidin-4-ylamine. Analytical HPLC: $t_R$=6.71 min (Grad 2); ES-MS: m/$e_o$=471.0.

Example 28 trans-1-{3-[4-Amino-5-(3-benzyloxy-phenyl)-pyrrolo[2,3-d]pyrimidin-7-yl]-cyclobutylmethyl}-3-propyl-urea is prepared as described in Example 26 using n-propyl isocyanate (Fluka, Buchs, Switzerland). Analytical HPLC: $t_R$=6.39 min (Grad 2); ES-MS: m/$e_o$ =485.0.

Example 29 cis-1-{3-[4-Amino-5-(3-benzyloxy-phenyl)pyrrolo[2,3-d]pyrimidin-7-yl]-cyclobutylmethyl}3-propyl-urea is prepared as described in Example 26 using cis-7-(3-aminomethyl-cyclobutyl)-5-(3-benzyloxy-phenyl)-7H-pyrrolo[2,3-d]pyrimidin-4-ylamine and n-propyl isocyanate (Fluka, Buchs, Switzerland). Analytical HPLC: $t_R$=6.33 min (Grad 2); ES-MS: m/$e_o$=484.9.

Example 30 trans-1-{3-[4-Amino-5-(3-benzyloxy-phenyl)pyrrolo[2,3-d]pyrimidin-7-yl]-cyclobutylmethyl}-3-isopropyl-urea is prepared as described in Example 26 using 2-propylisocyanate (Fluka, Buchs, Switzerland). Analytical HPLC: $t_R$=6.28 min (Grad 2); ES-MS: m/$e_o$=485.0.

Example 31 cis-1-{3-[4-Amino-5-(3-benzyloxy-phenyl)-pyrrolo[2,3-d]pyrimidin-7-yl]-cyclobutylmethyl}-3-isopropyl-urea is prepared as described in Example 26 using cis-7-(3-aminomethyl-cyclobutyl)-5-(3-benzyloxy-phenyl)-7H-pyrrolo[2,3-d]pyrimidin-4-ylamine and 2-propylisocyanate (Fluka, Buchs, Switzerland). Analytical HPLC: $t_R$=6.37 min (Grad 2); ES-MS: m/$e_o$=484.9.

Example 32 trans-1-{3-[4-Amino-5-(3-benzyloxy-phenyl)-pyrrolo[2,3-d]pyrimidin-7-yl]-cyclobutylmethyl}-3-butyl-urea is prepared as described in Example 26 using n-butyl isocyanate (Fluka, Buchs, Switzerland). Analytical HPLC: $t_R$=6.53 min (Grad 2); ES-MS: m/$e_o$=499.0.

Example 33 cis-1-{3-[4-Amino-5-(3-benzyloxy-phenyl)-pyrrolo[2,3-d]pyrimidin-7-yl]-cyclobutylmethyl}-3-butyl-urea is prepared as described in Example 26 using cis-7-(3-aminomethyl-cyclobutyl)-5-(3-benzyloxy-phenyl)-7H-pyrrolo[2,3-d]pyrimidin-4-ylamine and n-butyl isocyanate (Fluka, Buchs, Switzerland). Analytical HPLC: $t_R$=6.54 min (Grad 2); ES-MS: m/$e_o$=499.0.

Example 34 trans-1-{3-[4-Amino-5-(3-benzyloxy-phenyl)-pyrrolo[2,3-d]pyrimidin-7-yl]-cyclobutylmethyl}-3-tert-butyl-urea is prepared as described in Example 26 using tert-butyl isocyanate (Fluka, Buchs, Switzerland). Analytical HPLC: $t_R$=6.60 min (Grad 2); ES-MS: m/$e_o$=499.0.

Example 35 cis-1-{3-[4-Amino-5-(3-benzyloxy-phenyl)-pyrrolo[2,3-d]pyrimidin-7-yl]-cyclobutylmethyl}-3-tert-butyl-urea is prepared as described in Example 26 using cis-7-(3-aminomethyl-cyclobutyl)-5-(3-benzyloxy-phenyl)-7H-pyrrolo[2,3-d]pyrimidin-4-ylamine and tert-butyl isocyanate (Fluka, Buchs, Switzerland). Analytical HPLC: $t_R$=6.61 min (Grad 2); ES-MS: m/$e_o$=499.0.

Example 36 trans-1-{3-[4-Amino-5-(3-benzyloxy-phenyl)-pyrrolo[2,3-d]pyrimidin-7-yl]-cyclobutylmethyl}-3-benzyl-urea is prepared as described in Example 26 using benzyl isocyanate (Fluka, Buchs, Switzerland). Analytical HPLC: $t_R$=6.88 min (Grad 2); ES-MS: m/$e_o$=532.9.

Example 37 trans-1-{3-[4-Amino-5-(3-benzyloxy-phenyl)-pyrrolo[2,3-d]pyrimidin-7-yl]-cyclobutylmethyl}-3-(3-methyl-benzyl)-urea is prepared as described in Example 26 using 3-methylbenzyl isocyanate (Aldrich, Buchs, Switzerland). Analytical HPLC: $t_R$=7.50 min (Grad 2); ES-MS: m/$e_o$=546.9.

Example 38 cis-1-{3-[4-Amino-5-(3-benzyloxy-phenyl)-pyrrolo[2,3-d]pyrimidin-7-yl]-cyclobutylmethyl}-3-(3-methyl-benzyl)-urea is prepared as described in Example 26 using cis-7-(3-aminomethyl-cyclobutyl)-5-(3-benzyloxy-phenyl)-7H-pyrrolo[2,3-d]pyrimidin-4-ylamine and 3-methylbenzyl isocyanate (Aldrich, Buchs, Switzerland). Analytical HPLC: $t_R$=7.45 min (Grad 2); ES-MS: m/$e_o$=546.9.

Example 39 cis-1-{3-[4-Amino-5-(3-benzyloxy-phenyl)-pyrrolo[2,3-d]pyrimidin-7-yl]-cyclobutylmethyl}-3-(4-methoxy-benzyl)-urea is prepared as described in Example 26 using cis-7-(3-aminomethyl-cyclobutyl)-5-(3-benzyloxy-phenyl)-7H-pyrrolo[2,3-d]pyrimidin-4-ylamine and 4-methoxybenzyl isocyanate (Aldrich, Buchs, Switzerland). Analytical HPLC: $t_R$=7.21 min (Grad 2); ES-MS: m/$e_o$=562.9.

Example 40

To a solution of 41 mg (0.075 mmol) of trans-{3-[4-amino-5-(3-benzyloxy-phenyl)-pyrrolo[2,3-d]pyrimidin-7-yl]-cyclobutylmethyl}-3-(2-bromo-ethyl)-urea, which is prepared as described in Example 26 using 2-bromoethyl isocyanate (Aldrich, Buchs, Switzerland), in 5 ml of ethanol is added 33 μl (0.375 mmol) of morpholine. The mixture is refluxed for 3 h and the crude mixture is purified by medium-pressure liquid chromatography to provide trans-1-{3-[4-amino-5-(3-benzyloxy-phenyl)-pyrrolo[2,3-d]pyrimidin-7-yl]-cyclobutylmethyl}-3-(2-morpholin-4-yl-ethyl)-urea. Analytical HPLC: $t_R$=6.12 min (Grad 2); ES-MS: m/e$_o$=555.9.

Example 41 cis-1-{3-[4-Amino-5-(3-benzyloxy-phenyl)-pyrrolo[2,3-d]pyrimidin-7-yl]-cyclobutylmethyl}-3-(2-morpholin-4-yl-ethyl)-urea is prepared as described in Example 40 using cis-7-(3-aminomethyl-cyclobutyl)-5-(3-benzyloxy-phenyl)-7H-pyrrolo[2,3-d]pyrimidin-4-ylamine as starting material. Analytical HPLC: $t_R$=6.04 min (Grad 2); ES-MS: m/e$_o$=555.9.

Example 42 trans-1-{3-[4-Amino-5-(3-benzyloxy-phenyl)-pyrrolo[2,3-d]pyrimidin-7-yl]-cyclobutylmethyl}-3-(2-dimethylamino-ethyl)-urea is prepared as described in Example 40 using dimethylamine (5.6 M solution in ethanol; Fluka, Buchs, Switzerland). Analytical HPLC: $t_R$=6.08 min (Grad 2); ES-MS: m/e$_o$=514.0.

Example 43 cis-1-{3-[4-Amino-5-(3-benzyloxy-phenyl)-pyrrolo[2,3-d]pyrimidin-7-yl]-cyclobutylmethyl}-3-(2-dimethylamino-ethyl)-urea is prepared as described in Example 40 using cis-7-(3-aminomethyl-cyclobutyl)-5-(3-benzyloxy-phenyl)-7H-pyrrolo[2,3-d]pyrimidin-4-ylamine as starting material and dimethylamine (5.6 M solution in ethanol; Fluka, Buchs, Switzerland). Analytical HPLC: $t_R$=5.98 min (Grad 2); ES-MS: m/e$_o$=514.0.

Example 44 trans-1-{3-[4-Amino-5-(3-benzyloxy-phenyl)-pyrrolo[2,3-d]pyrimidin-7-yl]-cyclobutylmethyl}-3-(3-morpholin-4-yl-propyl)-urea is prepared as described in Example 40 using 3-chloropropyl isocyanate (Aldrich, Buchs, Switzerland). Analytical HPLC: $t_R$=6.12 min (Grad 2); ES-MS: m/e$_o$=569.9.

Example 45 cis-1-{3-[4-Amino-5-(3-benzyloxy-phenyl)-pyrrolo[2,3-d]pyrimidin-7-yl]-cyclobutylmethyl}-3-(3-morpholin-4-yl-propyl)-urea is prepared as described in Example 40 using cis-7-(3-aminomethyl-cyclobutyl)-5-(3-benzyloxy-phenyl)-7H-pyrrolo[2,3-d]pyrimidin-4-ylamine and 3-chloropropyl isocyanate. Analytical HPLC: $t_R$=5.93 min (Grad 2); ES-MS: m/e$_o$=570.0.

Example 46 trans-1-{3-[4-Amino-5-(3-benzyloxy-phenyl)-pyrrolo[2,3-d]pyrimidin-7-yl]-cyclobutylmethyl}-3-(3-dimethylamino-propyl)-urea is prepared as described in Example 40 using 3-chloropropyl isocyanate and dimethylamine. Analytical HPLC: $t_R$=6.09 min (Grad 2); ES-MS: m/e$_o$=528.0.

Example 47 cis-1-{3-[4-Amino-5-(3-benzyloxy-phenyl)-pyrrolo[2,3-d]pyrimidin-7-yl]-cyclobutylmethyl}-3-(3-dimethylamino-propyl)-urea is prepared as described in Example 40 using cis-7-(3-aminomethyl-cyclobutyl)-5-(3-benzyloxy-phenyl)-7H-pyrrolo[2,3-]pyrimidin-4-ylamine, 3-chloropropyl isocyanate and dimethylamine. Analytical HPLC: $t_R$=5.95 min (Grad 2); ES-MS: m/e$_o$=528.0.

Example 48

To a solution of 50 mg (0.125 mmol) of trans-7-(3-aminomethyl-cyclobutyl)-5-(3-benzyloxy-phenyl)-7H-pyrrolo[2,3-d]pyrimidin-4-ylamine in 5 ml of methanol is added 45 mg (0.561 mmol) of potassium cyanate (Aldrich, Buchs, Switzerland). The mixture is refluxed for one week. After concentration to dryness, the residue is purified by flash-chromatography (dichloromethane:methanol=9:1) to provide trans-{3-[4-amino-5-(3-benzyloxy-phenyl)-pyrrolo[2,3-d]pyrimidin-7-yl]-cyclobutylmethyl}-urea. Analytical HPLC: $t_R$=6.43 min (Grad 2); ES-MS: m/e$_o$=443.0.

Example 49 cis-{3-[4-Amino-5-(3-benzyloxy-phenyl)-pyrrolo[2,3-d]pyrimidin-7-yl]-cyclobutylmethyl}-urea is prepared as described in Example 48 using cis-7-(3-aminomethyl-cyclobutyl)-5-(3-benzyloxy-phenyl)-7H-pyrrolo[2,3-d]pyrimidin-4-ylamine. Analytical HPLC: $t_R$=6.37 min (Grad 2); ES-MS: m/e$_o$=442.9.

Example 50

To a solution of 50 mg (0.125 mmol) of trans-7-(3-aminomethyl-cyclobutyl)-5-(3-benzyloxy-phenyl)-7H-pyrrolo[2,3-d]pyrimidin-4-ylamine in 2 ml of anhydrous N,N-dimethylformamide is added 13 μl (0.138 mmol) of acetic anhydride (Fluka, Buchs, Switzerland). After stirring 1 h at RT, working-up is effected by partitioning between water and ethyl acetate. The organic layer is dried over magnesium sulfate and evaporated to dryness to provide trans-N-{3-[4-amino-5-(3-benzyloxy-phenyl)-pyrrolo[2,3-d]pyrimidin-7-yl]-cyclobutylmethyl}-acetamide. Analytical HPLC: $t_R$=6.65 min (Grad 2); ES-MS: m/e$_o$=442.0.

Example 51 cis-N-{3-[4-Amino-5-(3-benzyloxy-phenyl)-pyrrolo[2,3-d]pyrimidin-7-yl]-cyclobutylmethyl}-acetamide is prepared as described in Example 50 using cis-7-(3-aminomethyl-cyclobutyl)-5-(3-benzyloxy-phenyl)-7H-pyrrolo[2,3-d]pyrimidin-4-ylamine. Analytical HPLC: $t_R$=6.59 min (Grad 2); ES-MS: m/e$_o$=442.0.

Example 52 trans-N-{3-[4-Amino-5-(3-benzyloxy-phenyl)-pyrrolo[2,3-d]pyrimidin-7-yl]-cyclobutylmethyl}-isobutyramide is prepared as described in Example 50 using isobutyril chloride (Fluka, Buchs, Switzerland). Analytical HPLC: $t_R$=7.00 min (Grad 2); ES-MS: m/$e_o$=470.0.

Example 53 cis-N-{3-[4-Amino-5-(3-benzyloxy-phenyl)-pyrrolo[2,3-d]pyrimidin-7-yl]-cyclobutylmethyl}-isobutyramide is prepared as described in Example 50 using cis-7-(3-aminomethyl-cyclobutyl)-5-(3-benzyloxy-phenyl)-7H-pyrrolo[2,3-d]pyrimidin-4-ylamine and isobutyril chloride (Fluka, Buchs, Switzerland). Analytical HPLC: $t_R$=6.95 min (Grad 2); ES-MS: m/$e_o$=470.0.

Example 54 trans-N-{3-[4-Amino-5-(3-benzyloxy-phenyl)-pyrrolo[2,3-d]pyrimidin-7-yl]-cyclobutylmethyl}-2,2-dimethyl-propionamide is prepared as described in Example 50 using pivaloyl chloride (Fluka, Buchs, Switzerland). Analytical HPLC: $t_R$=7.30 min (Grad 2); ES-MS: m/$e_o$=484.0.

Example 55 cis-N-{3-[4-Amino-5-(3-benzyloxy-phenyl)-pyrrolo[2,3-d]pyrimidin-7-yl]-cyclobutylmethyl}-2,2-dimethyl-propionamide is prepared as described in Example 50 using cis-7-(3-aminomethyl-cyclobutyl)-5-(3-benzyloxy-phenyl)-7H-pyrrolo[2,3-d]pyrimidin-4-ylamine and pivaloyl chloride (Fluka, Buchs, Switzerland). Analytical HPLC: $t_R$=7.25 min (Grad 2); ES-MS: m/$e_o$=484.0.

Example 56

48 mg (0.1 mmol) of trans-N-{3-[4-amino-5-(3-benzyloxy-phenyl)-pyrrolo[2,3-d]-pyrimidin-7-yl]-cyclobutylmethyl}-2-chloro-acetamide and 25 µl (0.3 mmol) of piperidine in 5 ml of ethanol are refluxed for 2 h. trans-N-{3-[4-amino-5-(3-benzyloxy-phenyl)-pyrrolo[2,3-d]-pyrimidin-7-yl]-cyclobutylmethyl}-2-piperidin-1-yl-acetamide is obtained after purification of the crude mixture by medium-pressure liquid chromatography. Analytical HPLC: $t_R$=6.17 min (Grad 2); ES-MS: m/$e_o$=525.0.

Step 56.1: To a suspension of 210 mg (0.53 mmol) of trans-7-(3-aminomethyl-cyclobutyl)-5-(3-benzyloxy-phenyl)-7H-pyrrolo[2,3-d]pyrimidin-4-ylamine in 10 ml of acetonitrile is added 49 µl (0.61 mmol) of chloro-acetyl chloride (Fluka, Buchs, Switzerland) and 85 µl (0.61 mmol) of triethylamine. The solution is stirred for 5 h at RT. trans-N-{3-[4-amino-5-(3-benzyloxy-phenyl)-pyrrolo[2,3-d]pyrimidin-7-yl]-cyclobutylmethyl}-2-chloro-acetamide is obtained after purification of the crude mixture by medium-pressure liquid chromatography. Analytical HPLC: $t_R$=6.94 min (Grad 2); ES-MS: m/$e_o$=476.0.

Example 57 cis-N-{3-[4-Amino-5-(3-benzyloxy-phenyl)-pyrrolo[2,3-d]pyrimidin-7-yl]-cyclobutylmethyl}-2-piperidin-1-yl-acetamide is obtained as described in Example 56 starting with cis-7-(3-aminomethyl-cyclobutyl)-5-(3-benzyloxy-phenyl)-7H-pyrrolo[2,3-d]pyrimidin-4-ylamine. Analytical HPLC: $t_R$=6.14 min (Grad 2); ES-MS: m/$e_o$=525.0.

Example 58 trans-N-{3-[4-Amino-5-(3-benzyloxy-phenyl)-pyrrolo[2,3-d]pyrimidin-7-yl]-cyclobutylmethyl}-2-morpholin-4-yl-acetamide is obtained as described in Example 56 using morpholine. Analytical HPLC: $t_R$=6.03 min (Grad 2); ES-MS: m/$e_o$=526.9.

Example 59 cis-N-{3-[4-Amino-5-(3-benzyloxy-phenyl)-pyrrolo[2,3-d]pyrimidin-7-yl]-cyclobutylmethyl}-2-morpholin-4-yl-acetamide is obtained as described in Example 56 starting with cis-7-(3-aminomethyl-cyclobutyl)-5-(3-benzyloxy-phenyl)-7H-pyrrolo[2,3-d]pyrimidin-4-ylamine and using morpholine. Analytical HPLC: $t_R$=5.98 min (Grad 2); ES-MS: m/$e_o$=527.0.

Example 60 trans-N-{3-[4-Amino-5-(3-benzyloxy-phenyl)-pyrrolo[2,3-d]pyrimidin-7-yl]-cyclobutylmethyl}-2-(4-methyl-piperazin-1-yl)-acetamide is obtained as described in Example 56 using 1-methyl-piperazine. Analytical HPLC: $t_R$=5.87 min (Grad 2); ES-MS: m/$e_o$=539.9.

Example 61 cis-N-{3-[4-Amino-5-(3-benzyloxy-phenyl)-pyrrolo[2,3-d]pyrimidin-7-yl]-cyclobutylmethyl}-2-(4-methyl-piperazin-1-yl)-acetamide is obtained as described in Example 56 starting with cis-7-(3-aminomethyl-cyclobutyl)-5-(3-benzyloxy-phenyl)-7H-pyrrolo[2,3-d]pyrimidin-4-ylamine and using 1-methyl-piperazine. Analytical HPLC: $t_R$=5.83 min (Grad 2); ES-MS: m/$e_o$=539.9.

Example 62

A solution of 50 mg (0.09 mmol) of trans-toluene-4-sulfonic acid 3-[4-amino-5-(3-benzyloxy-phenyl)-pyrrolo[2,3-d]pyrimidin-7-yl]-cyclobutylmethyl ester in 1 ml of morpholine (Fluka, Buchs, Switzerland) is stirred at RT for 72 h. The solvent is evaporated to dryness and the residue is purified by flash-chromatography (ethylacetate:methanol:$NH_4OH_{aqu.}$=95:5:1) to provide trans-5-(3-benzyloxy-phenyl)-7-(3-morpholin-4-ylmethyl-cyclobutyl)-7H-pyrrolo[2,3-d]pyrimidin-4-ylamine. Analytical HPLC: $t_R$=9.29 min (Grad 1); ES-MS: m/$e_o$=470.0.

Step 62.1: 200 mg (0.49 mmol) of trans-3-[4-amino-5-(3-benzyloxy-phenyl)-pyrrolo[2,3-d]pyrimidin-7-yl]-cyclobutyl)methanol, which is prepared as described In Example 47(b) of WO 97/28161, are dissolved in 2 ml of pyridine and the solution is cooled to −20° C. 153 mg (0.8 mmol) of p-toluenesulfonyl chloride are added to this solution and the reaction mixture is left overnight in the freezer at −20° C. Then, 10 ml of ice-cold water are added and the mixture is extracted with cold dichloromethane. The aqueous phase is discarded and the organic phase is washed with cold water/2N $H_2SO_4$ and water. The organic layer is dried over magnesium sulfate and evaporated to dryness to provide trans-toluene-4-sulfonic acid 3-[4-amino-5-(3-benzyloxy-phenyl)-pyrrolo[2,3-d]pyrimidin-7-yl]-cyclobutylmethyl ester, which was used in the next step without further purification. Analytical HPLC: $t_R$=13.09 min (Grad 1); ES-MS: m/$e_o$=554.9.

Example 63 trans-5-(3-Benzyloxy-phenyl)-7-(3-piperidin-1-ylmethyl-cyclobutyl)-7H-pyrrolo[2,3-d]pyrimidin-4-ylamine is prepared as described in Example 62 using piperidine (Fluka, Buchs, Switzerland). Analytical HPLC: $t_R$=9.93 min (Grad 1); ES-MS: m/e$_o$=468.0.

Example 64 trans-5-(3-Benzyloxy-phenyl)-7-(3-pyrrolidin-1-ylmethyl-cyclobutyl)-7H-pyrrolo[2,3-d]pyrimidin-4-ylamine is prepared as described in Example 62 using pyrrolidine (Fluka, Buchs, Switzerland). Analytical HPLC: $t_R$=9.59 min (Grad 1); ES-MS: m/e$_o$=454.0.

Example 65 trans-5-(3-Benzyloxy-phenyl)-7-[3-(4-methyl-piperazin-1-ylmethyl)-cyclobutyl]-7H-pyrrolo[2,3-d]pyrimidin-4-ylamine is prepared as described in Example 62 using 1-methyl-piperazine (Fluka, Buchs, Switzerland). Analytical HPLC: $t_R$=5.68 min (Grad 2); ES-MS: m/e$_o$=483.3.

Example 66

50 mg (0.09 mmol) of trans-toluene-4-sulfonic acid 3-[4-amino-5-(3-benzyloxy-phenyl)-pyrrolo[2,3-d]pyrimidin-7-yl]-cyclobutylmethyl ester and 34 mg (0.225 mmol) of adamantan-1-ylamine (Fluka, Buchs, Switzerland) in 1 ml N,N-dimethylformamide are stirred for 18 h at RT and for 24 h at 60° C. Additional adamantan-1-ylamine is added (34 mg) and stirring is continued for 24 h at 120° C. The solvent is evaporated to dryness and the residue is purified by flash-chromatography (ethylacetate:methanol: NH$_4$OH$_{aqu.}$=95:5:1) to provide trans-7-[3-(adamantan-1-ylaminomethyl)cyclobutyl]-5-(3-benzyloxy-phenyl)-7H-pyrrolo[2,3-d]pyrimidin-4-ylamine. Analytical HPLC: $t_R$=11.14 min (Grad 1); ES-MS: m/e$_o$=533.9.

Example 67 trans-1-{3-[4-Amino-5-(3-benzyloxy-phenyl)-pyrrolo[2,3-d]pyrimidin-7-yl]-cyclobutylmethyl}-piperidin-4-ol is prepared as described in Example 62 using 4-hydroxypiperidine (Fluka, Buchs, Switzerland). Analytical HPLC: $t_R$=8.52 min (Grad 1); ES-MS: m/e$_o$=484.2.

Example 68 trans-7-(3-Azepan-1-ylmethyl-cyclobutyl)-5-(3-benzyloxy-phenyl)-7H-pyrrolo[2,3-d]pyrimidin-4-ylamine is prepared as described in Example 62 using hexamethyl-eneimine (Fluka, Buchs, Switzerland). Analytical HPLC: $t_R$=9.49 min (Grad 1); ES-MS: ml/e$_o$=482.3.

Example 69 trans-5-(3-Benzyloxy-phenyl)-7-[3-(2,5-dimethyl-pyrrolidin-1-ylmethyl)-cyclobutyl]-7H-pyrrolo[2,3-d]pyrimidin-4-ylamine is prepared as described in Example 62 using 2,5-dimethylpyrrolidine (cis/trans) (Brunswig Chemie, Basel, Switzerland). Analytical HPLC: $t_R$=9.38 min (Grad 1); ES-MS: m/e$_o$=482.2.

Example 70 trans-7-(3-Azetidin-1-ylmethyl-cyclobutyl)-5-(3-benzyloxy-phenyl)-7H-pyrrolo[2,3-d]pyrimidin-4-ylamine is prepared as described in Example 62 using trimethyleneimine (Fluka, Buchs, Switzerland). Analytical HPLC: $t_R$=8.89 min (Grad 1); ES-MS: m/e$_o$=440.2.

Example 71 trans-1-{3-[4-Amino-5-(3-benzyloxy-phenyl)-pyrrolo[2,3-d]pyrimidin-7-yl]-cyclobutylmethyl}-piperidine-3-carboxylic acid amide is prepared as described in Example 62 using R,S-nipecotamide (Aldrich, Buchs, Switzerland). Analytical HPLC: $t_R$=8.52 min (Grad 1); ES-MS: m/e$_o$=511.0.

Example 72 trans-5-(3-Benzyloxy-phenyl)-7-[3-(4-pyridin-2-yl-piperazin-1-ylmethyl)-cyclobutyl]-7H-pyrrolo[2,3-d]pyrimidin-4-ylamine is prepared as described in Example 62 using 1-(2-pyridyl)-piperazine (Aldrich, Buchs, Switzerland). Analytical HPLC: $t_R$=8.15 min (Grad 1); ES-MS: m/e$_o$=546.2.

Example 73 trans-5-(3-Benzyloxy-phenyl)-7-(3-thiomorpholin-4-ylmethyl-cyclobutyl)-7H-pyrrolo[2,3-d]pyrimidin-4-ylamine is prepared as described in Example 62 using thiomorpholine (Fluka, Buchs, Switzerland). Analytical HPLC: $t_R$=9.26 min (Grad 1); ES-MS: m/e$_o$=486.2.

Example 74 trans-5-(3-Benzyloxy-phenyl)-7-[3-(2,6-dimethyl-morpholin-4-ylmethyl)-cyclobutyl]-7H-pyrrolo[2,3-d]pyrimidin-4-ylamine is prepared as described in Example 62 using cis/trans-2,6-dimethylmorpholine (Fluka, Buchs, Switzerland). Analytical HPLC: $t_R$=9.39 min (Grad 1); ES-MS: m/e$_o$=498.2.

Example 75 trans-(S)1-{3-[4-Amino-5-(3-benzyloxy-phenyl)-pyrrolo[2,3-d]pyrimidin-7-yl]-cyclobutylmethyl}-pyrrolidine-2-carboxylic acid amide is prepared as described in Example 62 using L-prolinamide (Aldrich, Buchs, Switzerland). Analytical HPLC: $t_R$=8.56 min (Grad 1); ES-MS: m/e$_o$=497.2.

Example 76 cis-7-(3-Azepan-1-ylmethyl-cyclobutyl-5-(3-benzyloxyphenyl)-7H-pyrrolo[2,3-d]pyrimidin-4-ylamine is prepared as described in Example 62 using cis-{3-[4-amino-5-(3-benzyloxy-phenyl)-pyrrolo[2,3-d]pyrimidin-7-yl]-cyclobutyl)methanol, which is prepared as described in Example 47(b) of WO 97/28161, as starting material and hexamethyleneimine (Fluka, Buchs, Switzerland). Analytical HPLC: $t_R$=9.51 min (Grad 1); ES-MS: m/e$_o$=482.2.

Example 77 cis-1-{3-[4-Amino-5-(3-benzyloxy-phenyl)-pyrrolo[2,3-d]pyrimidin-7-yl]-cyclobutylmethyl}-piperidin-4-ol is prepared as described in Example 76 using 4-hydroxypiperidine (Fluka, Buchs, Switzerland). Analytical HPLC: $t_R$=8.36 min (Grad 1); ES-MS: m/e$_o$=484.2.

Example 78 cis-4-{3-[4-Amino-5-(3-benzyloxy-phenyl)-pyrrolo[2,3-d]pyrimidin-7-yl]-cyclobutylmethyl}piperazine-1-carboxylic acid ethyl ester is prepared as described in Example 76 using 1-ethoxycarbonylpiperazine (Fluka, Buchs, Switzerland). Analytical HPLC: $t_R$=9.23 min (Grad 1); ES-MS: $m/e_o$=541.2.

Example 79 cis-5-(3-Benzyloxy-phenyl)-7-[3-(4-phenyl-piperazin-1-ylmethyl)-cyclobutyl]-7H-pyrrolo[2,3-d]pyrimidin-4-ylamine is prepared as described in Example 76 using 1-phenylpiperazine (Fluka, Buchs, Switzerland). Analytical HPLC: $t_R$=10.24 min (Grad 1); ES-MS: $m/e_o$=545.1.

Example 80 cis-5-(3-Benzyloxy-phenyl)-7-[3-(4-methyl-piperazin-1-ylmethyl)-cyclobutyl]-7H-pyrrolo[2,3-d]pyrimidin-4-ylamine is prepared as described in Example 76 using 1-methylpiperazine (Fluka, Buchs, Switzerland). Analytical HPLC: $t_R$=7.87 min (Grad 1); ES-MS: $m/e_o$=483.2.

Example 81 cis-5-(3-Benzyloxy-phenyl)-7-(3-thiomorpholin-4-ylmethyl-cyclobutyl)-7H-pyrrolo[2,3-d]pyrimidin-4-ylamine is prepared as described in Example 76 using thiomorpholine (Fluka, Buchs, Switzerland). Analytical HPLC: $t_R$=9.08 min (Grad 1); ES-MS: $m/e_o$=486.1.

Example 82 cis-5-(3-Benzyloxy-phenyl)-7-[3-(2,6-dimethyl-morpholin-4-ylmethyl)-cyclobutyl]-7H-pyrrolo[2,3-d]pyrimidin-4-ylamine is prepared as described in Example 76 using cis/trans-2,6-dimethylmorpholine (Fluka, Buchs, Switzerland). Analytical HPLC: $t_R$=9.27 min (Grad 1); ES-MS: $m/e_o$=498.2.

Example 83 cis-(R)-1-{3-[4-Amino-5-(3-benzyloxy-phenyl)-pyrrolo[2,3-d]pyrimidin-7-yl]-cyclobutylmethyl}-pyrrolidine-2-carboxylic acid amide is prepared as described in Example 76 using L-prolinamide (Aldrich, Buchs, Switzerland). Analytical HPLC: $t_R$=8.53 min (Grad 1); ES-MS: $m/e_o$=497.1.

Example 84 cis-1-(3-[4-Amino-5-(3-benzyloxy-phenyl)-pyrrolo[2,3-d]pyrimidin-7-yl]-cyclobutylmethyl}-piperidine-3-carboxylic acid amide is prepared as described in Example 76 using L,D-nipecotamide (Aldrich, Buchs, Switzerland). Analytical HPLC: $t_R$=8.46 min (Grad 1); ES-MS: $m/e_o$=511.2.

Example 85 trans-N-{3-[4-Amino-5-(3-benzyloxy-phenyl)-pyrrolo[2,3-d]pyrimidin-7-yl]-cyclobutylmethyl}-2-ethoxy-acetamide is prepared starting from trans-7-(3-aminomethyl-cyclobutyl)-5-(3-benzyloxy-phenyl)-7H-pyrrolo[2,3-d]pyrimidin-4-ylamine and ethoxy-acetic acid (Fluka, Buchs, Switzerland) according to a procedure known in the art (M. Bodanszky in Principles of Peptide Synthesis, Akad.-Verlag, 1984). Analytical HPLC: $t_R$=7.07 min (Grad 2); ES-MS: $m/e_o$=486.2.

Example 86 trans-N-{3-[4-Amino-5-(3-benzyloxy-phenyl)-pyrrolo[2,3-d]pyrimidin-7-yl]-cyclobutylmethyl}-2-(2-methoxyethoxy)acetamide is prepared starting from trans-7-(3-aminomethyl-cyclobutyl)-5-(3-benzyloxy-phenyl)-7H-pyrrolo[2,3-d]pyrimidin-4-ylamine and 2-(2-methoxyethoxy)-acetic acid (Fluka, Buchs, Switzerland) according to a procedure known in the art (M. Bodanszky in Principles of Peptide Synthesis, Akad.-Verlag, 1984). Analytical HPLC: $t_R$=6.91 min (Grad 2); ES-MS: $m/e_o$=516.2.

Example 87 trans-1-{3-[4-Amino-5-(3-benzyloxy-phenyl)-pyrrolo[2,3-d]pyrimidin-7-yl]-cyclobutylmethyl}-3-methyl-urea is prepared as described in Example 26 starting with methyl isocyanate (ChemService Inc., West Chester, Pa., U.S.A.). Analytical HPLC: $t_R$=6.55 min (Grad 2); ES-MS: $m/e_o$=457.0.

Example 88 cis-1-{3-[4-Amino-5-(3-benzyloxy-phenyl)-pyrrolo[2,3-d]pyrimidin-7-yl]-cyclobutylmethyl}-3-methyl-urea is prepared as described in Example 26 starting with cis-7-(3-aminomethyl-cyclobutyl)-5-(3-benzyloxy-phenyl)-7H-pyrrolo[2,3-d]pyrimidin-4-ylamine and methyl isocyanate (ChemService Inc., West Chester, Pa., U.S.A.). Analytical HPLC: $t_R$=6.49 min (Grad 2); ES-MS: $m/e_o$=456.9.

Example 89

To a suspension of 0.2 g (0.5 mmol) of trans-7-(3-aminomethyl-cyclobutyl)-5-(3-benzyloxy-phenyl)-7H-pyrrolo[2,3-d]pyrimidin-4-ylamine in 5 ml of acetonitrile are added under argon 108 mg (0.65 mmol) of 1,1-carbonyldiimidazole (Fluka, Buchs, Switzerland) and 628 µl (4.5 mmol) of triethylamine. The reaction mixture is stirred for 15 min at RT and 414 µl (5.0 mmol) of pyrrolidine (Fluka, Buchs, Switzerland) are added thereto. After stirring for 2.5 h at RT, the reaction mixture is concentrated and the crude compound is purified by reversed-phase medium pressure chromatography to provide trans-pyrrolidine-1-carboxylic acid {3-[4-amino-5-(3-benzyloxy-phenyl)-pyrrolo[2,3-d]pyrimidin-7-yl]-cyclobutylmethyl}-amide. Analytical HPLC: $t_R$=7.02 min (Grad 2); ES-MS: $m/e_o$=497.2.

Example 90 trans-Piperidine-1-carboxylic acid {3-[4-amino-5-(3-benzyloxy-phenyl)-pyrrolo[2,3-d]pyrimidin-7-yl]-cyclobutylmethyl}-amide is prepared as described in Example 89 using piperidine (Fluka, Buchs, Switzerland). Analytical HPLC: $t_R$=7.30 min (Grad 2); ES-MS: $m/e_o$=511.2.

Example 91 trans-Morpholine-4-carboxylic acid {3-[4-amino-5-(3-benzyloxy-phenyl)-pyrrolo[2,3-d]pyrimidin-7-yl]-cyclobutylmethyl)-amide is prepared as described in Example 89 using morpholine (Fluka, Buchs, Switzerland). Analytical HPLC: $t_R$=6.72 min (Grad 2); ES-MS: $m/e_o$=513.2.

Example 92 trans-3-{3-[4-Amino-5-(3-benzyloxy-phenyl)-pyrrolo[2,3-d]pyrimidin-7-yl]-cyclobutylmethyl}-1,1-dimethyl-urea is prepared as described in Example 89 using dimethylamine (Fluka, Buchs, Switzerland). Analytical HPLC: $t_R$=6.82 min (Grad 2); ES-MS: m/e$_o$=471.3.

Example 93 trans-4-Methyl-piperazine-1-carboxylic acid {3-[4-amino-5-(3-benzyloxy-phenyl)-pyrrolo[2,3-d]pyrimidin-7-yl]-cyclobutylmethyl}-amide is prepared as described in Example 89 using 1-methyl-piperazine (Fluka, Buchs, Switzerland). Analytical HPLC: $t_R$=6.01 min (Grad 2); ES-MS: m/e$_o$=526.2.

Example 94 trans-(3-[4-Amino-5-(3-benzyloxy-phenyl)-pyrrolo[2,3-d]pyrimidin-7-yl]-cyclobutylmethyl}-1,1-diethyl-urea is prepared as described in Example 89 using diethylamine (Fluka, Buchs, Switzerland). Analytical HPLC: $t_R$=7.22 min (Grad 2); ES-MS: m/e$_o$=499.2.

Example 95

To a solution of 0.2 g (0.5 mmol) of trans-7-(3-aminomethyl-cyclobutyl)-5-(3-benzyloxy-phenyl)-7H-pyrrolo[2,3-d]pyrimidin-4-ylamine in 5 ml of dichloromethane are added 55.4 µl (0.5 mmol) of 2-bromoethyl chloroformate (Fluka, Buchs, Switzerland) and 70 µl (0.5 mmol) of triethylamine. After stirring for 2 h at RT, the solution is concentrated to dryness. The crude compound is dissolved in 5 ml of acetonitrile and 260 µl (2.5 mmol) of diethylamine (Fluka, Buchs, Switzerland) are added thereto. The reaction mixture is refluxed for 16 h and, after concentration, the crude compound is purified by medium-pressure liquid chromatography to provide trans-{3-[4-amino-5-(3-benzyloxy-phenyl)pyrrolo[2,3-d]pyrimidin-7-yl]-cyclobutylmethyl}-carbamic acid 2-diethylamino-ethyl ester. Analytical HPLC: $t_R$=6.27 min (Grad 2); ES-MS: m/e$_o$=543.3.

Example 96 trans-{3-[4-Amino-5-(3-benzyloxy-phenyl)-pyrrolo[2,3-d]pyrimidin-7-yl]-cyclobutylmethyl}-carbamic acid 2-morpholin-4-yl-ethyl ester is prepared as described in Example 95 using morpholine (Fluka, Buchs, Switzerland). Analytical HPLC: $t_R$=6.18 min (Grad 2); ES-MS: m/e$_o$=557.2.

Example 97 trans-{3-[4-Amino-5-(3-benzyloxy-phenyl)-pyrrolo[2,3-d]pyrimidin-7-yl]-cyclobutylmethyl}-carbamic acid 2-(4-methyl-piperazin-1-yl)-ethyl ester is prepared as described in Example 95 using 1-methyl-piperazine (Fluka, Buchs, Switzerland). Analytical HPLC: $t_R$=5.88 min (Grad 2); ES-MS: m/e$_o$=570.2.

Example 98 trans-{3-[4-Amino-5-(3-benzyloxy-phenyl)-pyrrolo[2,3-d]pyrimidin-7-yl]-cyclobutylmethyl}-carbamic acid 2-dimethylamino-ethyl ester is prepared as described in Example 95 using dimethylamine (Fluka, Buchs, Switzerland). Analytical HPLC: $t_R$=6.14 min (Grad 2); ES-MS: m/e$_o$=515.2.

Example 99 trans-{3-[4-Amino-5-(3-benzyloxy-phenyl)-pyrrolo[2,3-d]pyrimidin-7-yl]-cyclobutylmethyl}-carbamic acid ethyl ester is prepared as described in Example 22 using ethyl chloroformate (Fluka, Buchs, Switzerland). Analytical HPLC: $t_R$=7.32 min (Grad 2); ES-MS: m/e$_o$=472.2.

Example 100 trans-4-{3-[4-Amino-5-(3-benzyloxy-phenyl)-pyrrolo[2,3-d]pyrimidin-7-yl]-cyclobutylmethyl}-piperazine-1-carboxylic acid ethyl ester is prepared as described in Example 62 using 1-ethoxycarbonylpiperazine (Fluka, Buchs, Switzerland). Analytical HPLC: $t_R$=9.25 min (Grad 1); ES-MS: m/e$_o$=541.2.

Example 101 cis-5-(3-Benzyloxy-phenyl)-7-(3-pyrrolidin-1-ylmethyl-cyclobutyl)-7-H-pyrrolo[2,3-d]pyrimidin-4-ylamine is prepared as described in Example 76 using pyrrolidine (Fluka, Buchs, Switzerland). Analytical HPLC: $t_R$=9.01 min (Grad 1); ES-MS: m/e$_o$=454.2.

Example 102 cis-7-(3-Azetidin-1-ylmethyl-cyclobutyl)-5-(3-benzyloxy-phenyl)-7H-pyrrolo[2,3-d]pyrimidin-4-ylamine is prepared as described in Example 76 using trimethyleneimine (Fluka, Buchs, Switzerland). Analytical HPLC: $t_R$=8.80 min (Grad 1); ES-MS: m/e$_o$=440.2.

Example 103 trans-3-[4-Amino-5-(3-benzyloxy-phenyl)-6-bromo-pyrrolo[2,3-d]pyrimidin-7-yl]-cyclobutanecarboxylic acid methylester To 11 g (25.67 mmol) trans-3-[4-amino-5-(3-benzyloxy-phenyl)-pyrrolo[2,3-d]pyrimidin-7-yl]-cyclobutanecarboxylic acid methyl ester (see Example 4) in 275 ml dry N,N-dimethylformamide, 5.18 g (28.24 mmol) N-bromosuccinimide are added in small portions. The solution is stirred at RT in the dark and under Argon for 17 h. Thereafter the solvent is evaporated, and the residue purified by chromatography on silicagel (solvent: hexane-ethyl acetate 3:1). Further purification is done by crystallization from acetonitrile. Analytical HPLC: $t_R$=3.61 min (shorty); ES-MS: m/e$_o$=506.9 and 508.9; mp: 124-125° C.; NMR (DMSO-d6): 8.18/s (1H), 7.25-7.5/several m's (6H), 7.09/"d" (1H); 7.04/s (1H); 6.98/"d" (1H); 5.38/m (1H); 5.13/s (2H); 3.69/s (3H); 3.50/m (2H); 3.29/m (1H); 2.62/m (2H).

Example 104 trans-3-[4-Amino-5-(3-benzyloxy-phenyl)-6-methyl-pyrrolo[2,3-d]pyrimidin-7-yl]-cyclobutanecarboxylic acid methyl ester In a sealed tube, 4.68 g (9.02 mmol) trans-3-[4-amino-5-(3-benzyloxy-phenyl)-6-bromo-pyrrolo[2,3-d]pyrimidin-7-yl]-cyclobutanecarboxylic acid methylester of Example 103, 2.08 g (1.8 mmol) tetrakistriphenylphosphin palladium and 5.3 ml (38.05 mmol) tin tetramethyl (Fluka, Buchs, Switzerland) are heated under Argon in 20 ml dry N,N-dimethylformamide for 30 h at 100-105° C. bath temperature. The reaction mixture is filtered on hyflo (Hyflo Super Cel®; Fluka, Buchs, Switzerland), and the residue washed thouroughly with N,N-dimethylformamide. The dark filtrate is evaporated at 60° C. to dryness, the residual mass dissolved in hot ethyl acetate and chromatographed on silicagel (hexane-ethyl acetate 25:75). The title compound is obtained as yellow crystals. Analytical HPLC: $t_R$=3.54 min (shorty); ES-MS: m/e$_o$=443; NMR (DMSO-d6): 8.08/s (1H), 7.25-7.5/several m's (6H), 6.99/"d" (1H); 6.90/s (1H); 6.85/"d" (1H); 5.09/s (2H); 5.06/m (1H); 3.64/s (3H); 3.2-3.5/2×m (3H); 2.59/m (2H); 2.18/s (3H).

Example 105 trans-{3-[4-Amino-5-(3-benzyloxy-phenyl)-6-methyl-pyrrolo[2,3-d]pyrimidin-7-yl]-cyclobutyl}-methanol 2.94 g (6.64 mmol) trans-3-[4-amino-5-(3-benzyloxy-phenyl)-6-methyl-pyrrolo[2,3-d]pyrimidin-7-yl]-cyclobutanecarboxylic acid methyl ester of Example 104 in 35 ml dry THF are added during 45 min to an ice-cold solution of 0.281 g (7.17 mmol) lithium aluminiumhydride in 30 ml dry THF. The reaction mixture is stirred at 0° C. for additional 20 h. Water is added slowly to the mixture (0.914 ml in 20 min; T≦4° C.), followed by 0.11 ml 4N NaOH. The precipitate is filtered off, the residue on the filter washed with ethyl acetate and water. The filtrate is extracted with ethyl acetate. After drying the organic phase with sodium sulfate, the solvent is evaporated and the residue purified by chromatography (solvent: ethyl acetate-MeOH 95:5). The title compound is obtained as a foam. Analytical HPLC: $t_R$=3.06 min (shorty); ES-MS: m/e$_o$=415; NMR (DMSO-d6): 8.10/s (1H), 7.25-7.5/several m's (6H), 7.25/"d" (1H); 6.95/s (1H); 6.90/1"d" (1H); 5.5-6.0/b (NH2); 5.13/s (2H); 5.04/m (1H); 4.69/t (OH); 3.57/t (2H); 3.15-3.25/m (2H); 2.4-2.5/m (1H); 2.23/s (3H); 2.15-2.25/m (2H).

Example 106 trans-Toluene-4-sulfonic add 3-[4-amino-5-(3-benzyloxy-phenyl)-6-methyl-pyrrolo[2,3-d]pyrimidin-7-yl]-cyclobutylmethyl ester 2.57 g (6.17 mmol) trans-3-[4-amino-5-(3-benzyloxy-phenyl)-6-methyl-pyrrolo[2,3-d]pyrimidin-7-yl]-cyclobutyl)methanol of Example 105 are dissolved in 50 ml dry pyridine. The solution is cooled to ca. −25° C. and 2.04 g (10.5 mmol) p-toluenesulfonyl chloride are added in 4 portions. After stirring 3 h at −20° C. and 24 h at 0-5° C., additional p-toluenesulfonyl chloride (0.36 g; 1.85 mmol) is added and stirring is continued for additional 19 h. The reaction mixture is poured into ice-water and extracted with dichloromethane. The organic phase is washed with water and brine. After evaporating the organic solvent, the residue is purified by filtration on silicagel (ethyl acetate-hexane 3:1). The compound is dried at RT and under high-vacuum for 18 h. Analytical HPLC: $t_R$=4.12 min (shorty); ES-MS: m/e$_o$=569.2; NMR (DMSO-d6): 8.09/s (1H); 7.84/d (2H); 7.25-7.6/several m's (8H), 7.06/"d" (1H); 6.93/s (1H); 6.88/"d" (1H); 5.5-6.0/b (NH2); 5.13/s (2H); 5.00/m (1H); 4.26/d (2H); 3.15-3.35/m (2H); 2.69/m (1H); 2.42/s (3H); 2.17/s (3H); 2.42/s (3H); 2.05-2.20/m (2H).

Example 107 trans-5-(3-Benzyloxy-phenyl)-6-methyl-7-(3-pyrrolidin-1-ylmethyl-cyclobutyl)-7H-pyrrolo[2,3-d]pyrimidin-4-ylamine 0.335 g (0.589 mmol) trans-toluene-4-sulfonic acid 3-[4-amino-5-(3-benzyloxy-phenyl)-6-methyl-pyrrolo[2,3-d]pyrimidin-7-yl]-cyclobutylmethyl ester of Example 106 in 3.6 ml pyrrolidine are stirred at RT for 3.5 h (Thin Layer Chromatography and HPLC control). The excess reagent is evaporated on a rotavap and the residue purified by chromatography (solvent: ethyl acetate-MeOH-aqu. NH$_3$ (33%) 95:5:1). The compound is crystallized from diethylether. Analytical HPLC: $t_R$=9.09 min (Grad 1); mp: 136-140° C.; ES-MS: m/e$_o$=468.3; NMR (DMSO-d6; not all signals reported): 8.10/s (1H), 7.25-7.5/several m's (6H), 7.02/"d" (1H); 6.94/s (1H); 6.89/"d" (1H); 5.5-6.0/b (NH2); 5.13/s (2H); 5.06/m (1H); 2.22/s (3H).

Example 108 trans-5-(3-Benzyloxy-phenyl)-6-methyl-7-[3-(4-methyl-piperazin-1-ylmethyl)-cyclobutyl]-7H-pyrrolo[2,3-d]pyrimidin-4-ylamine The title compound is obtained in analogy to Example 107 from 0.35 g (0.615 mmol) trans-toluene-4-sulfonic acid 3-[4-amino-5-(3-benzyloxy-phenyl)-6-methyl-pyrrolo[2,3-d]pyrimidin-7-yl]-cyclobutylmethyl ester and 3.5 ml (31.2 mmol) 1-methyl piperazine (RT; reaction time 24 h). Analytical HPLC: $t_R$=2.32 min (shorty); ES-MS: m/e$_o$=497.3; NMR (DMSO-d6; not all signals reported): 8.09/s (1H), 7.25-7.5/several m's (6H), 7.01/"d" (1H); 6.94/s (1H); 6.89/"d" (1H); 5.5-6.0/b (NH2); 5.13/s (2H); 5.07/m (1H); 2.22/s (3H); 2.13/s (3H).

Example 109 trans-1-{3-[4-Amino-5-(3-benzyloxy-phenyl)-6-methyl-pyrrolo[2,3-d]pyrimidin-7-yl]-cyclobutylmethyl}-piperidin-4-ol The title compound is obtained in analogy to Example 107 from 0.35 g (0.615 mmol) trans-toluene-4-sulfonic acid 3-[4-amino-5-(3-benzyloxy-phenyl)-6-methyl-pyrrolo[2,3-d]pyrimidin-7-yl]-cyclobutylmethyl ester and a total of 0.44 g (4.3 mmol) 4-hydroxy piperidine in 3.5 ml of dry N,N-dimethyl acetamide (RT; 144 h; after 46 h 64 mg of reagent are added to complete the reaction). Analytical HPLC: $t_R$=2.54 min (shorty); ES-MS: m/e$_o$=498.3; NMR (DMSO-d6; not all signals reported): 8.09/s (1H), 7.25-7.5/several m's (6H), 7.01/"d" (1H); 6.94/s (1H); 6.89/"d" (1H); 5.5-6.0/b (NH2); 5.13/s (2H); 5.06/m (1H); 4.51/d (OH); 2.22/s (3H).

Example 110 trans-7-(3-Azetidin-1-ylmethyl-cyclobutyl)-5-(3-benzyloxy-phenyl)-6-methyl-7-H-pyrrolo[2,3-d]pyrimidin-4-ylamine The title compound is obtained in analogy to Example 107 from 0.35 g (0.65 mmol) trans-toluene-4-sulfonic acid 3-[4-amino-5-(3-benzyloxy-phenyl)-6-methyl-pyrrolo[2,3-d]pyrimidin7-yl]-cyclobutylmethyl ester and 0.215 ml (3.08 mmol) trimethylenimin (Fluka, Buchs, Switzerland) in 3.5 ml N,N-dimethylacetamide (RT; reaction time 120 h). Analytical HPLC: $t_R$=8.97 min (Grad 1); ES-MS: m/e$_o$=454.3; NMR (DMSO-d6): 8.09/s (1H), 7.25-7.5/several m's (6H), 7.01/"d" (1H); 6.93/s (1H); 6.89/"d" (1H); 5.5-6.0/b (NH2); 5.13/s (2H); 5.02/m (1H); ca. 3.3/m (1H); 3.2/m (2H); 3.10/t (2H); 2.54/d (2H); 2.30/m (1H); 2.21/s (3H); 2.11/m (2H); 1.94/m (2H).

Example 111 trans-5-(3-Benzyloxy-phenyl)-6-methyl-7-{3-[(tetrahydro-pyran-4-ylamino)-methyl]-cyclobutyl}-7H-pyrrolo[2,3-d]pyrimidin-4-ylamine The title compound is obtained in analogy to Example 107 from 0.35 g (0.62 mmol) trans-toluene-4-sulfonic acid 3-[4-amino-5-(3-benzyloxy-phenyl)-6-methyl-pyrrolo[2,3-d]pyrimidin-7-yl]-cyclobutylmethyl ester and 0.446 mg (4.42 mmol) tetrahydropyran-4-ylamin (obtained from tetrahydropyran-4-one oxime by hydrogenation) in 3.5 ml N,N-dimethylacetamide (RT; reaction time 310 h). Analytical HPLC: $t_R$=8.99 min (Grad 1); ES-MS: m/e$_o$=498.3; NMR (DMSO-d6; not all signals reported): 8.09/s (1H), 7.25-7.5/several m's (6H), 7.02/"d" (1H); 6.94/s (1H); 6.89/ "d" (1H); 5.5-6.0/b (NH2); 5.13/s (2H); 5.06/m (1H); 3.82/m (2H); 2.75/d (2H); 2.23/s (3H).

Example 112 trans-((R)-1-{3-[4-Amino-5-(3-benzyloxy-phenyl)-6-methyl-pyrrolo[2,3-d]pyrimidin-7-yl]-cyclobutylmethyl}-pyrrolidin-2-yl)-methanol The title compound is obtained in analogy to Example 107 from 0.35 g (0.62 mmol) trans-toluene-4-sulfonic acid 3-[4-amino-5-(3-benzyloxy-phenyl)-6-methyl-pyrrolo[2,3-d]pyrimidin-7-yl]-cyclobutylmethyl ester and 0.307 ml (3.08 mmol) D-prolinol (Fluka, Buchs, Switzerland) in 3.5 ml N,N-dimethylacetamide (RT; reaction time 114 h). Analytical HPLC: $t_R$=8.95 min (Grad 1); ES-MS: m/e$_o$=498.3; NMR (DMSO-d6; not all signals reported): 8.10/s (1H), 7.25-7.5/several m's (6H), 7.02/"d" (1H); 6.94/s (1H); 6.92/ "d" (1H); 5.5-6.0/b (NH2); 5.13/s (2H); 5.06/m (1H); 4.37/ bs (OH); 2.23/s (3H).

Example 113 cis-3-[4-Amino-5-(3-benzyloxy-phenyl)-6-bromo-pyrrolo[2,3-d]pyrimidin-7-yl]-cyclobutanecarboxylic acid methyl ester The title compound is prepared in analogy to Example 103 starting from 12.9 g (30.11 mmol) cis-3-[4-amino-5-(3-benzyloxy-phenyl)-pyrrolo[2,3-d]pyrimidin-7-yl]-cyclobutanecarboxylic acid methyl ester (see Step 3.1 above) and 6.07 g (33.12 mmol) N-bromosuccinimide in 250 ml dry N,N-dimethylformamide. After work-up, the raw material is purified by chromatography on silicagel (solvent: hexane-ethyl acetate 1:1). Analytical HPLC: $t_R$=11.85 min (Grad 1); ES-MS: m/e$_o$=506.9 and 509.9; NMR (DMSO-d6): 8.14/s (1H), 7.3-7.5/several m's (6H), 7.09/"d" (1H); 7.05/s (1H); 6.98/"d" (1H); 5.5-6.5/b (NH2); 5.13/s (2H); 5.11/m (1H); 3.66/s (3H); 3.35-3.5/m (2H); 3.08/m (1H); 2.58-2.7/m (2H).

Example 114 cis-3-[4-Amino-5-(3-benzyloxy-phenyl)-6-methyl-pyrrolo[2,3-d]pyrimidin-7-yl]-cyclobutanecarboxylic acid methyl ester The title compound is prepared in analogy to Example 104 starting from 6.6 g (12.6 mmol) cis-3-[4-amino-5-(3-benzyloxy-phenyl)-6-bromo-pyrrolo[2,3-d]pyrimidin-7-yl]-cyclobutane-carboxylic acid methyl ester of Example 113, 0.364 g (0.315 mmol) tetrakistriphenyl palladium, and 4.39 ml (31.52 mmol) tin tetramethyl (Fluka, Buchs, Switzerland) in 20 ml dry N,N-dimethylformamide (T=100-110° C., sealed tube; reaction time=25 h). Analytical HPLC: $t_R$=11.67 min (Grad 1); ES-MS: m/e$_o$=443.2; NMR (DMSO-d6; not all signals reported): 8.07/s (1H), 7.25-7.5/several m's (6H), 7.03/"d" (1H); 6.95/s (1H); 6.90/"d" (1H); 5.5-6.0/b (NH2); 5.14/s (2H); 4.90/m (1H); 3.65/s (3H); 2.25/s (3H).

Example 115 cis-{3-[4-Amino-5-3-benzyloxy-phenyl)-6-methyl-pyrrolo[2,3-d]pyrimidin-7-yl]-cyclobutyl}-methanol The title compound is obtained in analogy to Example 105 starting from 2.06 g cis-3-[4-amino-5-(3-benzyloxy-phenyl)-6-methyl-pyrrolo[2,3-d]pyrimidin-7-y]-cyclobutanecarboxylic acid methyl ester of Example 114 and 0.216 mmol lithium aluminiumhydride in 20 ml dry THF (T=0-5° C.; reaction time 49 h). The product is purified by flash chromatography (solvent: ethyl acetate). Analytical HPLC: $t_R$=3.13 min (shorty); ES-MS: m/e$_o$=415.4; NMR (DMSO-d6): 8.07/s (1H), 7.25-7.5/several m's (6H), 7.02/"d" (1H); 6.94/s (1H); 6.89/"d" (1H); 5.5-6.0/b (NH2); 5.13/s (2H); 4.84/m (1H); 4.62/t (OH); 3.53/t (2H); 2.8-2.9/m (2H); 2.35-2.45/m (2H); 2.24/s (3H); 2.2/m (1H).

Example 116 cis-5-(3-Benzyloxy-phenyl)-6-methyl-7-(3-pyrrolidin-1-ylmethyl-cyclobutyl)-7-H-pyrrolo[2,3-d]pyrimidin-4-ylamine To a solution of 0.2 g (0.48 mmol) cis-{3-[4-amino-5-(3-benzyloxy-phenyl-6-methyl-pyrrolo[2,3-d]pyrimidin-7-yl]-cyclobutyl}-methanol of Example 115 in 2 ml dry pyridine cooled to ca. −25° C. 0.159 g (0.96 mmol) p-toluenesulfonyl chloride are added in 1 h in three portions. Stirring continued for 1 h at −20° C. and overnight at 0° C. To this reaction mixture is added in 1 h under Argon 2 ml of pyrrolidine (T=0-5° C.) and stirring is continued for additional 3 h. The reaction mixture is partitioned between ethyl acetate and water. After drying with sodium sulfate the solvent is evaporated and the residue purified by flash chromatography (solvent: ethyl acetate-MeOH-NH$_3$ aqu. (33%) 95:5:1). Analytical HPLC: $t_R$=9.28 min (Grad 1); ES-MS: m/e$_o$=468.2; NMR (DMSO-d6): 8.08/s (1H), 7.25-7.5/several m's (6H), 7.02/"d" (1H); 6.94/s (1H); 6.89/"d" (1H); 5.4-5.9/b (NH2); 5.13/s (2H); 4.77/m (1H); 2.8-2.9/m (2H); 2.60/d (2H); 2.35-ca. 2.5/m (6H); 2.23/s (3H); ca. 2.15-2.25/m (1H); 1.6-1.7/m (4H).

Example 117 cis-5-(3-Benzyloxy-phenyl)-6-methyl-7-[3-(4-methyl-piperazin-1-ylmethyl)-cyclobutyl]-7H-pyrrolo[2,3-d]pyrimidin-4-ylamine The title compound is prepared in a one pot reaction in analogy to Example 116 starting from 0.35 g (0.84 mmol) cis-{3-[4-amino-5-(3-benzyloxy-phenyl)-6-methyl-pyrrolo[2,3-d]pyrimidin-7-yl]-cyclobutyl}-methanol and 0.328 g (1.69 mmol) p-toluenesulfonyl chloride in 3.5 ml dry pyridine, followed by 3.5 ml (31.2 mmol) 1-methyl piperazine. Analytical HPLC: $t_R$=8.14 min (Grad 1); ES-MS: m/$e_o$=497.3; NMR (DMSO-d6; not all data reported): 8.08/s (1H), 7.25-7.45/several m's (6H), 7.02/"d" (1H); 6.94/s (1H); 6.89/"d" (1H); 5.4-6.0/b (NH2); 5.13/s (2H); 4.77/m (1H); 2.22/s (3H); 2.12/s (3H).

Example 118 cis-7-(3-Azetidin-1-ylmethyl-cyclobutyl)-5-(3-benzyloxy-phenyl)-6-methyl-7H-pyrrolo[2,3-d]pyrimidin-4-ylamine The title compound is prepared in analogy to Example 116 starting from 0.35 g (0.84 mmol) cis-{3-[4-amino-5-(3-benzyloxy-phenyl)-6-methyl-pyrrolo[2,3-d]pyrimidin-7-yl]-cyclobutyl}-methanol and 0.328 g (1.69 mmol) p-toluenesulfonyl chloride in 3.5 ml dry pyridine, followed by 0.442 ml (6.33 mmol) trimethylenimine (Fluka, Buchs, Switzerland). Analytical HPLC: $t_R$=9.22 min (Grad 1); ES-MS: m/$e_o$=454.3; NMR (DMSO-d6): 8.08/s (1H), 7.25-7.5/several m's (6H), 7.02/"d" (1H); 6.93/s (1H); 6.89/"d" (1H); 5.4-6.0/b (NH2); 5.13/s (2H); 4.76/m (1H); 3.11/"t" (4H); 2.75-2.90/m (2H); 2.54/d (2H); 2.35-2.45/m (2H); 2.22/s (3H); 2.03/m (1H); 1.9-2.0/m (2H).

Example 119 cis-1-{3-[4-Amino-5-(3-benzyloxy-phenyl)-6-methyl-pyrrolo[2,3-d]pyrimidin-7-yl]-cyclobutylmethyl}-piperidin-4-ol The title compound is prepared in analogy to Example 116 starting from 0.35 g (0.84 mmol) cis-{3-[4-amino-5-(3-benzyloxy-phenyl)-6-methyl-pyrrolo[2,3-d]pyrimidin-7-yl]-cyclobutyl}methanol and 0.328 g (1.69 mmol) p-toluenesulfonyl chloride in 3.5 ml dry pyridine, followed by 0.87 g (8.44 mmol) 4-hydroxypiperidine (Fluka, Buchs, Switzerland). Analytical HPLC: $t_R$=8.76 min (Grad 1); ES-MS: m/$e_o$=498.2; NMR (DMSO-d6; not all signals reported): 8.07/s (1H), 7.25-7.5/several m's (6H), 7.01/"d" (1H); 6.94/s (1H); 6.89/"d" (1H); 5.13/s (2H); 4.76/m (1H); 4.51/d (OH); 2.22/s (3H).

Example 120 cis-((R)-1-{3-[4-Amino-5-(3-benzyloxy-phenyl)-6-methyl-pyrrolo[2,3-d]pyrimidin-7-yl]-cyclobutylmethyl}-pyrrolidin-2-yl)-methanol The title compound is prepared in analogy to Example 116 starting from 0.35 g (0.84 mmol) cis-{3-[4-amino-5-(3-benzyloxy-phenyl)-6-methyl-pyrrolo[2,3-d]pyrimidin-7-yl]-cyclobutyl}-methanol and 0.328 g (1.69 mmol) p-toluenesulfonyl chloride in 3.5 ml dry pyridine, followed by 0.631 ml (6.33 mmol) D-prolinol (Fluka, Buchs, Switzerland). Analytical HPLC: $t_R$=9.08 min (Grad 1); ES-MS: m/$e_o$=498.2; NMR (DMSO-d6; not all signals reported): 8.07/s (1H), 7.25-7.5/several m's (6H), 7.02/"d" (1H); 6.94/s (1H); 6.89/"d" (1H); 5.4-6.0/b (NH2); 5.13/s (2H); 4.78/m (1H); 4.34/b (OH); 2.22/s (3H).

Example 121

5-(3-Benzyloxy-phenyl)-6-bromo-7H-pyrrolo[2,3-d]pyrimidin-4-ylamine

To a solution of 20 g (63.2 mmol) 5-(3-benzyloxy-phenyl)-7H-pyrrolo[2,3-d]pyrimidin-4-ylamine (see WO 97/28161) in 1 l dry N,N-dimethylformamide, 12.4 g (69.5 mmol) N-bromosuccinimide are added at ca. 10° C. Stirring was continued at ca. 10° C. for 30 min and overnight at RT. The precipitate formed is filtered off and washed thoroughly with N,N-dimethylformamide and hexane. After drying for 24 h at 30-35° C. under vacuum, the title compound is used in the next step without further purification. Additional material can be obtained from the mother liquor through chromatography on silicagel. Analytical HPLC: $t_R$=10.07 min (Grad 1); ES-MS: m/$e_o$=394.9 and 396.9; NMR (DMSO-d6): 12.55/s (NH); 8.06/s (1H), 7.25-7.5/several m's (6H), 7.07/"d" (1H); 7.03/s (1H); 6.98/"d" (1H); 5.5-6.0/b (NH2); 5.12/s (2H).

Example 122

5-(3-Benzyloxy-phenyl)-6-ethyl-7H-pyrrolo[2,3-d]pyrimidin-4-ylamine

In a sealed tube 12.53 g (31.7 mmol) 5-(3-benzyloxy-phenyl)-6-bromo-7H-pyrrolo[2,3-d]pyrimidin-4-ylamine, 32 ml (158.5 mmol) tin tetraethyl (Aldrich), and 7.32 g (6.34 mmol) tetrakis triphenylphosphin palladium are heated under Argon at 90° C. for 66 h (reaction control by HPLC and MS). After that time, the reaction suspension is filtered on hyflo and the solvent evaporated on a rotavap under high vacuum at 50-60° C. The residue is partitioned between ethyl acetate and water. The organic phase is dried over sodium sulfate and is evaporated. The residue is purified by chromatography on silicagel (ethyl acetate-methanol 95:5). Crystallization is done from acetone. Analytical HPLC: $t_R$=10.43 min (Grad 1); ES-MS: m/$e_o$=345.1; NMR (DMSO-d6): 11.65/s (NH); 8.03/s (1H), 7.25-7.5/m and 6.85-7.1/m (9H), 5.5-6.0/b (NH2); 5.14/s (2H); 2.54/q (2H); 1.14/s (3H).

Example 123 cis and trans-3-[4-Amino-5-(3-benzyloxy-phenyl)-6-ethyl-pyrrolo[2,3-d]pyrimidin-7-yl]-cyclobutanecarboxylic acid methyl ester A mixture of 1.26 g (2.74 mmol) 5-(3-benzyloxy-phenyl)-6-ethyl-7H-pyrrolo[2,3-d]pyrimidin-4-ylamine, 1.53 g (10.9 mmol) of powdered potassium carbonate and 2.92 g (10.9 mmol) 18-crown-6 ether in 12 ml dry N,N-dimethylformamide is stirred for 15 min at 80° C. 1.7 g (8.2 mmol) of 3-Methanesulfonyloxy-cyclobutanecarboxylic acid methyl ester, dissolved in 9 ml dry N,N-dimethylformamide, is added dropwise in 15 min. After stirring for 42 h at 80° C., work-up is effected by filtering the reaction mixture on hyflo and evaporating the solvent. The residue is partitioned between water and ethyl acetate. The organic layer is dried over sodium sulfate and concentrated in vacuo. The crude product is purified and separated by flash chromatography (hexane-ethyl acetate 1:2). The ratio cis to trans isomer is about 70:30 (by HPLC, Grad25).

cis: Analytical HPLC: $t_R$=12.27 min (Grad 1); ES-MS: m/e$_o$=457.0; NMR (DMSO-d6): 8.12/s (1H), 7.3-7.5/several m's (6H), 7.07/"d" (1H); 6.96/s (1H); 6.91/"d" (11H); 5.5-6.1/b (NH2); 5.15/s (2H); 4.81/m (1H); 3.67/s (3H); 3.49/q (2H); 3.03/m (1H); 2.62/m (4H); 1.08/t (3H). trans: Analytical HPLC: $t_R$=12.65 min (Grad 1); ES-MS: m/e$_o$=457.0; NMR (DMSO-d6): 8.37/s (1H); 7.3-7.5/several m's (6H), 7.11/"d" (1H); 6.97/s (1H); 6.93/"d" (1H); 5.15/s (2H); 5.11/m (1H); 3.70/s (3H); 3.3-3.5/m (3H); 2.72/m (2H); 2.62/q (2H); 1.06/t (3H); NH2 not visible.

Example 124 cis-{3-[4-Amino-5-(3-benzyloxy-phenyl)-6-ethyl-pyrrolo[2,3-d]pyrimidin-7-yl]-cyclobutyl}methanol In analogy to Example 105, 0.73 g (1.56 mmol) cis-3-[4-amino-5-(3-benzyloxy-phenyl)-6-ethyl-pyrrolo[2,3-d]pyrimidin-7-yl]-cyclobutanecarboxylic acid methyl ester of Example 123 are reduced with 69 mg (1.73 mmol) lithium aluminiumhydride in THF. Reaction time: 18 h at 0-5° C. Analytical HPLC: $t_R$=11.15 min (Grad 1); ES-MS: m/e$_o$=429.1; NMR (DMSO-d6): 8.10/s (1H); 7.3-7.5/several m's (6H), 7.04/"d" (1H); 6.93/s (1H); 6.90/"d" (1H); 5.4-6.0/b (NH2); 5.15/s (2H); 4.75/m (1H); 4.63/"t" (OH); 3.60/t (2H); 3.03 q (2H); 2.61/q (2H); 2.14/q (2H); 2.24/m (1H); 1.07/t (3H).

Example 125 trans-{3-[4-Amino-5-(3-benzyloxy-phenyl)-6-ethyl-pyrrolo[2,3-d]pyrimidin-7-yl]-cyclobutyl}-methanol In analogy to Example 105, 0.49 g (1.09 mmol) trans-3-[4-amino-5-(3-benzyloxy-phenyl)-6-ethyl-pyrrolo[2,3-d] pyrimidin-7-yl]-cyclobutanecarboxylic acid methyl ester of Example 123 are reduced with 46 mg (1.18 mmol) lithium aluminiumhydride in THF. Reaction time: 17 h at 0-5° C. Analytical HPLC: $t_R$=10.91 min (Grad 1); ES-MS: m/e$_o$=429.1; NMR (DMSO-d6): 8.13/s (1H); 7.3-7.6/several m's (6H), 7.061/"d" (1H); 6.95/s (1H); 6.90/"d" (1H); 5.4-6.0/b (NH2); 5.15/s (2H); 4.93/m (1H); 4.681/"t" (OH); 3.60/m (2H); ca. 3.3-3.4/m (2H); 2.95/q (2H); 2.20/m (2H); 2.24/m (1H); 1.05/t (3H).

Example 126 cis-5-(3-Benzyloxy-phenyl)-6-ethyl-7-(3-pyrrolidin-1-ylmethyl-cyclobutyl)-7H-pyrrolo[2,3-d]pyrimidin-4-ylamine The title compound is prepared in a one pot reaction in analogy to Example 116 starting from 0.2 g (0.46 mmol) cis-{3-[4-amino-5-(3-benzyloxy-phenyl)-6-ethyl-pyrrolo[2,3-d]pyrimidin-7-yl]-cyclobutyl}-methanol of Example 124 and 0.18 g (0.92 mmol) p-toluenesulfonyl chloride in 2 ml dry pyridine followed by 2 ml pyrrolidine. The reaction is controlled by tlc. Analytical HPLC: $t_R$=9.61 min (Grad 1); ES-MS: m/e$_o$=482.0; NMR (DMSO-d6; not all signals reported): 8.12/s (1H); 6.9-7.5/several m's (6H), 7.05/"d" (1H); 6.95/s (1H); 6.92/"d" (1H); 5.4-6.0/b (NH2); 5.15/s (2H); 4.72/m (1H); 2.62/q (2H); 1.06/t (3H).

Example 127 cis-5-(3-Benzyloxy-phenyl)-6-ethyl-7-[3-(4-methyl-piperazin-1-ylmethyl)-cyclobutyl]-7H-pyrrolo[2,3-d]pyrimidin-4-ylamine The title compound is prepared in analogy to Example 116 from cis-{3-[4-amino-5-(3-benzyloxy-phenyl)-6-ethyl-pyrrolo[2,3-d]pyrimidin-7-yl]-cyclobutyl}-methanol of Example 124, p-toluenesulfonyl chloride and N-methyl-piperazine. Analytical HPLC-MS: $t_R$=1.40 min (Grad 1); ES-MS: m/e$_o$=511.45.

Example 128 cis-7-(3-Azetidin-1-ylmethyl-cyclobutyl)-6-ethyl-5-{3-[(Z)-2-eth-(E)-ylidene-hexa-3,5-dienyloxy]-phenyl}-7H-pyrrolo[2,3-d]pyrimidin-4-ylamine The title compound is prepared in analogy to Example 116 from cis-{3-[4-amino-5-(3-benzyloxy-phenyl)-6-ethyl-pyrrolo[2,3-d]pyrimidin-7-yl]-cyclobutyl}-methanol of Example 124, p-toluenesulfonyl chloride and trimethylen-imin (Fluka, Buchs, Switzerland). Analytical HPLC-MS: $t_R$=1.51 min; ES-MS: m/e$_o$=468.45.

Example 129 cis-1-{3-[4-Amino-5-(3-benzyloxy-phenyl)-6-ethyl-pyrrolo[2,3-d]pyrimidin-7-yl]-cyclobutylmethyl}-piperidin-4-ol The title compound is prepared in analogy to Example 116 from cis-{3-[4-amino-5-(3-benzyloxy-phenyl)-6-ethyl-pyrrolo[2,3-d]pyrimidin-7-yl]-cyclobutyl}methanol of Example 124, p-toluenesulfonyl chloride and 4-hydroxypiperidine (Fluka, Buchs, Switzerland). Analytical HPLC-MS: $t_R$=1.49 min; ES-MS: m/e$_o$=512.48.

Example 130 cis-((R)-1-{3-[4-Amino-5-(3-benzyloxy-phenyl)-6-ethyl-pyrrolo[2,3-d]pyrimidin-7-yl]-cyclobutylmethyl}-pyrrolidin-2-yl)-methanol The title compound is prepared in analogy to Example 116 from cis-{3-[4-amino-5-(3-benzoyloxy-phenyl)-6-ethyl-pyrrolo[2,3-d]pyrimidin-7-yl]-cyclobutyl}-methanol of Example 124, p-toluenesulfonyl chloride and D-prolinol (Fluka, Buchs, Switzerland). Analytical HPLC-MS: $t_R$=1.48 min; ES-MS: m/e$_o$=512.48.

Example 131 cis-5-(3-Benzyloxy-phenyl)-6-ethyl-7-{3-[(tetrahy-dro-pyran-4-ylamino)-methyl]-cyclobutyl}-7H-pyrrolo[2,3-d]pyrimidin-4-ylamine The title compound is prepared in analogy to Example 116 from cis-{3-[4-amino-5-(3-benzyloxy-phenyl)-6-ethyl-pyrrolo[2,3-d]pyrimidin-7-yl]-cyclobutyl}-methanol of Example 124, p-toluenesulfonyl chloride and teztrahydro-pyran-4-ylamin (see Example 111). Analytical HPLC-MS: $t_R$=1.50 min; ES-MS: m/e$_o$=512.49.

Example 132

Test for activity against IGF-I induced IGF-IR autophosphorylation using the cellular "Capture ELISA" test The cellular "Capture ELISA" test is carried out as described above. The $IC_{50}$ values for some of the compounds of the present invention are given below:

| Compound from Example | $IC_{50}$ (μM) |
|---|---|
| 1 | 0.062 |
| 2 | 0.03 |
| 9 | 0.042 |
| 10 | 0.07 |
| 14 | 0.03 |
| 22 | 0.08 |
| 23 | 0.031 |
| 24 | 0.095 |
| 26 | 0.055 |
| 27 | 0.05 |
| 28 | 0.05 |
| 31 | 0.03 |
| 49 | 0.04 |
| 50 | 0.011 |
| 51 | 0.03 |
| 57 | 0.018 |
| 70 | 0.05 |
| 75 | 0.05 |
| 77 | 0.05 |
| 81 | 0.08 |
| 83 | 0.052 |
| 88 | 0.057 |
| 90 | 0.09 |
| 95 | 0.08 |
| 96 | 0.05 |
| 98 | 0.04 |
| 102 | 0.06 |
| 109 | 0.15 |
| 110 | 0.14 |
| 112 | 0.09 |
| 116 | 0.15 |
| 117 | 0.13 |

Example 133

Tablets

Tablets comprising 50 mg of active ingredient, for example one of the compounds of formula I described in Examples 1 to 131, and having the following composition are prepared in customary manner:

| Composition: | |
|---|---|
| active ingredient | 50 mg |
| wheat starch | 150 mg |
| lactose | 125 mg |
| colloidal silicic acid | 12.5 mg |
| talc | 22.5 mg |
| magnesium stearate | 2.5 mg |
| Total: | 362.5 mg |

Preparation: The active ingredient is mixed with a portion of the wheat starch, with the lactose and the colloidal silicic acid and the mixture is forced through a sieve. A further portion of the wheat starch is made into a paste, on a water bath, with five times the amount of water and the powder mixture is kneaded with the paste until a slightly plastic mass is obtained.

The plastic mass is pressed through a sieve of about 3 mm mesh size and dried, and the resulting dry granules are again forced through a sieve. Then the remainder of the wheat starch, the talc and the magnesium stearate are mixed in and the mixture is compressed to form tablets weighing 145 mg and having a breaking notch.

Example 134

Soft Capsules 5000 soft gelatin capsules comprising each 50 mg of active ingredient, for example one of the compounds of formula I described in Examples 1 to 131, are prepared in customary manner.

| Composition: | |
|---|---|
| active ingredient | 250 g |
| Lauroglykol | 2 liters |

Preparation: The pulverized active ingredient is suspended in Lauroglykol® (propylene glycol laurate, Gattefossé S. A., Saint Priest, France) and ground in a wet pulverizer to a particle size of approx. 1 to 3 μm. 0.419 g portions of the mixture are then dispensed into soft gelatin capsules using a capsule-filling machine.

The invention claimed is:

1. A compound of formula I

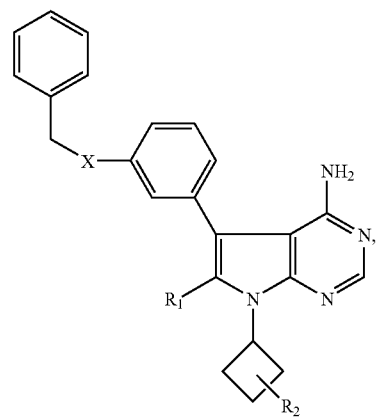

wherein
$R_1$ is hydrogen, unsubstituted or substituted lower alkyl or halogen,
$R_2$ is lower alkyl substituted by unsubstituted, mono- or disubstituted amino or by a heterocyclic radical; a radical $R_3$—(C=Y)-Z-, wherein $R_3$ is unsubstituted or substituted lower alkyl, unsubstituted, mono- or disubstituted amino, a heterocyclic radical, or if Z is present is also free or etherified hydroxy, Y is oxygen, sulfur or imino, and Z is either not present, lower alkylene or amino-lower alkylene; or a radical $R_4$-sulfonylamino-lower alkylene, wherein $R_4$ is unsubstituted or substituted lower alkyl, unsubstituted, mono- or disubstituted amino or phenyl optionally substituted by lower alkyl, lower alkoxy or nitro, and
X is a heteroatom selected from oxygen, NH and sulfur, or a salt thereof.

2. A compound of formula I according to claim 1, wherein
$R_1$ is hydrogen, unsubstituted or substituted lower alkyl or halogen,
$R_2$ is lower alkyl substituted by a substituted heterocyclic radical; a radical $R_3$—(C=Y)-Z-, wherein
$R_3$ is unsubstituted or substituted lower alkyl, unsubstituted, mono- or disubstituted amino, a heterocyclic radical, or if Z is present is also free or etherified hydroxy, Y is oxygen, sulfur or imino, and Z is either not present, lower alkylene or amino-lower alkylene, with the proviso that Z is not present or lower alkylene if $R_3$ is lower alkylene and Z is lower alkylene or amino-lower alkylene if $R_3$ is mono- or disubstituted amino or a heterocyclic radical; or a radical $R_4$-sulfonylamino-lower alkyl, wherein $R_4$ is unsubstituted or substituted lower alkyl, unsubstituted, mono- or disubstituted amino or phenyl optionally substituted by lower alkyl, lower alkoxy or nitro, and
X is a heteroatom selected from oxygen, NH and sulfur, or a salt thereof.

3. A compound of formula I according to claim 1, wherein
$R_1$ is hydrogen, unsubstituted or substituted lower alkyl or halogen,
$R_2$ is lower alkyl substituted by amino, N-lower alkylamino, N,N-di-lower alkylamino or by an unsubstituted heterocyclic radical; or a radical $R_3$—(C=Y)-Z-, wherein $R_3$ is lower alkyl, mono- or disubstituted amino or a heterocyclic radical, Y is oxygen, sulfur or imino, and Z is amino-lower alkylene if $R_3$ is lower alkyl and not present if $R_3$ is a heterocyclic radical or mono- or disubstituted amino, and
X is a heteroatom selected from oxygen, NH and sulfur, or a salt thereof.

4. A compound of formula I according to claim 1, wherein
$R_1$ is hydrogen, unsubstituted or substituted lower alkyl or halogen,
$R_2$ is lower alkyl substituted by unsubstituted, mono- or disubstituted amino or by a heterocyclic radical having from 4 to 8 ring members and from 1 to 3 heteroatoms whereby at least one heteroatom is nitrogen and the binding of the heterocyclic radical to lower alkyl occurs via a nitrogen ring atom; a radical $R_3$—(C=Y)-Z-, wherein $R_3$ is lower alkyl, unsubstituted, mono- or disubstituted amino, a heterocyclic radical having from 4 to 8 ring members and from 1 to 3 heteroatoms whereby at least one heteroatom is nitrogen and the binding of the heterocyclic radical occurs via a nitrogen ring atom, lower alkyl substituted by said heterocyclic radical or by one or more radicals selected independently of one another from the group consisting of amino, N-lower alkylamino, N,N-di-lower alkylamino, N-lower alkanoylamino, N,N-di-lower alkanoylamino, hydroxy, lower alkoxy, lower alkoxy-lower alkoxy, lower alkanoyl, lower alkanoyloxy, cyano, nitro, carboxy, lower alkoxycarbonyl, carbamoyl, amidino, guanidino, ureido, mercapto, lower alkylthio and halogen, or if Z is present is also free or etherified hydroxy, Y is oxygen, sulfur or imino, and Z is either not present, lower alkylene or amino-lower alkylene; or a radical $R_4$-sulfonylamino-lower alkyl, wherein $R_4$ is unsubstituted or substituted lower alkyl, unsubstituted, mono- or disubstituted amino or phenyl optionally substituted by lower alkyl, lower alkoxy or nitro, and
X is a heteroatom selected from oxygen, NH and sulfur, or a salt thereof.

5. A compound of formula I according to claim 1, wherein
$R_1$ is hydrogen,
$R_2$ is amino-lower akyl, N-lower alkylamino-lower alkyl, N,N-di-lower alkylamino-lower akyl, morpholinyl-lower alkyl piperidyl-lower alkyl pyrrolidinyl-lower alkyl lower alkyl-piperazinyl-lower alkyl, adamantanyl-amino-lower alkyl, hydroxy-piperidyl-lower alkyl, azepanyl-lower alkyl, di-lower alkyl-pyrrolidinyl-lower alkyl, azetidinyl-lower alkyl aminocarbonyl-piperidyl-lower alkyl pyridyl-piperazinyl-lower alkyl, thiomorpholinyl-lower alkyl, di-lower alkyl-morpholinyl-lower alkyl, aminocarbonyl-pyrrolidinyl-lower alkyl lower alkoxycarbonyl-piperazinyl-lower alkyl or phenyl-piperazinyl-lower alkyl; a radical $R_3$—(C=Y)-Z-, wherein $R_3$ is lower alkyl, amino, N-lower alkylamino, N,N-di-lower alkylamino, N-(phenyl-lower alkyl)-amino, N-(lower alkyl-phenyl-lower alkyl)-amino, N-(lower alkoxy-phenyl-lower alkyl)-amino, N-(morpholinyl-lower alkyl)-amino, N,N-di-lower alkylamino-lower alkylamino, pyrrolidinyl, piperidyl, morpholinyl, lower alkyl-piperazinyl, piperidyl-lower alkyl, morpholinyl-lower alkyl, lower alkyl-piperazinyl-lower alkyl, or lower alkoxy-lower alkyl, lower alkoxy-lower alkoxy-lower alkyl, Y is oxygen or imino, and Z is either not present or amino-lower alkyl; or a radical $R_4$-sulfonylamino-lower alkyl, wherein $R_4$ is lower alkyl, lower alkyl-phenyl, lower alkoxy-phenyl, nitrophenyl or N,N-di-lower alkylamino, and
X is oxygen,
or a salt thereof.

6. A compound of formula I according to claim 1, wherein
$R_1$ is hydrogen,
$R_2$ is a radical selected from the group consisting of amino-lower alkyl, N-lower alkylamino-lower alkyl, N,N-di-lower alkylamino-lower alkyl, N-lower alkylaminocarbonyl, N,N-di-lower alkylaminocarbonyl, guanidino-lower alkyl, lower alkyl-sulfonylamino-lower alkyl, lower alkoxy-phenyl-sulfonylamino-lower alkyl, lower alkyl-phenyl-sulfonylamino-lower alkyl, nitrophenyl-sulfonylamino-lower alkyl, N,N-di-lower alkylamino-sulfonylamino-lower alkyl, lower alkoxycarbonylamino-lower alkyl, lower alkoxy-lower alkoxycarbonylamino-lower alkyl, ureido-lower alkyl, N-lower alkylamino-carbonylamino-lower alkyl, N,N-di-lower alkylamino-carbonylamino-lower alkyl, N-(phenyl-lower alkyl)-amino-carbonylamino-lower alkyl, N-(lower alkyl-phenyl-lower alkyl)-amino-carbonylamino-lower alkyl, N-(lower alkoxy-phenyl-lower alkyl)-amino-carbonylamino-lower alkyl, N-(morpholinyl-lower alkyl)-amino-carbonylamino-lower alkyl, N,N-di-lower alkylamino-lower alkylamino-carbonylamino-lower alkyl, lower alkylcarbonylamino-lower alkyl, piperidyl-lower alkylcarbonylamino-lower alkyl, morpholinyl-lower alkylcarbonylamino-lower alkyl, lower alkyl-piperazinyl-lower alkylcarbonylamino-lower alkyl, morpholinyl-lower alkyl, piperidyl-lower alkyl, pyrrolidinyl-lower alkyl, lower alkyl-piperazinyl lower alkyl, adamantanyl-amino-lower alkyl, hydroxy-piperidyl-lower alkyl, azepanyl-lower alkyl, di-lower alkyl-pyrrolidinyl-lower alkyl, azetidinyl-lower alkyl, aminocarbonyl-piperidyl-lower alkyl, pyridyl-piperazinyl-lower alkyl, thiomorpholinyl-lower alkyl, di-lower alkyl-morpholinyl-lower alkyl, aminocarbonyl-pyrrolidinyl-lower alkyl, lower alkoxycarbonyl-piperazinyl-lower alkyl, phenyl-piperazinyl-lower alkyl, lower alkoxy-lower alkylcarbonylamino-lower akyl, lower alkoxy-lower alkoxy-lower alkylcarbonylamino-lower alkyl, pyrrolidinyl-carbonylamino-lower alkyl, piperidyl-carbonylamino-lower alkyl, morpholinyl-carbonylamino-lower alkyl, lower alkyl-piperazinyl-carbonylamino-lower alkyl, N,N-di-lower alkylamino-lower alkoxycarbonylamino-lower alkyl, morpholinyl-lower alkoxycarbonylamino-lower alkyl and lower alkyl-piperazinyl-lower alkoxycarbonylamino-lower alkyl, and X is oxygen, or a salt thereof.

7. A compound of formula I according to claim 1, selected from the group consisting of cis-7-(3-aminomethyl-cyclobutyl)-5-(3-benzyloxy-phenyl)-7H-pyrrolo[2,3-d]pyrimidin-4-ylamine; trans-7-(3-aminomethyl-cyclobutyl)-5-(3-benzyloxy-phenyl)-7H-pyrrolo[2,3-d]pyrimidin-4-ylamine;

cis-3-[4-amino-5-(3-benzyloxy-phenyl)-pyrrolo[2,3-d]pyrimidin-7-yl]-cyclobutanecarboxylic acid dimethylamide;

trans-3-[4-amino-5-(3-benzyloxy-phenyl)-pyrrolo[2,3-d]pyrimidin-7-yl]-cyclobutanecarboxylic acid dimethylamide;

cis-3-[4-amino-5-(3-benzyloxy-phenyl)-pyrrolo[2,3-d]pyrimidin-7-yl]-cyclobutanecarboxylic acid methylamide;

trans-3-[4-amino-5-(3-benzyloxy-phenyl)-pyrrolo[2,3-d]pyrimidin-7-yl]-cyclobutanecarboxylic acid methylamide;

cis-5-(3-benzyloxy-phenyl)-7-(3-dimethylaminomethyl-cyclobutyl)-7H-pyrrolo[2,3-d]pyrimidin-4-ylamine;

trans-5-(3-benzyloxy-phenyl)-7-(3-dimethylaminomethyl-cyclobutyl)-7H-pyrrolo[2,3-d]pyrimidin-4-ylamine;

cis-5-(3-benzyloxy-phenyl)-7-(3-methylaminomethyl-cyclobutyl)-7H-pyrrolo[2,3-d]pyrimidin-4-ylamine;

trans-5-(3-benzyloxy-phenyl)-7-(3-methylaminomethyl-cyclobutyl)-7H-pyrrolo[2,3-d]pyrimidin-4-ylamine;

trans-N-{3-[4-amino-5-(3-benzyloxy-phenyl)-pyrrolo[2,3-d]pyrimidin-7-yl]-cyclobutylmethyl}-guanidine;

cis-N-{3-[4-amino-5-(3-benzyloxy-phenyl)-pyrrolo[2,3-d]pyrimidin-7-yl]-cyclobutylmethyl}-guanidine;

trans-N-{3-[4-amino-5-(3-benzyloxy-phenyl)-pyrrolo[2,3-d]pyrimidin-7-yl]-cyclobutylmethyl}-methanesulfonamide;

cis-N-{3-[4-amino-5-(3-benzyloxy-phenyl)-pyrrolo[2,3-d]pyrimidin-7-yl]-cyclobutylmethyl}-methanesulfonamide;

trans-N-{3-[4-amino-5-(3-benzyloxy-phenyl)-pyrrolo[2,3-d]pyrimidin-7-yl]-cyclobutylmethyl}-4-methoxy-benzenesulfonamide;

trans-N-{3-[4-amino-5-(3-benzyloxy-phenyl)-pyrrolo[2,3-d]pyrimidin-7-yl]-cyclobutylmethyl}-4-methyl-benzenesulfonamide;

trans-N-{3-[4-amino-5-(3-benzyloxy-phenyl)-pyrrolo[2,3-d]pyrimidin-7-yl]-cyclobutylmethyl}-4-nitro-benzenesulfonamide;

propane-2-sulfonic acid trans-{3-[4-amino-5-(3-benzyloxy-phenyl)-pyrrolo[2,3-d]pyrimidin-7-yl]-cyclobutylmethyl}-amide;

ethanesulfonic acid trans-{3-[4-amino-5-(3-benzyloxy-phenyl)-pyrrolo[2,3-d]pyrimidin-7-yl]-cyclobutylmethyl}-amide;

N-dimethyl-sulfamide trans-{3-[4-amino-5-(3-benzyloxy-phenyl)-pyrrolo[2,3-d]pyrimidin-7-yl]-cyclobutylmethyl}-amide;

N-dimethyl-sulfamide cis-{3-[4-amino-5-(3-benzyloxy-phenyl)-pyrrolo[2,3-d]pyrimidin-7-yl]-cyclobutylmethyl}-amide;

trans-{3-[4-amino-5-(3-benzyloxy-phenyl)-pyrrolo[2,3-d]pyrimidin-7-yl]-cyclobutylmethyl}-carbamic acid methyl ester;

cis-{3-[4-amino-5-(3-benzyloxy-phenyl)-pyrrolo[2,3-d]pyrimidin-7-yl]-cyclobutylmethyl}-carbamic acid methyl ester;

trans-{3-[4-amino-5-(3-benzyloxy-phenyl)-pyrrolo[2,3-d]pyrimidin-7-yl]-cyclobutylmethyl}-carbamic acid 2-methoxy-ethyl ester;

cis-{3-[4-amino-5-(3-benzyloxy-phenyl)-pyrrolo[2,3-d]pyrimidin-7-yl]-cyclobutylmethyl}-carbamic acid 2-methoxy-ethyl ester;

trans-1-{3-[4-amino-5-(3-benzyloxy-phenyl)-pyrrolo[2,3-d]pyrimidin-7-yl]-cyclobutylmethyl}-3-ethyl-urea;

cis-{3-[4-amino-5-(3-benzyloxy-phenyl)-pyrrolo[2,3-d]pyrimidin-7-yl]-cyclobutylmethyl}-3-ethyl-urea;

trans-1-{3-[4-amino-5-(3-benzyloxy-phenyl)-pyrrolo[2,3-d]pyrimidin-7-yl]-cyclobutylmethyl}-3-propyl-urea;

cis-1-{3-[4-amino-5-(3-benzyloxy-phenyl)-pyrrolo[2,3-d]pyrimidin-7-yl]-cyclobutylmethyl}-3-propyl-urea;

trans-1-{3-[4-amino-5-(3-benzyloxy-phenyl)-pyrrolo[2,3-d]pyrimidin-7-yl]-cyclobutylmethyl}-3-isopropyl-urea;

cis-1-{3-[4-amino-5-(3-benzyloxy-phenyl)-pyrrolo[2,3-d]pyrimidin-7-yl]-cyclobutylmethyl}-3-isopropyl-urea;

trans-1-{3-[4-amino-5-(3-benzyloxy-phenyl)-pyrrolo[2,3-d]pyrimidin-7-yl]-cyclobutylmethyl}-3-butyl-urea;

cis-1-{3-[4-amino-5-(3-benzyloxy-phenyl)-pyrrolo[2,3-d]pyrimidin-7-yl]-cyclobutylmethyl}-3-butyl-urea;

trans-1-{3-[4-amino-5-(3-benzyloxy-phenyl)-pyrrolo[2,3-d]pyrimidin-7-yl]-cyclobutylmethyl}-3-tert-butyl-urea;

cis-1-{3-[4-amino-5-(3-benzyloxy-phenyl)-pyrrolo[2,3-d]pyrimidin-7-yl]-cyclobutylmethyl}-3-tert-butyl-urea;

trans-1-{3-[4-amino-5-(3-benzyloxy-phenyl)-pyrrolo[2,3-d]pyrimidin-7-yl]-cyclobutylmethyl}-3-benzyl-urea;

trans-1-{3-[4-amino-5-(3-benzyloxy-phenyl)-pyrrolo[2,3-d]pyrimidin-7-yl]-cyclobutylmethyl}-3-(3-methyl-benzyl)-urea;

cis-1-{3-[4-amino-5-(3-benzyloxy-phenyl)-pyrrolo[2,3-d]pyrimidin-7-yl]-cyclobutylmethyl}-3-(3-methyl-benzyl)-urea;

cis-1-{3-[4-amino-5-(3-benzyloxy-phenyl)-pyrrolo[2,3-d]pyrimidin-7-yl]-cyclobutylmethyl}-3-(4-methoxy-benzyl)-urea;

trans-1-{3-[4-amino-5-(3-benzyloxy-phenyl)-pyrrolo[2,3-d]pyrimidin-7-yl]-cyclobutylmethyl}-3-(2-morpholin-4-yl-ethyl)-urea;

cis-1-{3-[4-amino-5-(3-benzyloxy-phenyl)-pyrrolo[2,3-d]pyrimidin-7-yl]-cyclobutylmethyl}-3-(2-morpholin-4-yl-ethyl)-urea;

trans-1-{3-[4-amino-5-(3-benzyloxy-phenyl)-pyrrolo[2,3-d]pyrimidin-7-yl]-cyclobutylmethyl}-3-(2-dimethylamino-ethyl)-urea;

cis-1-{3-[4-amino-5-(3-benzyloxy-phenyl)-pyrrolo[2,3-d]pyrimidin-7-yl]-cyclobutylmethyl}-3-(2-dimethylamino-ethyl)-urea;

trans-1-{3-[4-amino-5-(3-benzyloxy-phenyl)-pyrrolo[2,3-d]pyrimidin-7-yl]-cyclobutylmethyl}-3-(3-morpholin-4-yl-propyl)-urea;

cis-1-{3-[4-amino-5-(3-benzyloxy-phenyl)-pyrrolo[2,3-d]pyrimidin-7-yl]-cyclobutylmethyl}-3-(3-morpholin-4-yl-propyl)-urea;
trans-1-{3-[4-amino-5-(3-benzyloxy-phenyl)-pyrrolo[2,3-d]pyrimidin-7-yl]-cyclobutylmethyl}-3-(3-dimethylamino-propyl)-urea;
cis-1-{3-[4-amino-5-(3-benzyloxy-phenyl)-pyrrolo[2,3-d]pyrimidin-7-yl]-cyclobutylmethyl}-3-(3-dimethylamino-propyl)-urea;
trans-{3-[4-amino-5-(3-benzyloxy-phenyl)-pyrrolo[2,3-d]pyrimidin-7-yl]-cyclobutylmethyl}-urea;
cis-{3-[4-amino-5-(3-benzyloxy-phenyl)-pyrrolo[2,3-d]pyrimidin-7-yl]-cyclobutylmethyl}-urea;
trans-N-{3-[4-amino-5-(3-benzyloxy-phenyl)-pyrrolo[2,3-d]pyrimidin-7-yl]-cyclobutylmethyl}-acetamide;
cis-N-{3-[4-amino-5-(3-benzyloxy-phenyl)-pyrrolo[2,3-d]pyrimidin-7-yl]-cyclobutylmethyl}-acetamide;
trans-N-{3-[4-amino-5-(3-benzyloxy-phenyl)-pyrrolo[2,3-d]pyrimidin-7-yl]-cyclobutylmethyl}-isobutyramide;
cis-N-{3-[4-amino-5-(3-benzyloxy-phenyl)-pyrrolo[2,3-d]pyrimidin-7-yl]-cyclobutylmethyl}-isobutyramide;
trans-N-{3-[4-amino-5-(3-benzyloxy-phenyl)-pyrrolo[2,3-d]pyrimidin-7-yl]-cyclobutylmethyl}-2,2-dimethyl-propionamide;
cis-N-{3-[4-amino-5-(3-benzyloxy-phenyl)-pyrrolo[2,3-d]pyrimidin-7-yl]-cyclobutylmethyl}-2,2-dimethyl-propionamide;
N-trans-{3-[4-amino-5-(3-benzyloxy-phenyl)-pyrrolo[2 3-d]pyrimidin-7-yl]-cyclobutylmethyl}-2-piperidin-1-yl-acetamide;
cis-N-{3-[4-amino-5-(3-benzyloxy-phenyl)-pyrrolo[2,3-d]pyrimidin-7-yl]-cyclobutylmethyl}-2-piperidin-1-yl-acetamide;
trans-N-{3-[4-amino-5-(3-benzyloxy-phenyl)-pyrrolo[2,3-d]pyrimidin-7-yl]-cyclobutylmethyl}-2-morpholin-4-yl-acetamide;
cis-N-{3-[4-amino-5-(3-benzyloxy-phenyl)-pyrrolo[2,3-d]pyrimidin-7-yl]-cyclobutylmethyl}-2-morpholin-4-yl-acetamide;
trans-N-{3-[4-amino-5-(3-benzyloxy-phenyl)-pyrrolo[2,3-d]pyrimidin-7-yl]-cyclobutylmethyl}-2-(4-methyl-piperazin-1-yl)-acetamide;
cis-N-{3-[4-amino-5-(3-benzyloxy-phenyl)-pyrrolo[2,3-d]pyrimidin-7-yl]-cyclobutylmethyl}-2-(4-methyl-piperazin-1-yl)-acetamide;
trans-5-(3-benzyloxy-phenyl)-7-(3-morpholin-4-ylmethyl-cyclobutyl)-7H-pyrrolo[2,3-d]pyrimidin-4-ylamine;
trans-5-(3-benzyloxy-phenyl)-7-(3-piperidin-1-ylmethyl-cyclobutyl)-7H-pyrrolo[2,3-d]pyrimidin-4-ylamine;
trans-5-(3-benzyloxy-phenyl)-7-(3-pyrrolidin-1-ylmethyl-cyclobutyl)-7H-pyrrolo[2,3-d]pyrimidin-4-ylamine;
trans-5-(3-benzyloxy-phenyl)-7-[3-(4-methyl-piperazin-1-ylmethyl)-cyclobutyl]-7H-pyrrolo[2,3-d]pyrimidin-4-ylamine;
trans-7-[3-(adamantan-1-ylaminomethyl)-cyclobutyl]-5-(3-benzyloxy-phenyl)-7H-pyrrolo[2,3-d]pyrimidin-4-ylamine;
trans-1-{3-[4-amino-5-(3-benzyloxy-phenyl)-pyrrolo[2,3-d]pyrimidin-7-yl]-cyclobutylmethyl}-piperidin-4-ol;
trans-7-(3-azepan-1-ylmethyl-cyclobutyl)-5-(3-benzyloxy-phenyl)-7H-pyrrolo[2,3-d]pyrimidin-4-ylamine;
trans-5-(3-benzyloxy-phenyl)-7-[3-(2,5-dimethyl-pyrrolidin-1-ylmethyl)-cyclobutyl]-7H-pyrrolo[2,3-d]pyrimidin-4-ylamine;
trans-7-(3-azetidin-1-ylmethyl-cyclobutyl)-5-(3-benzyloxy-phenyl)-7H-pyrrolo[2,3-d]pyrimidin-4-ylamine;
trans-1-{3-[4-amino-5-(3-benzyloxy-phenyl)-pyrrolo[2,3-d]pyrimidin-7-yl]-cyclobutylmethyl}-piperidine-3-carboxylic acid amide;
trans-5-(3-benzyloxy-phenyl)-7-[3-(4-pyridin-2-yl-piperazin-1-ylmethyl)-cyclobutyl]-7H-pyrrolo[2,3-d]pyrimidin-4-ylamine;
trans-5-(3-benzyloxy-phenyl)-7-(3-thiomorpholin-4-ylmethyl-cyclobutyl)-7H-pyrrolo[2,3-d]pyrimidin-4-ylamine;
trans-5-(3-benzyloxy-phenyl)-7-[3-(2,6-dimethyl-morpholin-4-ylmethyl)-cyclobutyl]-7H-pyrrolo[2,3-d]pyrimidin-4-ylamine;
trans-(S)-1-{3-[4-amino-5-(3-benzyloxy-phenyl)-pyrrolo[2,3-d]pyrimidin-7-yl]-cyclobutylmethyl}-pyrrolidine-2-carboxylic acid amide;
cis-7-(3-azepan-1-ylmethyl-cyclobutyl)-5-(3-benzyloxy-phenyl)-7H-pyrrolo[2,3-d]pyrimidin-4-ylamine;
cis-1-{3-[4-amino-5-(3-benzyloxy-phenyl)-pyrrolo[2,3-d]pyrimidin-7-yl]-cyclobutylmethyl}-piperidin-4-ol;
cis-4-{3-[4-amino-5-(3-benzyloxy-phenyl)-pyrrolo[2,3-d]pyrimidin-7-yl]-cyclobutylmethyl}-piperazine-1-carboxylic acid ethyl ester;
cis-5-(3-benzyloxy-phenyl)-7-[3-(4-phenyl-piperazin-1-ylmethyl)-cyclobutyl]-7H-pyrrolo[2,3-d]pyrimidin-4-ylamine;
cis-5-(3-benzyloxy-phenyl)-7-[3-(4-methyl-piperazin-1-ylmethyl)-cyclobutyl]-7H-pyrrolo[2,3-d]pyrimidin-4-ylamine;
cis-5-(3-benzyloxy-phenyl)-7-(3-thiomorpholin-4-ylmethyl-cyclobutyl)-7H-pyrrolo[2,3-d]pyrimidin-4-ylamine;
cis-5-(3-benzyloxy-phenyl)-7-[3-(2,6-dimethyl-morpholin-4-ylmethyl)-cyclobutyl]-7H-pyrrolo[2,3-d]pyrimidin-4-ylamine;
cis-(R)-1-{3-[4-amino-5-(3-benzyloxy-phenyl)-pyrrolo[2,3-d]pyrimidin-7-yl]-cyclobutylmethyl}-pyrrolidine-2-carboxylic acid amide;
cis-1-{3-[4-amino-5-(3-benzyloxy-phenyl)-pyrrolo[2,3-d]pyrimidin-7-yl]-cyclobutylmethyl}-piperidine-3-carboxylic acid amide;
trans-N-{3-[4-amino-5-(3-benzyloxy-phenyl)-pyrrolo[2,3-d]pyrimidin-7-yl]-cyclobutylmethyl}-2-ethoxy-acetamide;
trans-N-{3-[4-amino-5-(3-benzyloxy-phenyl)-pyrrolo[2,3-d]pyrimidin-7-yl]-cyclobutylmethyl}-2-(2-methoxy-ethoxy)-acetamide;
trans-1-{3-[4-amino-5-(3-benzyloxy-phenyl)-pyrrolo[2,3-d]pyrimidin-7-yl]-cyclobutylmethyl}-3-methyl-urea;
cis-1-{3-[4-amino-5-(3-benzyloxy-phenyl)-pyrrolo[2,3-d]pyrimidin-7-yl]-cyclobutylmethyl}-3-methyl-urea;
trans-pyrrolidine-1-carboxylic acid {3-[4-amino-5-(3-benzyloxy-phenyl)-pyrrolo[2,3-d]pyrimidin-7-yl]-cyclobutylmethyl}-amide;
trans-piperidine-1-carboxylic acid {3-[4-amino-5-(3-benzyloxy-phenyl)-pyrrolo[2,3-d]pyrimidin-7-yl]-cyclobutylmethyl}-amide;
trans-morpholine-4-carboxylic acid {3-[4-amino-5-(3-benzyloxy-phenyl)-pyrrolo[2,3-d]pyrimidin-7-yl]-cyclobutylmethyl}-amide;
trans-3-{3-[4-amino-5-(3-benzyloxy-phenyl)-pyrrolo[2,3-d]pyrimidin-7-yl]-cyclobutylmethyl}-1,1-dimethyl-urea;
trans-4-methyl-piperazine-1-carboxylic acid {3-[4-amino-5-(3-benzyloxy-phenyl)-pyrrolo[2,3-d]pyrimidin-7-yl]-cyclobutylmethyl}-amide;

trans-3-{3-[4-amino-5-(3-benzyloxy-phenyl)-pyrrolo[2,3-d]pyrimidin-7-yl]-cyclobutylmethyl}-1,1-diethyl-urea;

trans-{3-[4-amino-5-(3-benzyloxy-phenyl)-pyrrolo[2,3-d]pyrimidin-7-yl]-cyclobutylmethyl}-carbamic acid 2-diethylamino-ethyl ester;

trans-{3-[4-amino-5-(3-benzyloxy-phenyl)-pyrrolo[2,3-d]pyrimidin-7-yl]-cyclobutylmethyl}-carbamic acid 2-morpholin-4-yl-ethyl ester;

trans-{3-[4-amino-5-(3-benzyloxy-phenyl)-pyrrolo[2,3-d]pyrimidin-7-yl]-cyclobutylmethyl}-carbamic acid 2-(4-methyl-piperazin-1-yl)-ethyl ester;

trans-{3-[4-amino-5-(3-benzyloxy-phenyl)-pyrrolo[2,3-d]pyrimidin-7-yl]-cyclobutylmethyl}-carbamic acid 2-dimethylamino-ethyl ester;

trans-{3-[4-amino-5-(3-benzyloxy-phenyl)-pyrrolo[2,3-d]pyrimidin-7-yl]-cyclobutylmethyl}-carbamic acid ethyl ester;

trans-4-{3-[4-amino-5-(3-benzyloxy-phenyl)-pyrrolo[2,3-d]pyrimidin-7-yl]-cyclobutylmethyl}-piperazine-1-carboxylic acid ethyl ester;

cis-5-(3-benzyloxy-phenyl)-7-(3-pyrrolidin-1-ylmethyl-cyclobutyl)-7H-pyrrolo[2,3-d]pyrimidin-4-ylamine;

cis-7-(3-azetidin-1-ylmethyl-cyclobutyl)-5-(3-benzyloxy-phenyl)-7H-pyrrolo[2,3-d]pyrimidin-4-ylamine;

and pharmaceutically acceptable salts thereof.

8. A pharmaceutical composition comprising a compound of formula I according to claim 1, together with at least one pharmaceutically acceptable carrier.

9. A process for the preparation of a compound of formula I according to claim 1, in which $R_2$ is lower alkyl substituted by a heterocyclic radical containing at least one nitrogen ring atom whereby the binding of the heterocyclic radical to lower alkyl occurs via a nitrogen ring atom, or of a salt of such a compound, characterized in that a compound of formula IV

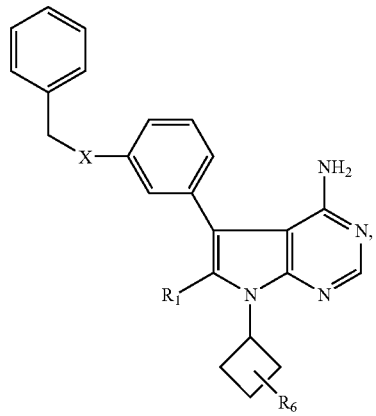

(IV)

in which $R_6$ is lower alkyl substituted by 4-methylphenyl-sulfonyloxy and $R_1$ and X have the meanings as defined for a compound of formula I according to claim 1 is reacted with a heterocycle which contains at least one nitrogen ring atom, whereby functional groups which are present in a compound of formula IV and in said heterocycle which contains at least one nitrogen ring atom and are not intended to take part in the reaction, are present in protected form if necessary, and protecting groups that are present are cleaved, whereby said compound of formula IV or said heterocycle may also exist in the form of salts provided that a salt-forming group is present and a reaction in salt form is possible, and, if so desired, a compound of formula I thus obtained is converted into another compound of formula I, a free compound of formula I is converted into a salt, an obtained salt of a compound of formula I is converted into the free compound or another salt, and/or a mixture of isomeric compounds of formula I is separated into the individual isomers.

* * * * *